United States Patent
Wang et al.

(10) Patent No.: US 8,283,368 B2
(45) Date of Patent: Oct. 9, 2012

(54) SELECTIVE LIGANDS FOR THE DOPAMINE 3 ($D_3$) RECEPTOR AND METHODS OF USING THE SAME

(75) Inventors: Shaomeng Wang, Saline, MI (US); Jianyong Chen, Ann Arbor, MI (US); Gregory Collins, Medford, MA (US); James H. Woods, Ann Arbor, MI (US); Beth Levant, Kansas City, MO (US)

(73) Assignee: The Regents of the University of Michigan, Ann Arbor, MI (US)

( * ) Notice: Subject to any disclaimer, the term of this patent is extended or adjusted under 35 U.S.C. 154(b) by 4 days.

(21) Appl. No.: 13/060,306

(22) PCT Filed: Aug. 27, 2009

(86) PCT No.: PCT/US2009/055169
§ 371 (c)(1), (2), (4) Date: Apr. 14, 2011

(87) PCT Pub. No.: WO2010/025235
PCT Pub. Date: Mar. 4, 2010

(65) Prior Publication Data
US 2011/0184033 A1 Jul. 28, 2011

Related U.S. Application Data

(60) Provisional application No. 61/092,830, filed on Aug. 29, 2008.

(51) Int. Cl.
*A01N 43/78* (2006.01)
*A61K 31/425* (2006.01)
(52) U.S. Cl. .................... 514/367; 548/164
(58) Field of Classification Search .......... 514/367; 548/164
See application file for complete search history.

(56) References Cited

FOREIGN PATENT DOCUMENTS

| EP | 1878731 A1 | 1/2008 |
|---|---|---|
| WO | WO-9504713 A1 | 2/1995 |
| WO | WO-2009056811 A2 | 5/2009 |

OTHER PUBLICATIONS

Bancroft, G. N., et al., "Binding of [3H]PD 128907, a putatively selective ligand for the D3 dopamine receptor, in rat brain: a receptor binding and quantitative autoradiographic study." *Neuropsychopharmacology*, 1998, 18, 305-316.

(Continued)

*Primary Examiner* — Yong Chu
*Assistant Examiner* — Valerie Rodriguez-Garcia
(74) *Attorney, Agent, or Firm* — Marshall, Gerstein & Borun LLP

(57) ABSTRACT

Potent and selective ligands for the dopamine 3 ($D_3$) receptor are disclosed. The D3 receptor ligands have a structural formula (I) wherein X is C=O or $SO_2$, $R^1$ is $C_{1-6}$ alkyl, $R^2$ is aryl, heteroaryl, aryl, —$(CH_2)_{1-3}$aryl, or —$(CH_2)_{1-3}$heteroaryl, and n is 0 or 1. Methods of using the $D^3$ receptor ligands in the treatment of diseases and conditions wherein modulation of the $D_3$ receptor provides a benefit also are disclosed.

(I)

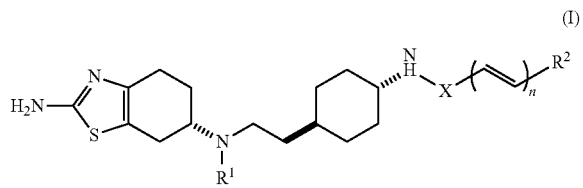

26 Claims, 4 Drawing Sheets

OTHER PUBLICATIONS

Belliotti, T. B., et al., "Novel cyclohexyl amides as potent and selective $D_3$ dopamine receptor ligands." *Bioorg. Med. Chem. Letts*, 1997, 7, 2403-2408.

Bettinetti, L., et al., "Interactive SAR studies: rational discovery of super-potent and highly selective $D_3$ receptor antagonists and partial agonists," *J. Med. Chem.*., 2002, 45, 4594-4597.

Boulay, D., et al., "Dopamine D2 receptor knock-out mice are insensitive to the hypolocomotor and hypothermic effects of dopamine D2/D3 receptor agonists." *Neuropharmacology*, 1999, 38, 1389-96.

Campiani, G., et al., "Pyrrolo[1,3]benzothiazepine-based serotonin and dopamine receptor antagonists: molecular modeling, further structure activity relationship studies, and identification of novel atypical antipsychotic agents." *J. Med. Chem.*, 2004, 47, 143-157.

Campiani, G., et al., "Synthesis and pharmacological evaluation of potent and highly selective $D_3$ receptor ligands: inhibition of cocaine-seeking behavior and the role of dopamine $D_3/D$ receptors." *J. Med. Chem.*, 2003, 46, 3822-3839.

Chaperon, F., et al., "Evidence for regulation of body temperature in rats by dopamine D2 receptor and possible influence of D1 but not D3 and D4 receptors." *Neuropharmacology*, 2003, 44, 1047-53.

Chen, J., et al., "Design of Novel Hexahydropyrazinoquinolines as Potent and Selective Dopamine D3 Receptor Ligands with Improved Solubility." *Bioorg. Med. Chem. Lett*, 2006, 16, 443-446.

Chen, J., et al.,"Design, Synthesis, and Evaluation of Potent and Selective Ligands for the Dopamine 3 (D3) Receptor with a Novel in Vivo Behavioral Profile," *J. Med. Chem.*, 2008, 51, 5905-5908.

Cherezov, V., et al., "High resolution crystal structure of an engineered human beta2-adrenergic G protein-coupled receptor." *Science*, 2007, 318, 1258-1265.

Collins, G. T., et al., "Yawning and hypothermia in rats: effects of dopamine D3 and D2 agonists and antagonists." *Psychopharmacology (Berl)*, 2007, 193, 159-70.

Ding, K., et al., "Enantiomerically Pure Hexahydropyrazinoquinolines as Potent and Selective Dopamine 3 Subtype Receptor Ligands." *J. Med. Chem.*, 2005, 48, 3171-3181.

Fujikawa, M., et al., "Partial agonistic effects of OPC-14597, a potential antipsychotic agent, on yawning behavior in rats." *Pharmacol. Biochem. Behav.*, 1996, 53, 903-909.

Grundt, P., et al., "Heterocyclic Analogues of N-(4-(4-(2,3-Dichlorophenyl)piperazin-l-yl)butyl)arylcarboxamides with Functionalized Linking Chains as Novel Dopamine D3 Receptor Ligands: Potential Substance Abuse Therapeutic Agents." *J. Med. Chem.*, 2007, 50, 4135-4146.

Grundt, P., et al., "Novel Heterocyclic Trans Olefin Analogues of N-{4-[4-(2,3-Dichlorophenyl)piperazin-l-yl]butyl}arylcarboxamides as Selective Probes with High Affinity for the Dopamine $D_3$ Receptor." *J. Med. Chem.*, 2005, 48, 839-848.

Hackling, A., et al., "N-(ö-(4-(2-Methoxyphenyl)piperazin-1-yl)alkyl) carboxamides as dopamine $D_2$ and $D_3$ receptor ligands." *J. Med. Chem*,. 2003, 46, 3883-3899.

Ji, M., et al., "Design, synthesis and structure-activity relationship studies of hexahydropyrazinoquinolines as a novel class of potent and selective dopamine receptor 3 (D3) ligands." *Bioorg. Med. Chem. Lett*., 2005, 15, 1701-1705.

Kenakin, T., "The classification of seven transmembrane receptors in recombinant expression systems." *Pharmacol. Rev.*, 1996, 48, 413-463.

Leopoldo, M., et al., "Structure-affinity relationship study on N-[4-(4-arylpiperazin-1-yl)butyl]arylcarboxamides as potent and selective dopamine $D_3$ receptor ligands." *J. Med. Chem.*, 2002, 45, 5727-5735.

Levant, B., "Characterization of dopamine receptors." "In Current Protocols in Pharmacology"; Enna, S. J, et al., Eds.; John Wiley & Sons: New York, 1998, pp. 1.6.1-1.6.16.

Newman, A. H., et al., "Dopamine $D_3$ Receptor Partial Agonists and Antagonists as Potential Drug Abuse Therapeutic Agents." *J. Med. Chem.*, 2005, 48, 3663-3679.

Rasmussen, S. G., et al., "Crystal structure of the human beta2 adrenergic G-protein-coupled receptor." *Nature*, 2007, 450, 383-7.

Robarge, M. J., et al., "Design and synthesis of [(2,3-dichlorophenyl)piperazin-1-yl] alkylfluorenylcarboxamides as novel ligands selective for the dopamine $D_3$ receptor subtype." *J. Med. Chem.*, 2001, 44, 3175-3186.

Svensson, S. R. Haadsma, et al., "Dopamine $D_3$ receptor antagonists. 1. Synthesis and structure-activity relationship of 5,6-dimethoxy-N-alkyl- and N-alkylaryl-substituted 2-aminoindans." *J. Med. Chem.*, 2001, 44, 4716-4732.

Varady, J., et al., "Molecular modeling of the three-dimensional structure of dopamine 3 subtype receptor. Discovery of novel and potent $D_3$ ligands through a hybrid pharmacophore- and structure-based database searching approach." *J. Med. Chem.*, 2003, 46, 4377-4392.

Wustrow, D. J., et al., "Studies of the active conformation of a novel series of benzamide dopamine $D_2$ agonists." *J. Med. Chem.*, 1994, 37, 4251-4257.

Wustrow, D., et al., "Aminopyrimidines with high affinity for both serotonin and dopamine receptors." *J. Med. Chem.* 1998, 41, 760-771.

International Search Report in PCT Application No. PCT/US2009/055169, dated Dec. 7, 2009.

SELECTIVE LIGANDS FOR THE DOPAMINE 3 ($D_3$) RECEPTOR AND METHODS OF USING THE SAME

CROSS-REFERENCE TO RELATED APPLICATIONS

This is the U.S. national phase of International Application No. PCT/US2009/055169, filed Aug. 27, 2009, which claims the benefit of U.S. provisional patent Application No. 61/092,830, filed Aug. 29, 2008.

STATEMENT OF GOVERNMENTAL INTEREST

This invention was made with government support under Grant No. R01DA020669, awarded by the National Institute of Drug Abuse, National Institutes of Health. The government has certain rights in the invention.

FIELD OF THE INVENTION

The present invention relates to ligands for the dopamine 3 ($D_3$) receptor and to therapeutic methods of treating conditions and diseases wherein modulation of the $D_3$ receptor provides a benefit.

BACKGROUND OF THE INVENTION

Dopamine (DA) is a neurotransmitter that plays an essential role in normal brain functions. As a chemical messenger, dopamine is similar to adrenaline. In the brain, dopamine is synthesized in the pre-synaptic neurons and released into the space between the pre-synaptic and post-synaptic neurons.

Dopamine affects brain processes that control movement, emotional response, and ability to experience pleasure and pain. Therefore, the regulation of dopamine plays an important role in mental and physical health. Neurons containing dopamine are clustered in the midbrain area called the substantia nigra. Abnormal dopamine signaling in the brain has been implicated in a substantial number of pathological conditions, including drug (e.g., cocaine) abuse, depression, anxiety, schizophrenia, Tourette's syndrome, eating disorders, alcoholism, chronic pain, obsessive compulsive disorders, restless leg syndrome, Parkinson's Disease, and the like.

Dopamine molecules bind to and activate dopamine receptors on the post-synaptic neurons. Dopamine molecules then are transported through the dopamine transporter protein (DAT) back into the pre-synaptic neurons, where they are metabolized by monoamine oxidase (MAO). In conditions such as cocaine abuse, cocaine binds to the dopamine transporter and blocks the normal flow of dopamine molecules. Excess concentrations of dopamine cause over-activation of dopamine receptors. In other conditions, such as Parkinson's Disease, lack of sufficient dopamine receptors in the brain causes insufficient activation of dopamine receptors.

Dopaminergic neurotransmission is mediated by five dopamine receptors ($D_1$-$D_5$) that can be grouped into the $D_1$-like ($D_1$ and $D_5$) and $D_2$-like ($D_2$, $D_3$ and $D_4$) receptor subtypes. Recent studies suggest that the $D_3$ receptor is a promising therapeutic target for a variety of conditions, including drug abuse, restless leg syndrome, schizophrenia, Parkinson's disease, and depression (1-6). Therefore, considerable effort has been expended to discover and develop potent and selective $D_3$ ligands (6-22).

Despite these intense efforts, the design and discovery of truly selective $D_3$ ligands with good aqueous solubility and bioavailability remains a challenge. Compound 1 (pramipexole) is a known, potent $D_3$-preferring agonist, but has limited selectivity over the $D_2$ receptor in vitro (23) and in vivo (24, 25). Compound 2 (BP 897) initially was reported as a $D_3$ partial agonist and has a 67-fold selectivity over the $D_2$ receptor (2).

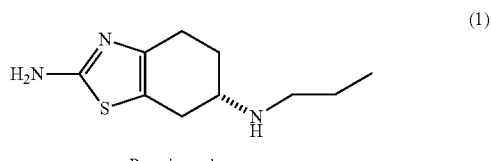

Pramipexole

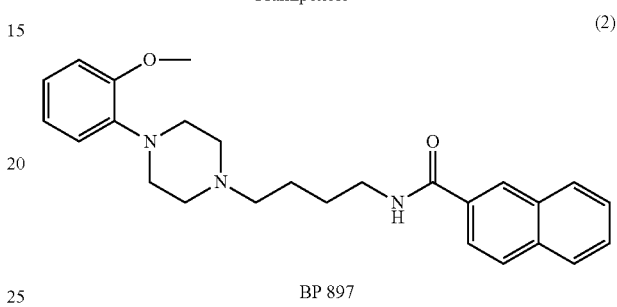

BP 897

A number of potent and selective $D_3$ ligands, such as compound 3, have been designed based upon the core structure of compound 2 (17). Compound 4 is a potent and selective $D_3$ ligand using hexahydropyrazinoquinoline as the core structure. Despite its relatively high affinity and excellent selectivity for $D_3$ over other dopamine receptor subtypes, compound 4 has a poor aqueous solubility, which limits in vivo evaluations. Poor aqueous solubility also is a major limitation for many recently disclosed selective $D_3$ ligands, and is an obstacle for evaluating these compounds in animal behavioral models and for a therapeutic potential.

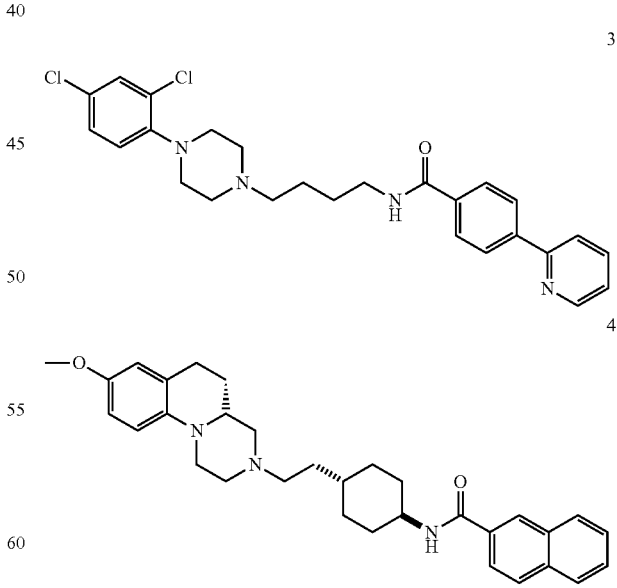

Accordingly, a need still exists in the art for a potent and selective $D_3$ ligand having physical and pharmacological properties that permit use of the ligand in therapeutic applications. The present invention provides ligands designed to selectively bind to the $D_3$ receptor subtype to partially, or fully, modulate (e.g., agonism and/or antagonism) the $D_3$ receptor with high selectivity.

SUMMARY OF THE INVENTION

The present invention is directed to potent and selective ligands for $D_3$ receptors and to methods of using the ligands in a therapeutic treatment of conditions and diseases wherein modulation of the $D_3$ receptors provides a benefit. More particularly, the present invention is directed to compounds having a structural formula (I):

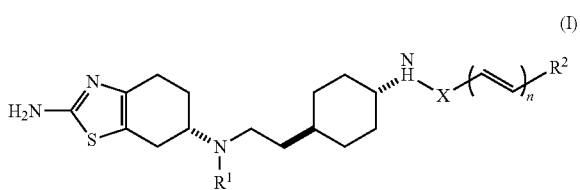

wherein X is C(=O) or $SO_2$, $R^1$ is $C_{1-6}$ alkyl, $R^2$ is aryl, heteroaryl, aryl, —$(CH_2)_{1-3}$aryl, or —$(CH_2)_{1-3}$heteroaryl, and n is 0 or 1, or a pharmaceutically acceptable salt, solvate, or hydrate thereof.

In one embodiment, the present invention provides a method of treating a condition or disease by administering a therapeutically effective amount of a compound of structural formula (I) to an individual in need thereof. The disease or condition of interest is treatable by modulation of $D_3$ receptors, such as, for example, drug abuse, Parkinson's disease, restless leg syndrome, schizophrenia, and depression.

Another embodiment of the present invention is to provide a composition comprising a $D_3$ receptor ligand of structural formula (I) and an excipient and/or pharmaceutically acceptable carrier useful in treating diseases or conditions wherein modulation of $D_3$ receptors provides a benefit, i.e., a disease or condition of interest.

Another embodiment of the present invention is to utilize a composition comprising a compound of structural formula (I) and a second therapeutically active agent in a method of treating an individual for a disease or condition wherein modulation of $D_3$ receptors provides a benefit.

In a further embodiment, the invention provides for use of a composition comprising a $D_3$ ligand of structural formula (I) and an optional second therapeutic agent for the manufacture of a medicament for treating a disease or condition of interest, e.g., drug abuse, Parkinson's disease, restless leg syndrome, schizophrenia, and depression.

Still another embodiment of the present invention is to provide a kit for human pharmaceutical use, comprising (a) a container, (b1) a packaged composition comprising a $D_3$ ligand of structural formula (I) and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition.

The $D_3$ ligand of structural formula (I) and the second therapeutic agent can be administered together as a single-unit dose or separately as multi-unit doses, wherein the $D_3$ ligand of structural formula (I) is administered before the second therapeutic agent or vice versa. It is envisioned that one or more dose of the $D_3$ ligand of structural formula (I) or one and/or more dose of the second therapeutic agent can be administered.

In one embodiment, the $D_3$ ligand of structural formula (I) and second therapeutic agent are administered simultaneously. In related embodiments, the $D_3$ ligand of structural formula (I) and second therapeutic agent are administered from a single composition or from separate compositions. In a further embodiment, the $D_3$ ligand of structural formula (I) and second therapeutic agent are administered sequentially. The $D_3$ ligand of structural formula (I), as used in the present invention, can be administered in an amount of about 0.005 to about 500 milligrams per dose, about 0.05 to about 250 milligrams per dose, or about 0.5 to about 100 milligrams per dose.

In one preferred embodiment, the present invention provides a method of treating a subject having a disease, addiction, or other pathological condition (e.g., cocaine abuse, depression, anxiety, an eating disorder, alcoholism, chronic pain, obsessive compulsive disorder, schizophrenia, restless leg syndrome (RLS), Parkinson's disease, and the like) comprising administering to the subject a therapeutic dose of a compound of structural formula (I) or a composition containing the compound.

These and other aspects and features of the present invention will become apparent from the following drawings and detailed description of the preferred embodiments.

DETAILED DESCRIPTION OF THE PREFERRED EMBODIMENTS

Figure 1:
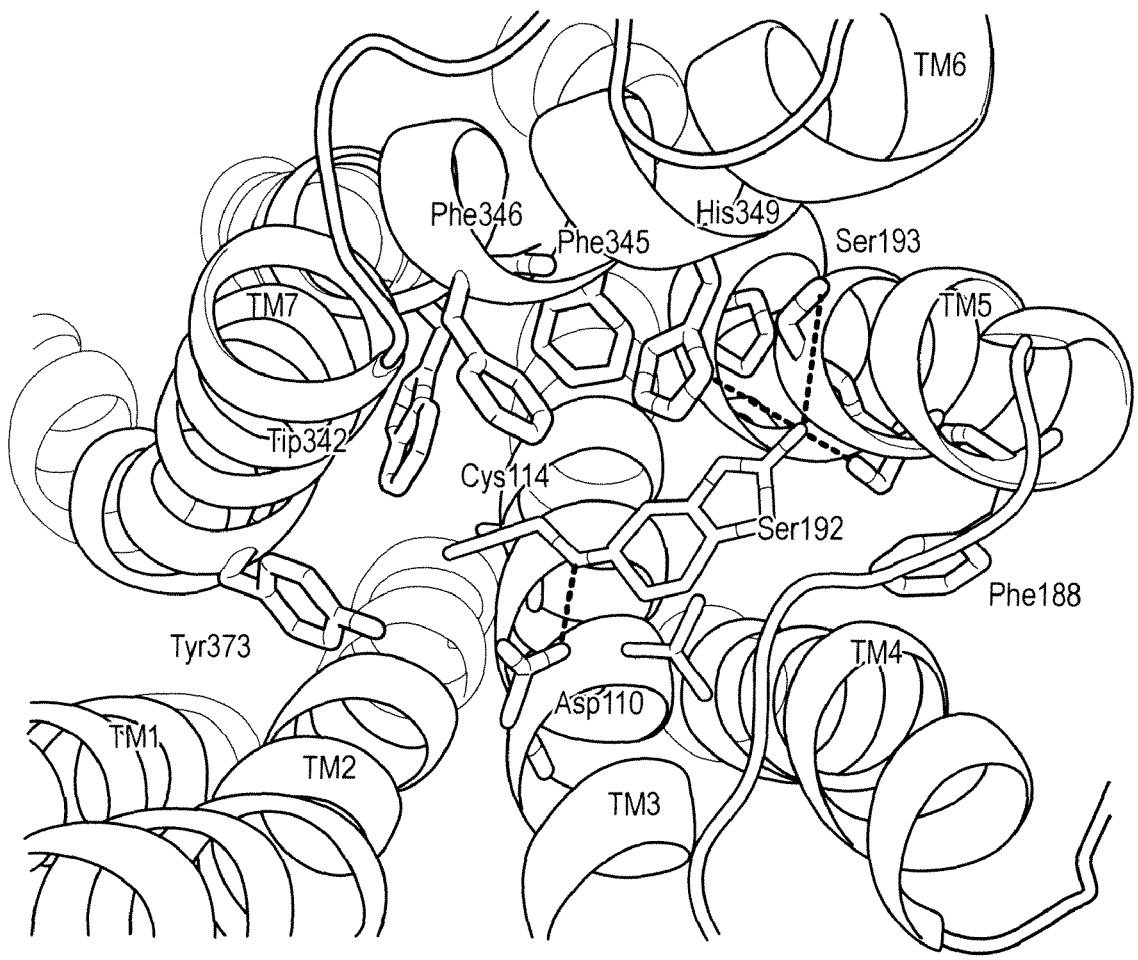
FIG. 1 illustrates the predicted binding model of compound 1 (pramipexole) to the human $D_3$ receptor.

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

As used herein, the terms "$D_3$ ligand" or "$D_3$ receptor ligand" are used interchangeably.

As used herein, the terms "treat," "treating," "treatment," and the like refer to eliminating, reducing, or ameliorating a disease or condition and/or symptoms associated therewith. Although not precluded, treating a disease or condition does not require that the disease, condition or symptoms associated therewith be completely eliminated. The term "treat" and synonyms contemplate administering a compound of the invention to an individual in need of such treatment.

Within the meaning of the invention, "treatment" also includes the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the invention, to efficaciously deliver the agents for the treatment of condition or disease of interest to an individual in need thereof.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration" and similar phrases mean that a composition comprising two or more agents are administered concurrently to the subject being treated. By "concurrently," it is meant that each agent is administered simultaneously or sequentially in any order at different points in time. However, if not administered simultaneously, they are, in one aspect, administered sufficiently closely in time so as to provide the desired treatment effect of the combination of agents. Suitable dosing intervals and dosing order of the agents will be readily apparent to those skilled in the art. It also is contemplated that two or more agents are administered from separate compositions, and in one aspect, one composition is administered prior to administration of the other composition. Prior administration refers to administration of the agents within one day (24 hours). It is further contemplated that one agent is administered subsequent to administration of the other agent. Subsequent administration is meant to describe administration from 30 minutes of the second agent up to one day (24 hours) after administration of the first agent. Within 24 hours may include administration after 30 minutes, 1, 2, 3, 4, 5, 6, 7, 8, 9, 10, 11, 12, 16, 20, or 24 hours.

The use of the terms "a", "an", "the", and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illustrate the invention and is not a limitation on the scope of the invention unless otherwise claimed. No language in the specification should be construed as indicating any non-claimed element as essential to the practice of the invention.

The present invention is directed to potent and selective ligands for the $D_3$ receptor ligand having a structural formula (I):

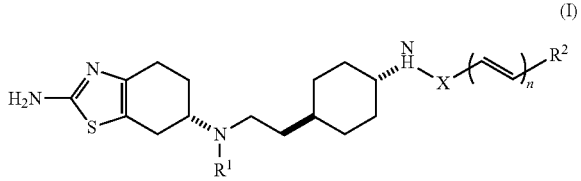

wherein X is C=O or $SO_2$; $R^1$ is $C_{1-6}$ alkyl, $R^2$ is aryl, heteroaryl, aryl, —$(CH_2)_{1-3}$aryl, or —$(CH_2)_{1-3}$heteroaryl, and n is 0 or 1, or a pharmaceutically acceptable salt, solvate, or hydrate thereof. The compounds of structural formula (I) modulate $D_3$ receptors and are useful in the treatment of a variety of diseases and conditions.

In particular, the compounds of structural formula (I) are used in methods of treating a disease or condition wherein modulation of the D3 receptor provides a benefit, for example drug (e.g., cocaine) abuse, depression, anxiety, schizophrenia, Tourette's syndrome, eating disorders, alcoholism, restless leg syndrome, Parkinson's disease, obsessive compulsive disorder, and chronic pain. The method comprises administering a therapeutically effective amount of a compound of structural formula (I) to an individual in need thereof. The present methods also encompass administering a second therapeutic agent to the individual in addition to the compound of structural formula (I). The second therapeutic agent is selected from drugs known as useful in treating the disease or condition afflicting the individual in need thereof.

As used herein, the term "alkyl" refers to straight chained and branched saturated $C_{1-6}$ hydrocarbon groups, nonlimiting examples of which include methyl, ethyl, and straight chain and branched propyl, butyl, pentyl, and hexyl groups.

As used herein, the term "halo" means fluoro, chloro, bromo, and iodo.

As used herein, groups such as

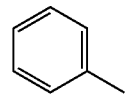

is an abbreviation for

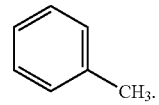

As used herein, groups such as $C_{1-3}$alkylphenyl means a $C_{1-3}$alkyl group bonded to a phenyl ring, for example,

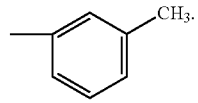

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four, groups independently selected from, for example, halo, alkyl, alkenyl, —$OCF_3$, —$NO_2$, —CN, —NC, —OH, alkoxy (—Oalkyl), amino (—$NR^2$, wherein each R, independently, is hydrogen, alkyl, aryl, or heteroaryl), —$CO_2H$, —$CO_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, —OCF$_3$, —NO$_2$, —CN, —NC, —OH, alkoxy, amino, —CO$_2$H, —CO$_2$alkyl, aryl, and heteroaryl. Examples of heteroaryl groups include, but are not limited to, thienyl, furyl, oxazolyl, quinolyl, thiophenyl, isoquinolyl, indolyl, triazinyl, triazolyl, isothiazolyl, isoxazolyl, imidazolyl, benzothiazolyl, pyrimidinyl, thiazolyl, thiadiazolyl, pyridinyl, pyridazinyl, pyrazolyl, pyrazinyl, quinolyl, tetrazolyl, oxazolyl, pyrrolyl, benzimidazolyl, benzofuranyl, cinnolinyl, indazolyl, indolizinyl, phthalazinyl, triazinyl, isoindolyl, purinyl, oxadiazolyl, furazanyl, benzofurazanyl, benzothiophenyl, benzotriazolyl, benzothiazolyl, benzisothiazolyl, benzoxazolyl, benzisoxazolyl, benzimidazolyl, quinazolinyl, quinoxalinyl, napththyridinyl, dihydroquinolyl, tetrahydroquinolyl, dihydroisoquinolyl, tetrahydroisoquinolyl, benzofuryl, furopyridinyl, pyrrolopyrimidinyl, and azaindolyl.

As used herein, the term "C$_{3-8}$cycloalkyl" means a monocyclic aliphatic ring containing three to eight carbon atoms.

As used herein, the term "heterocycloalkyl" means a monocyclic or a bicyclic aliphatic ring containing 5 to 10 total atoms, of which one to five of the atoms are independently selected from nitrogen, oxygen, and sulfur and the remaining atoms are carbon.

Additionally, salts, hydrates, and solvates of the compounds disclosed herein also are included in the present disclosure and can be used in the methods disclosed herein. For example, an acid salt of a compound of structural formula (I) can be obtained, by reacting the compound with a suitable organic or inorganic acid, such as hydrogen chloride, hydrogen bromide, acetic acid, perchloric acid, and the like. Examples of such salts include, but are not limited to, hydrochlorides, hydrobromides, sulfates, methanesulfonates, nitrates, maleates, acetates, citrates, fumarates, tartrates, bisulfates, phosphates, besylates, malates, gluconates, saccharates, pamoates, succinates, benzoates and salts of amino acids such as glutamic acid.

In some embodiments, compound of structural formula (I) contains an X that is carbonyl (C=O) and n is 0 or 1. In other embodiments, X is SO$_2$ and n is 0 or 1, and preferably is 0.

Accordingly, in preferred embodiments, a compound of structural formula (I), wherein X is C=O or SO$_2$, and n is 0 or 1 as shown, has a

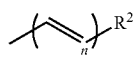

group selected from the group consisting of:

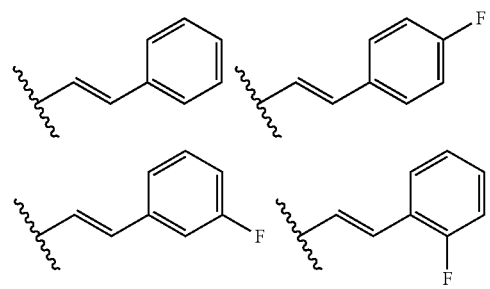

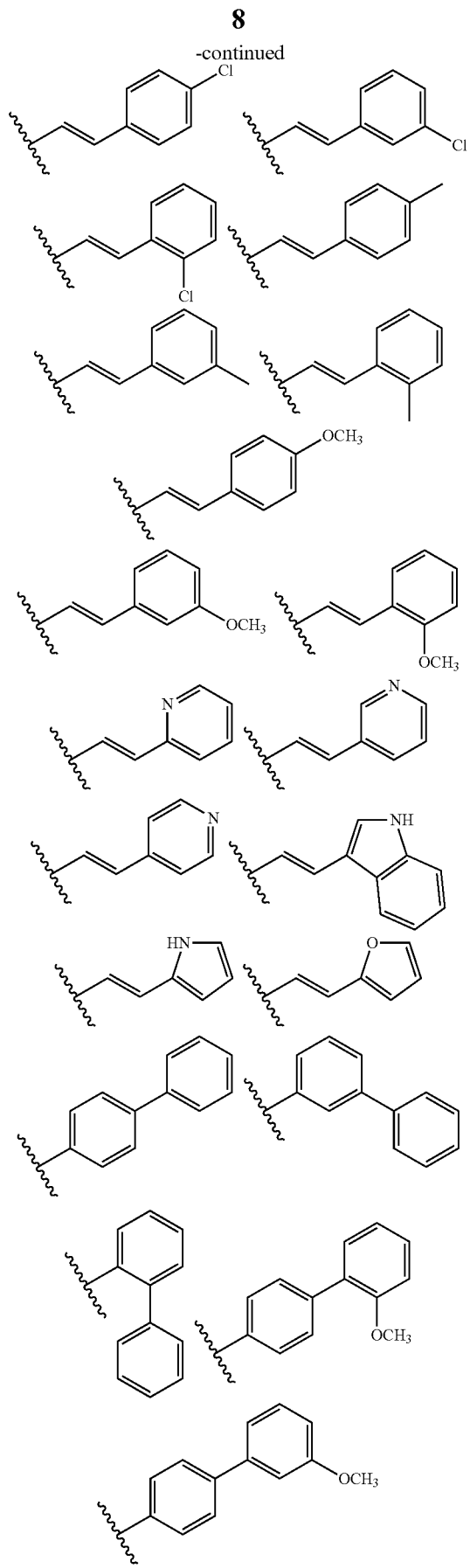

-continued
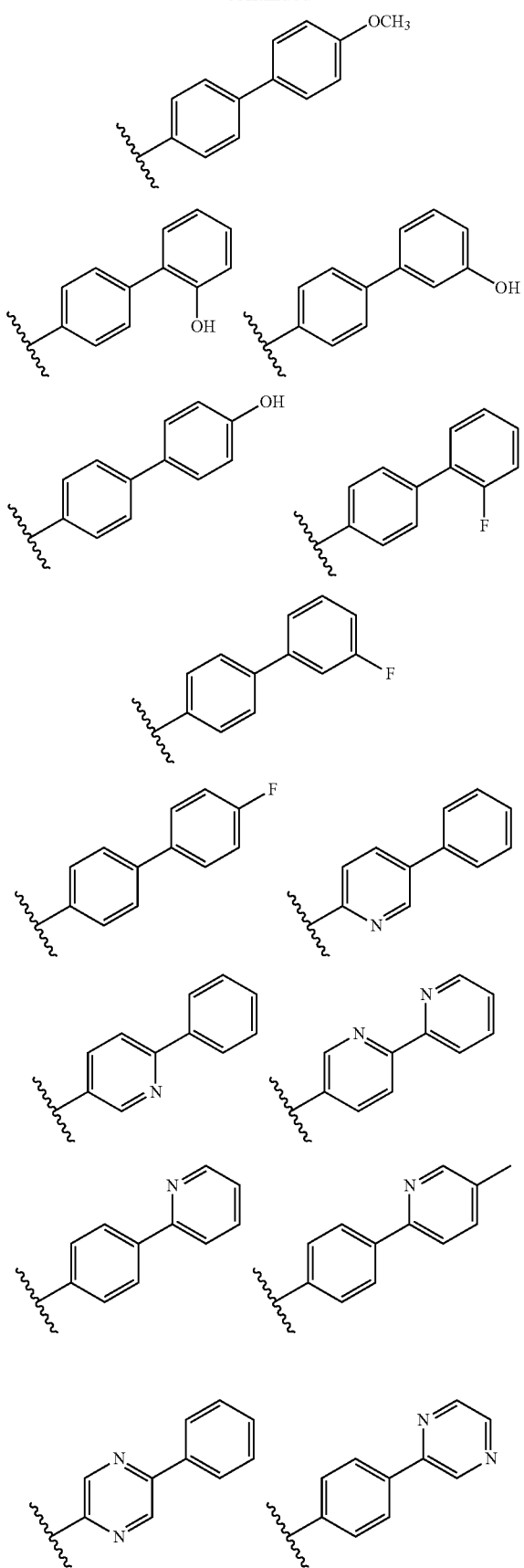
-continued
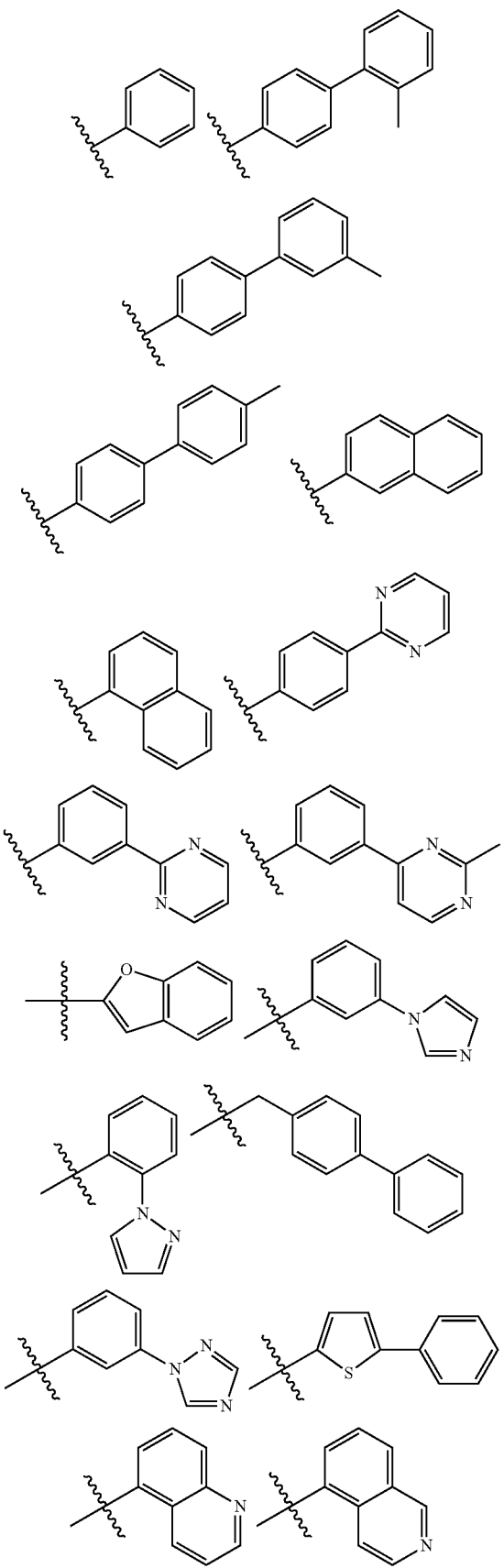

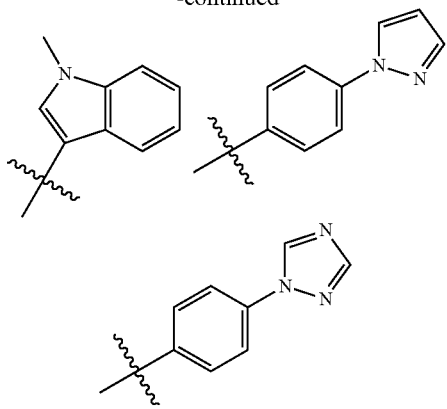
Additional R² groups are disclosed in Appendix A, which constitutes a portion of the present disclosure.
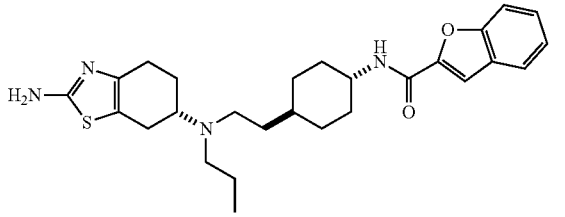
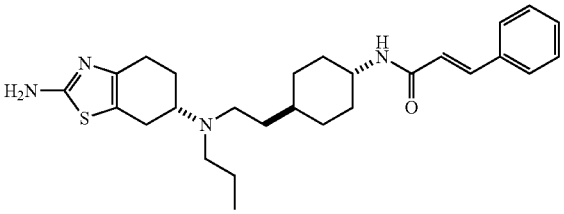
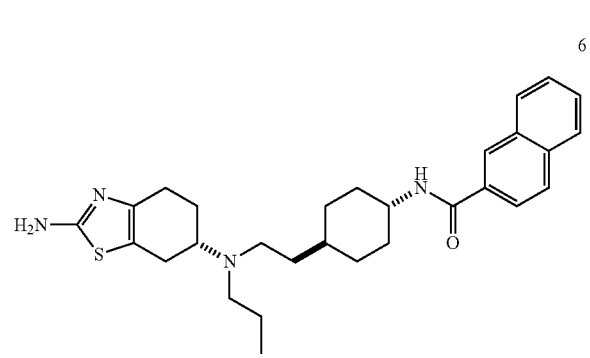
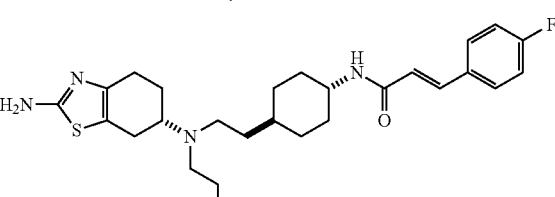
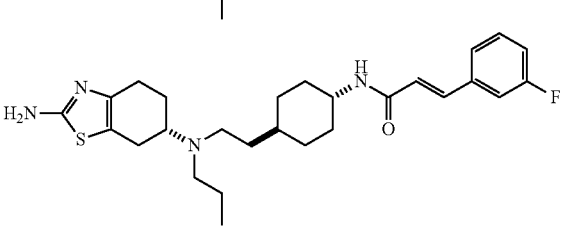
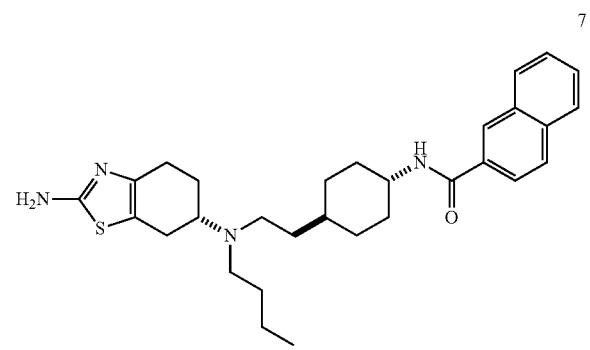
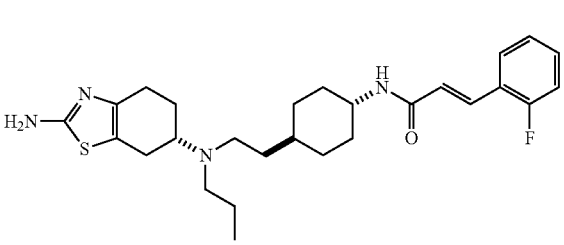
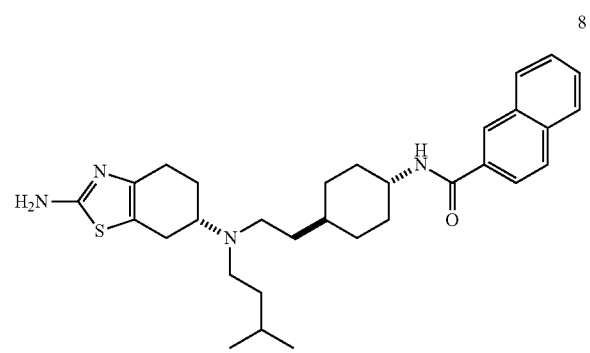
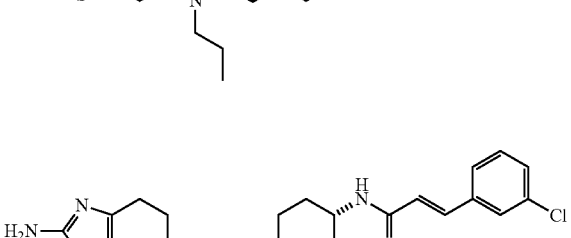

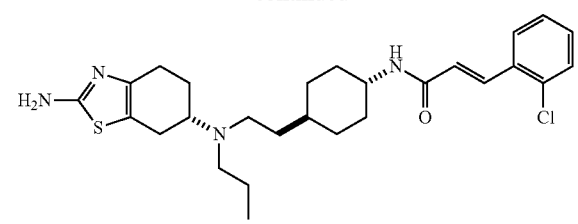
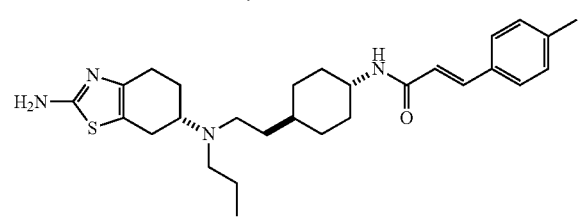
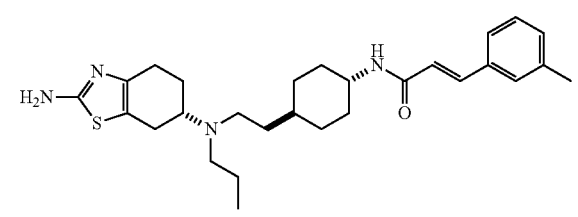
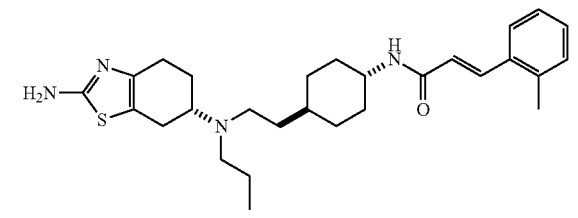
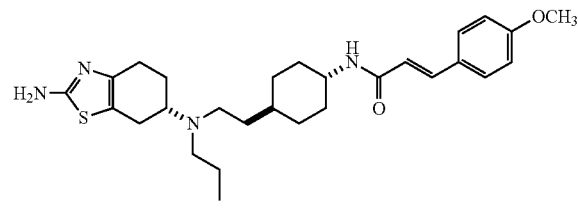
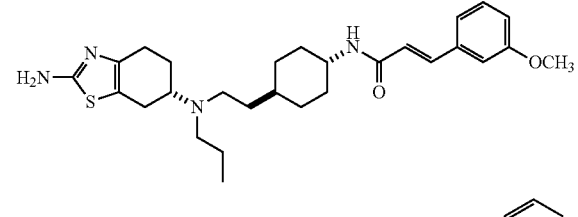
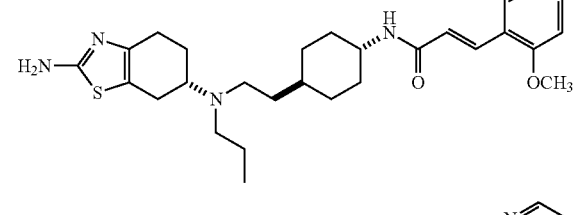
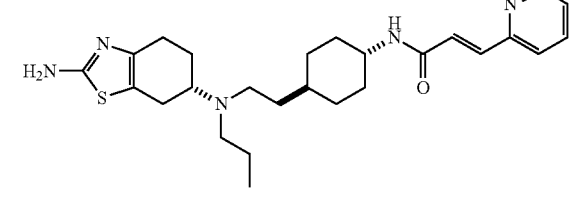
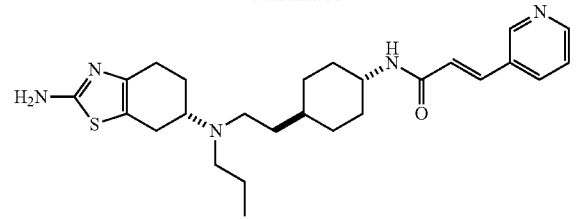
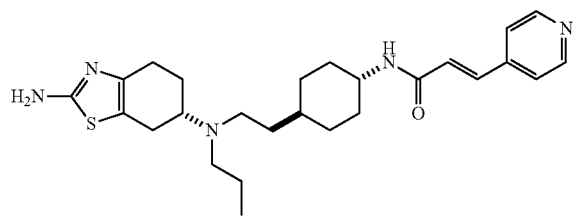
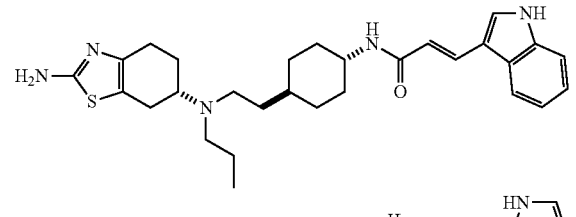
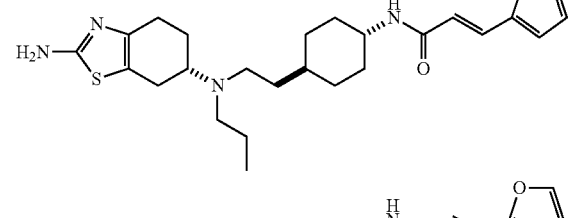
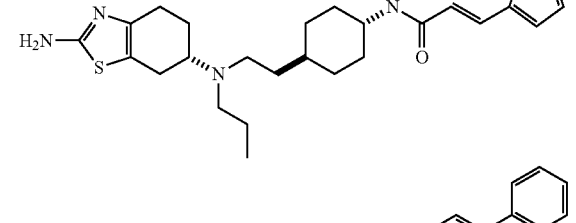
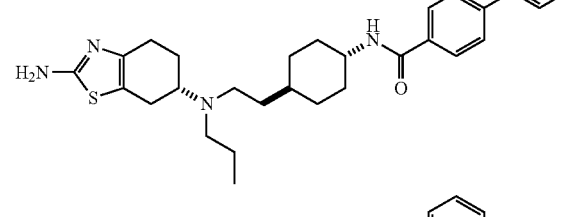
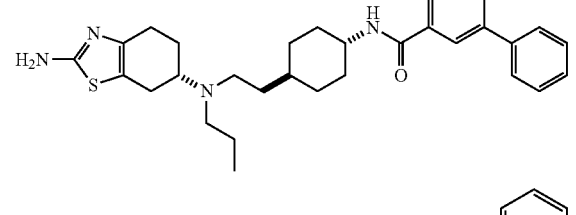
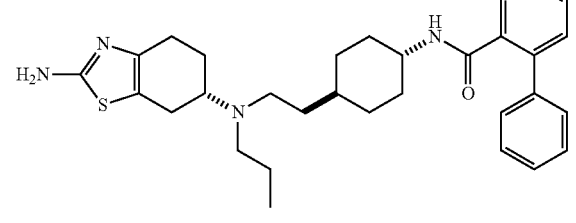

-continued
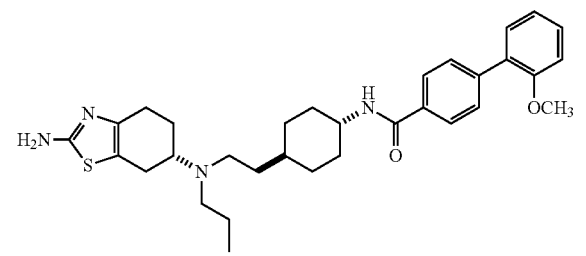
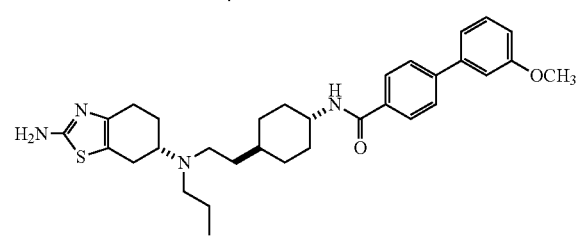
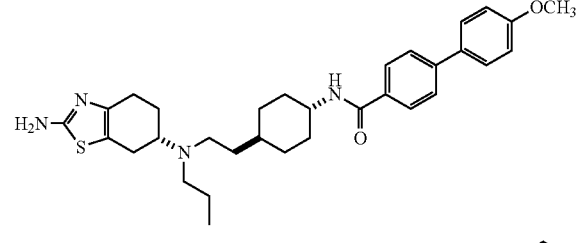
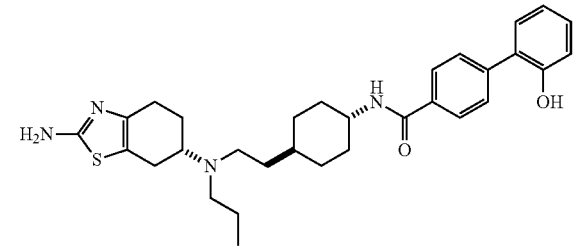
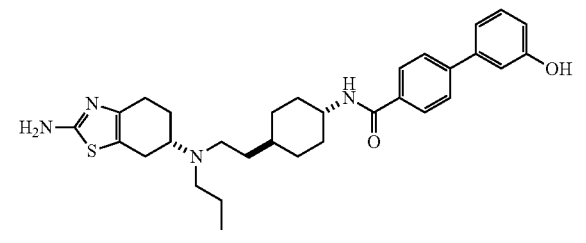
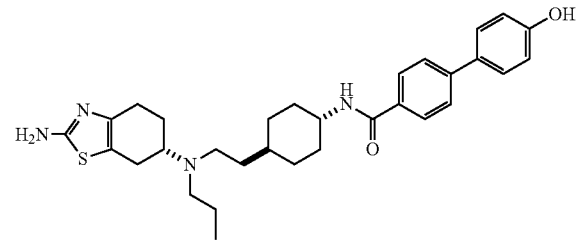
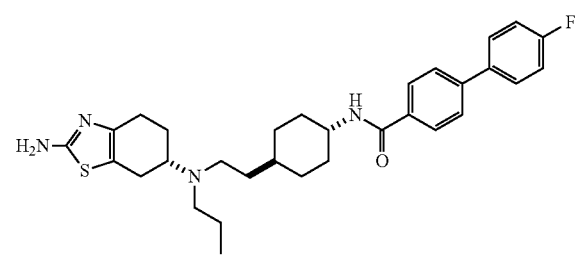
-continued
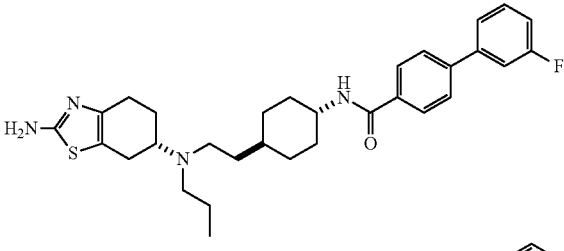
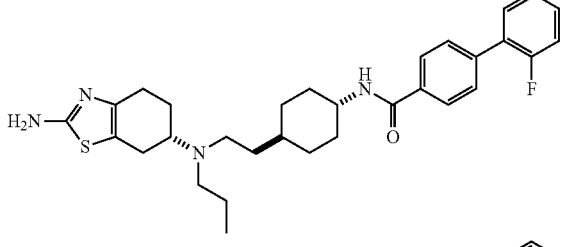
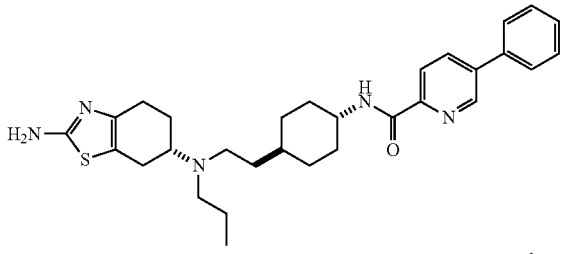
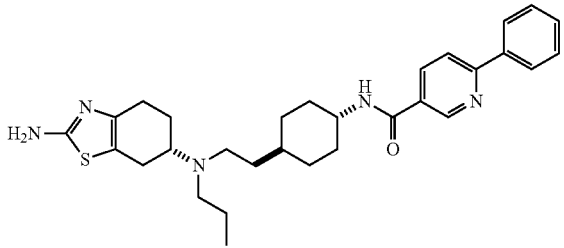
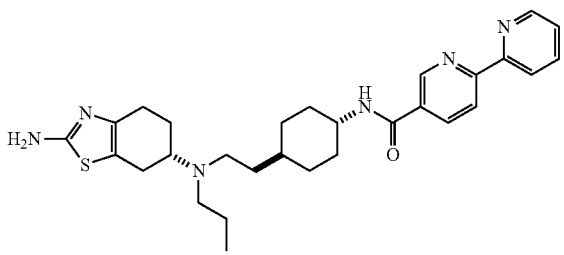
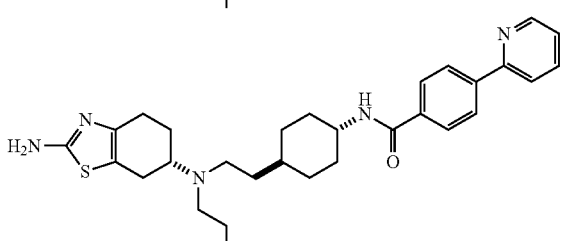
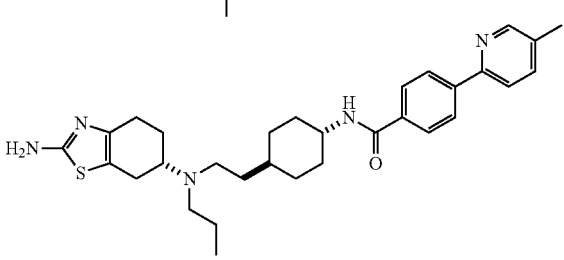

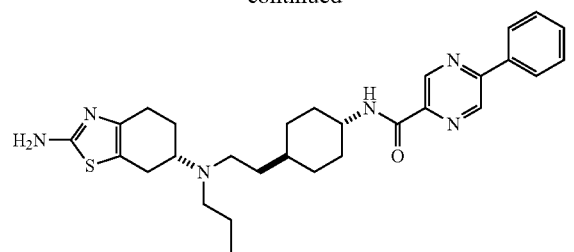
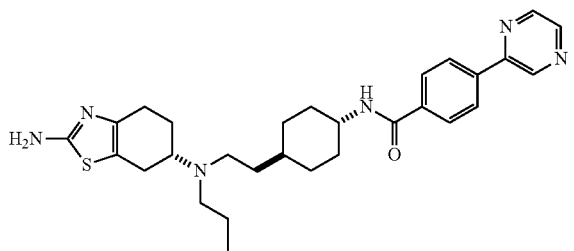
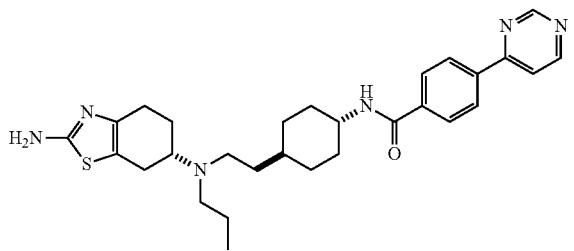
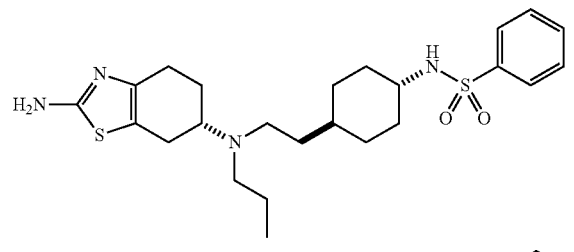
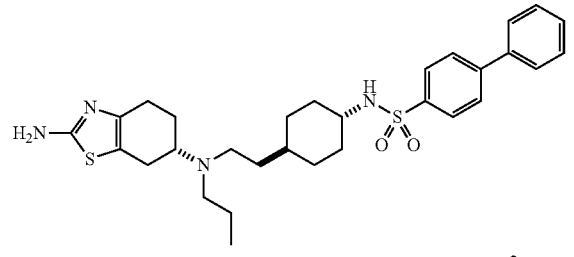
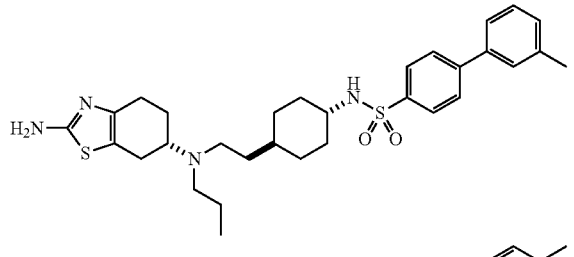
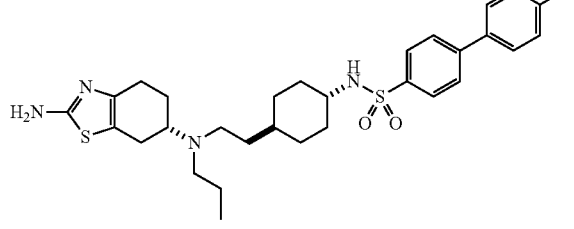
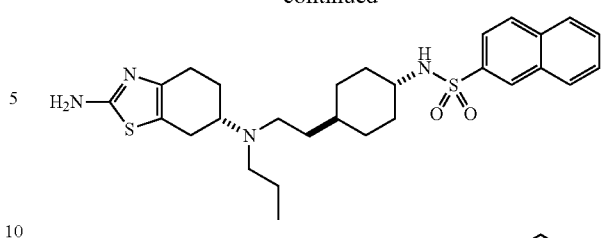
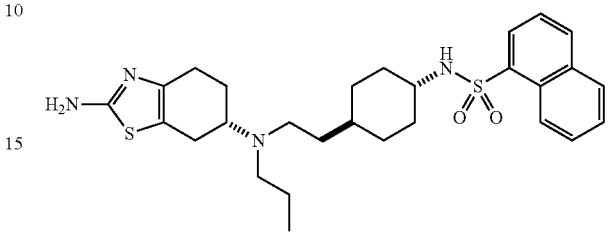
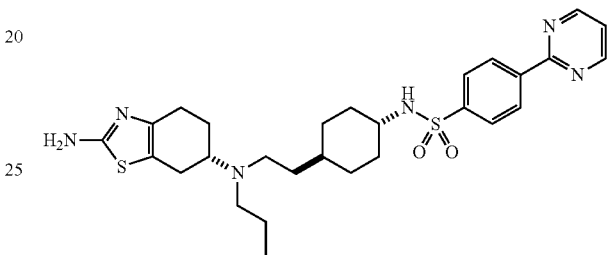
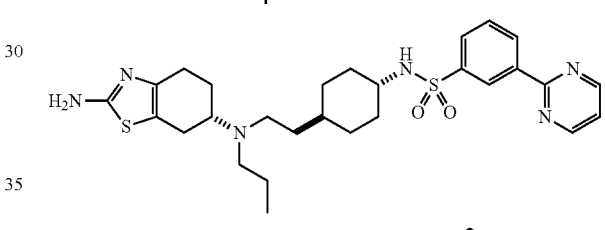
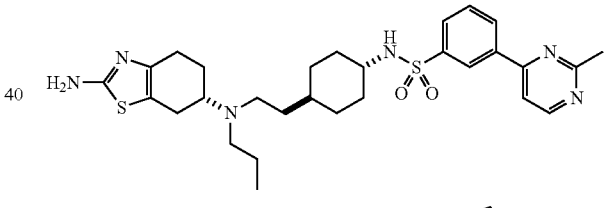
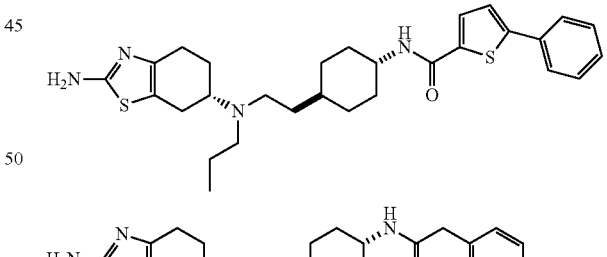
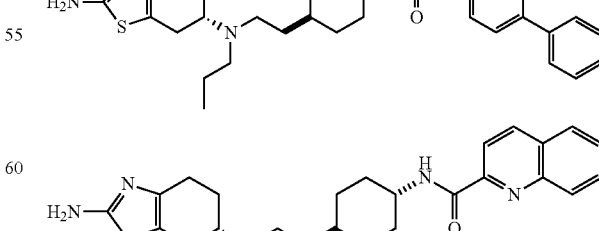
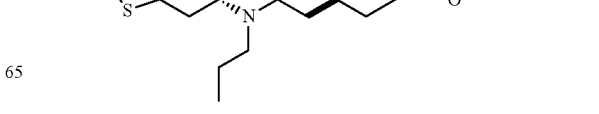

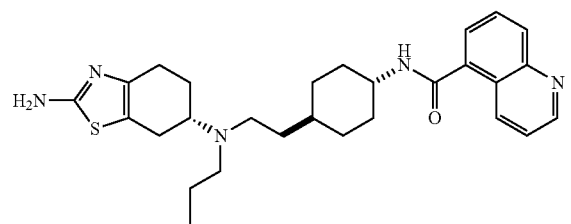

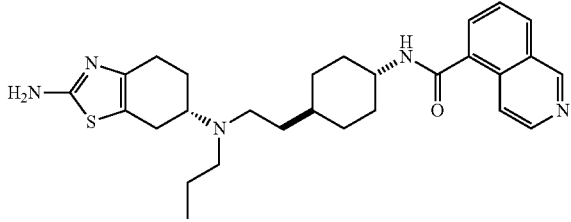

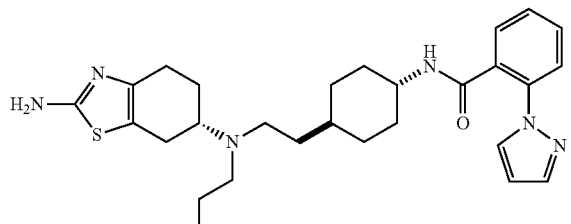

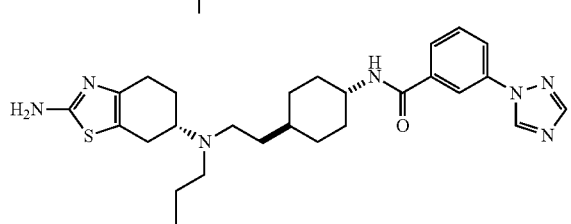

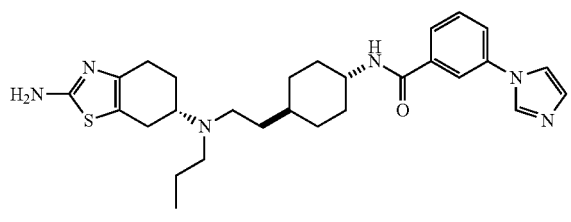

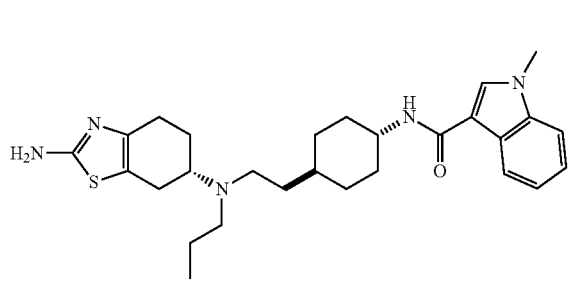

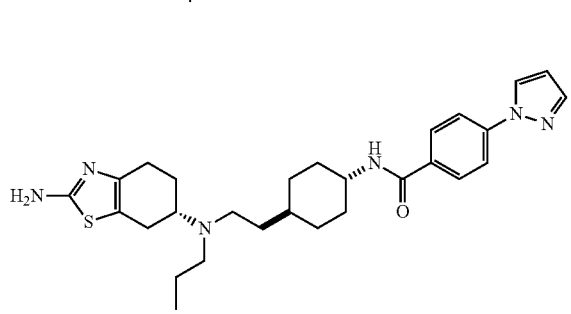

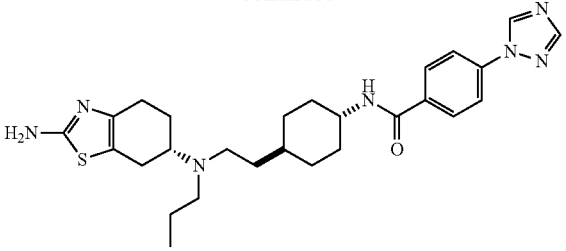

In one embodiment, the present invention discloses a method of treating an individual suffering from a disease or condition wherein modulation of the D3 receptor provides a benefit comprising administering a therapeutically effective amount of a compound of structural formula (I) to an individual in need thereof.

The methods described herein relate to the use of a compound of structural formula (I) and an optional second therapeutic agent useful in the treatment of diseases and conditions wherein modulation of the $D_3$ receptor provides a benefit. The method of the present invention can be accomplished by administering a compound of structural formula (I) as the neat compound or as a pharmaceutical composition. Administration of the pharmaceutical composition, or neat compound of structural formula (I), can be performed during or after the onset of the disease or condition of interest. Typically, the pharmaceutical compositions are sterile, and contain no toxic, carcinogenic, or mutagenic compounds that would cause an adverse reaction when administered.

A compound of structural formula (I) also can be administered in conjunction with a second therapeutic agent useful in the treatment of a disease or condition wherein modulation of the $D_3$ receptor provides a benefit. The second therapeutic agent is different from the compound of structural formula (I). A compound of structural formula (I) and the second therapeutic agent can be administered simultaneously or sequentially. In addition, the compound of structural formula (I) and second therapeutic agent can be administered from a single composition or two separate compositions. A compound of structural formula (I) and the optional second therapeutic agent can be administered simultaneously or sequentially to achieve the desired effect.

The second therapeutic agent is administered in an amount to provide its desired therapeutic effect. The effective dosage range for each second therapeutic agent is known in the art, and the second therapeutic agent is administered to an individual in need thereof within such established ranges.

The present invention therefore is directed to compositions and methods of treating diseases or conditions wherein modulation of the $D_3$ receptor provides a benefit. The present invention also is directed to pharmaceutical compositions comprising a compound of structural formula (I) and a second therapeutic agent useful in the treatment of diseases and conditions wherein modulation of the $D_3$ receptor provides a benefit. Further provided are kits comprising a compound of structural formula (I) and, optionally, a second therapeutic agent useful in the treatment of diseases and conditions wherein modulation of the $D_3$ receptor provides a benefit, packaged separately or together, and an insert having instructions for using these active agents.

As demonstrated below, a compound of structural formula (I) is a potent and selective ligand for the $D_3$ receptor and can be used in treating diseases and conditions, like drug abuse and restless leg syndrome, where modulation of the $D_3$ receptor provides a benefit.

A compound of structural formula (I) used in a method of the present invention can be administered in an amount of about 0.005 to about 500 milligrams per dose, about 0.05 to about 250 milligrams per dose, or about 0.5 to about 100 milligrams per dose. For example, a compound of structural formula (I) can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

A compound of structural formula (I) can be formulated in suitable excipients for oral administration or for parenteral administration. Such excipients are well known in the art. A compound of structural formula (I) typically is present in such a composition in an amount of about 0.1% to about 75% by weight of the composition.

A compound of structural formula (I) and the second therapeutic agent can be administered together as a single-unit dose or separately as multi-unit doses, wherein the compound of structural formula (I) is administered before the second therapeutic agent or vice versa. One or more dose of the compound of structural formula (I) and/or one or more dose of the second therapeutic agent can be administered.

The compounds of structural formula (I) therefore can be used in conjunction with one or more second therapeutic agents, for example, but not limited to, antipsychotic agents (e.g., clozapine, olanzapine, quetiapine, risperidone, ziprasidone, haloperidol, and aripiprazole), antidepressant agents, such as tricyclic antidepressants (e.g., amitriptyline, dothiepin, doxepin, trimipramine, butriptyline, clomipramine, desipramine, imipramine, iprindole, lofepramine, nortriptyline, and protriptyline), monoamine oxidase inhibitors (e.g., isocarboxazid, phenelzine, and tranylcypromine), 5-HT reuptake inhibitors (e.g., fluvoxamine, sertraline, fluoxetine, and paroxetine), serotonin-1 B antagonists (e.g., elzasonan), serotonin-2A antagonists (e.g., eplivanserin and MDL-100907), histamine-3 antagonists or agonists (e.g., cipralisant, ABT239, TISQ, and GSK-189254A) and/or with antiparkinsonian agents such as dopaminergic antiparkinsonian agents (e.g., levodopa, preferably in combination with a peripheral decarboxylase inhibitor e.g., benserazide or carbidopa, or with a dopamine agonist, e.g., bromocriptine, lysuride, and pergolide).

The compounds of structural formula (I) are highly selective dopamine $D_3$ receptor ligands which, because of their low affinity for other receptors such as dopamine $D_1$ and $D_2$, give rise to fewer side effects than compounds that are non-selective $D_2/D_3$ ligands (agonists, partial agonists, antagonists, or inverse agonists). Compounds of the present invention can be selective agonists, partial agonists, antagonists or inverse agonists for the D3 receptor over other dopamine receptors.

The present invention provides a selective $D_3$ ligand, as exemplified by compounds of structural formula (I), for the treatment of a variety of diseases and conditions, in which selective modulation of the $D_3$ receptor has a beneficial effect. Preferably, a compound of structural formula (I) is selective for the $D_3$ receptor over the $D_2$ receptor by a factor of at least 100, and over the $D_1$ receptor by a factor of at least 1000.

Conditions and diseases of the central nervous system (CNS) are understood as meaning disorders which affect the spinal chord and, in particular, the brain. Within the meaning of the present invention, the term "disease" or "condition" denote disturbances and/or anomalies that as a rule are regarded as being pathological conditions or functions, and that can manifest themselves in the form of particular signs, symptoms, and/or malfunctions. The treatment methods according to the invention can be directed toward individual disorders, i.e. anomalies or pathological conditions, but it also is possible to treat several anomalies that may be causatively linked to each other to be combined into patterns, i.e., syndromes.

The diseases and conditions that can be treated in accordance to the invention include, for example, psychiatric and neurological disturbances. These diseases and conditions include, for example, organic disturbances, including symptomatic disturbances, such as psychoses of the acute exogenous reaction type or attendant psychoses or organic or exogenous cause, e.g., in association with metabolic disturbances, infections, and endocrinopathologies; endogenous psychoses, such as schizophrenia and schizotype and delusional disturbances; affective disturbances, such as depressions, mania, and/or manic-depressive conditions; and also mixed forms of the above described diseases and conditions; neurotic and somatoform disturbances and disturbances in association with stress; dissociative disturbances, e.g., loss of consciousness, clouding of consciousness, double consciousness, and personality disturbances; disturbances in attention and waking and/or sleeping behavior, such as behavioral disturbances and emotional disturbances whose onset lies in childhood and youth, e.g., hyperactivity in children, intellectual deficits, in particular, attention disturbances (attention deficit disorders), memory disturbances and cognitive disturbances, e.g., impaired learning and memory (impaired cognitive function), dementia, narcolepsy, and sleep disturbances, e.g., restless leg syndrome; developmental disturbances; anxiety states, delirium, sex-life disturbances, e.g., impotence in men; eating disturbances, e.g., anorexia or bulimia, addiction, and other unspecified disturbances.

The disorders which can be treated in accordance with the invention also include Parkinson's disease and epilepsy, and, in particular, affective disturbances connected thereto.

The addiction diseases include psychic disorders and behavioral disturbances which are caused by the abuse of psychotropic substances, such as pharmaceuticals or narcotics and also other addiction diseases, such as addiction to gaming (impulse control disorders not elsewhere classified). Examples of addictive substances are opioids (e.g., morphine, heroin, and codeine), cocaine, nicotine, alcohol, substances which interact with GABA chloride channel complex, sedatives, hypnotics, and tranquilizers, for example, benzodiazepines; LSD; cannabinoids; psychomotor stimulants, such as 3,4-methylenedioxy-N-methylamphetamine (i.e., ecstasy), amphetamine and amphetamine-like substances, such as methylphenidate and other stimulants including caffeine. Addictive substances of particular consideration are opioids, cocaine, amphetamine or amphetamine-like substances, nicotine, and alcohol.

With regard to the treatment of addiction diseases, particular preference is given to compounds of structural formula (I) that do not possess a psychotropic effect. This can be observed in a test using rats which, after having been administered a compound of the invention, reduce their self-administration of a psychotropic substance, for example, cocaine.

According to another embodiment of the present invention, the compounds of structural formula (I) are suitable for treating conditions and diseases whose cause can be at least partially attributed to an anomalous activity of dopamine $D_3$ receptors.

According to another embodiment of the present invention, the treatment is directed toward conditions and diseases that can be influenced by the binding of exogenously administered ligands to dopamine $D_3$ receptors.

The diseases and conditions that can be treated with a compounds of the present invention frequently are characterized by progressive development, i.e., the above-described conditions change over the course of time, and, as a rule, the severity increases and conditions possibly can merge into one another, or other conditions appear in addition to those which already exist can appear.

The compounds according to the invention can be used to treat a large number of signs, symptoms, and/or malfunctions that are connected to disease and condition of the central nervous system and, in particular, the abovementioned diseases and conditions. These signs, symptoms, and/or malfunctions include, for example, a disturbed relationship to reality, lack of insight, and ability to meet customary social norms or the demands made by life, changes in temperament, changes in individual drives, such as hunger, sleep, and thirst, for example, and mood, disturbances in the ability to observe and combine, changes in personality, in particular emotional lability, hallucinations, ego-disturbances, distractedness, ambivalence, autism, depersonalization, and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g., peripheral positional, rotational and oscillatory vertigo, melancholia, hysteria, hypochondria, and the like.

Therefore, compounds of the present invention are suitable for treatment of diseases of the central nervous system, in particular for treating affective disorders; neurotic disturbances, stress disturbances and somatoform disturbances and psychoses and, in particular, for treating schizophrenia and depression. Because of their high selectivity with regard to the $D_3$ receptor, the compounds of structural formula (I) also are suitable for treating disturbances of kidney function which are caused by diabetes mellitus (see WO 00/67847 incorporated herein by reference) and, especially, diabetic nephropathy.

In the present method, a therapeutically effective amount of one or more compound (I), as a rule formulated in accordance with pharmaceutical practice, is administered to a human being in need thereof. Whether such a treatment is indicated, depends on the individual case and is subject to medical assessment (diagnosis) that takes into consideration signs, symptoms, and/or malfunctions which are present, the risks of developing particular signs, symptoms and/or malfunctions, and other factors.

A compound of structural formula (I) can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

The pharmaceutical compositions include those wherein a compound of structural formula (I) is administered in an effective amount to achieve its intended purpose. Determination of a therapeutically effective amount is well within the capability of those skilled in the art, especially in light of the detailed disclosure provided herein.

The exact formulation, route of administration, and dosage is determined by an individual physician in view of the diagnosed condition or disease. Dosage amount and interval can be adjusted individually to provide levels of a compound of structural formula (I) that is sufficient to maintain therapeutic effects. The amount of pharmaceutical composition administered is dependent on the subject being treated, on the subject's weight, the severity of the affliction, the manner of administration, and the judgment of the prescribing physician.

Specifically, for administration to a human in the treatment of a disease or condition, oral dosages of a compound of structural formula (I), individually generally are about 0.005 to about 500 milligrams daily for an average adult patient (70 kg), typically one dose per day or divided into two to three doses per day. Thus, for a typical adult patient, individual doses contain about 0.005 to about 500 milligrams of compound (I), in a suitable pharmaceutically acceptable vehicle or carrier, for administration in single or multiple doses, once or several times per day. Dosages for intravenous, buccal, or sublingual administration typically are about 0.005 to about 250 milligrams/kg per single dose as required. In practice, the physician determines the actual dosing regimen that is most suitable for an individual patient, and the dosage varies with the age, weight, and response of the particular patient. The above dosages are exemplary of the average case, but there can be individual instances in which higher or lower dosages are merited, and such are within the scope of this invention.

The compounds of the present invention can be administered alone, or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the compounds of structural formula (I) into preparations that can be used pharmaceutically.

These pharmaceutical compositions can be manufactured in a conventional manner, e.g., by conventional mixing, dissolving, granulating, dragee-making, emulsifying, encapsulating, entrapping, or lyophilizing processes. Proper formulation is dependent upon the route of administration chosen. When a therapeutically effective amount of the compound of structural formula (I) is administered orally, the composition typically is in the of a tablet, capsule, powder, solution, or elixir. When administered in tablet form, the composition additionally can contain a solid carrier, such as a gelatin or an adjuvant. The tablet, capsule, and powder contain about 1% to about 95%, and preferably from about 1% to about 50%, of a compound of structural formula (I). When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of structural formula (I).

When a therapeutically effective amount of a compound of structural formula (I) is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle. A compound of structural formula (I) can be infused with other fluids over a 10-30 minute span or over several hours.

Compounds of structural formula (I) can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the compound of structural formula (I) to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A compound of structural formula (I) can be formulated for parenteral administration by injection, e.g., by bolus injection or continuous infusion. Formulations for injection can be presented in unit dosage fowl, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a compound of structural formula (I) can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A compound of structural formula (I) also can be formulated in rectal compositions, such as suppositories or retention enemas, e.g., containing conventional suppository bases. In addition to the formulations described previously, the compound of structural formula (I) also can be formulated as a depot preparation. Such long-acting formulations can be administered by implantation (for example, subcutaneously or intramuscularly) or by intramuscular injection. Thus, for example, the compounds of structural formula (I) can be formulated with suitable polymeric or hydrophobic materials (for example, as an emulsion in an acceptable oil) or ion exchange resins.

In particular, the compounds of structural formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The compounds of structural formula (I) also can be injected parenterally, for example, intravenously, intramuscularly, subcutaneously, or intracoronarily. For parenteral administration, the endothelin antagonists are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a compound of structural formula (I) and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

As discussed above, prior $D_3$ ligands suffered from a low selectivity for the $D_3$ receptor and/or possessed physical properties, e.g., a low water solubility that hindered development as therapeutic agents. One $D_3$ receptor ligand approved for the treatment of Parkinson's disease and restless leg syndrome is pramipexole hydrochloride (compound 1). Compound 1 is a very potent $D_3$ ligand and has a $K_i$ value of 0.78 nM to $D_3$ (see Table 1 below). Compound 1 also has an excellent aqueous solubility and an excellent pharmacological and toxicological profile in humans and in animals. Although compound 1 has been widely used as a $D_3$ preferring ligand, it also binds potentially to the high affinity state of the $D_2$ receptor with a $K_i$ value of 3.1 nM (Table 1), thus displaying only a 4-fold selectivity for the $D_3$ receptor over the $D_2$ receptor.

In accordance with an important feature of the present invention, compounds of structural formula (I) were synthesized and evaluated as ligands for the dopamine 3 ($D_3$) receptor. For example, compound 12 described below has a $K_i$ value of 0.41 nM to $D_3$ and a selectivity of >30,000 and 800-fold over the $D_1$-like and $D_2$ receptors, respectively. In vivo functional assays show that compound 12 is a partial agonist at the $D_3$ receptor with no detectable activity at the $D_2$ receptor.

Synthesis of Compounds

Compounds of the present invention and comparative compounds were prepared as follows.

Solvents and reagents were obtained commercially and used without further purification. Reactions were monitored by TLC carried performed on 250 μm E. Merck silica gel plates (60E-254) using UV light as a visualizing agent. E. Merck silica gel (60, particle size 15-40 μm) was used for flash column chromatography. NMR spectra were recorded on a Bruker Avance300 spectrometer (300 MHz). Chemical shifts (δ) are reported as δ values (ppm) downfield relative to TMS as an internal standard, with multiplicities reported in the usual manner. High resolution electrospray ionization mass spectra (MS) were run on a Micromass AutoSpec Ultima mass spectrometer. Elemental analysis (EA) was performed using a Perkin-Elmer 2400 Series II Analyzer. HPLC analysis was performed on a Waters 2795 using a Waters SunFire C18 (150 mm×4.6 mm) column, mobile phase flow 1.0 mL/min, gradient water (with 0.1% TFA)/acetonitrile (with 0.1% TEA) 0~50%, and UV detection at 254 nm.

The synthesis of compound 5 (comparative) is outlined in Scheme 1. Briefly, commercially available pramipexole (compound 1), purchased from APAC Pharmaceutical Co., USA, was treated with N-(4-bromobutyl)-phthalimide in the presence of cesium carbonate ($Cs_2CO_3$) in acetonitrile to afford amine 13. Compound 13 was treated with hydrazine to remove the phthalimide protective group to give the amine 14, followed by reaction with 2-naphthoyl chloride to provide compound 5.

Scheme 1. Synthetic route for compound 5.

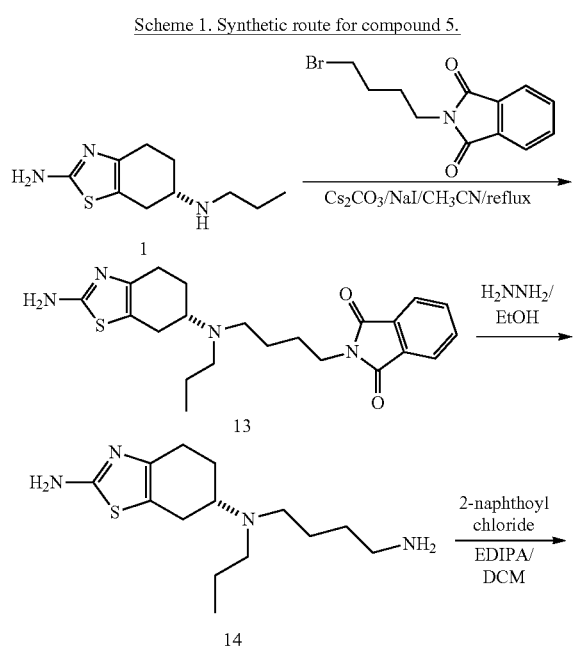

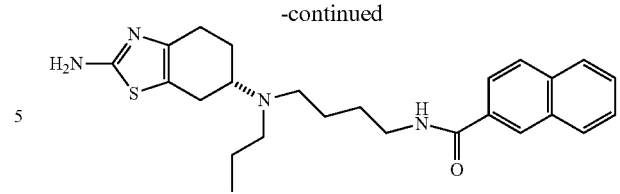

The syntheses of compounds 6-10 is shown in Scheme 2. The carboxylic acid group in compound 15 was reduced to alcohol 16 by borane. Compound 16 was treated with tetrabromomethane and triphenylphosphione in dichloromethane to give bromide 17. Deprotection of Boc protective group, followed by 2-naphthyl chloride treatment afforded bromide 18. (6S)-4,5,6,7-Tetrahydro-1,3-benzothiazol-2,6-diamine (19) was reacted with the bromide 18 in the presence of $Cs_2CO_3$ and sodium iodide (NaI) in acetonitrile to give compound 10, which also was used as the key intermediate for the synthesis of compounds 6-9. Compound 10 was treated with different bromides and the products purified by chromatography to afford desired compounds 6-9.

Scheme 2. Synthesis of compounds 6-10.

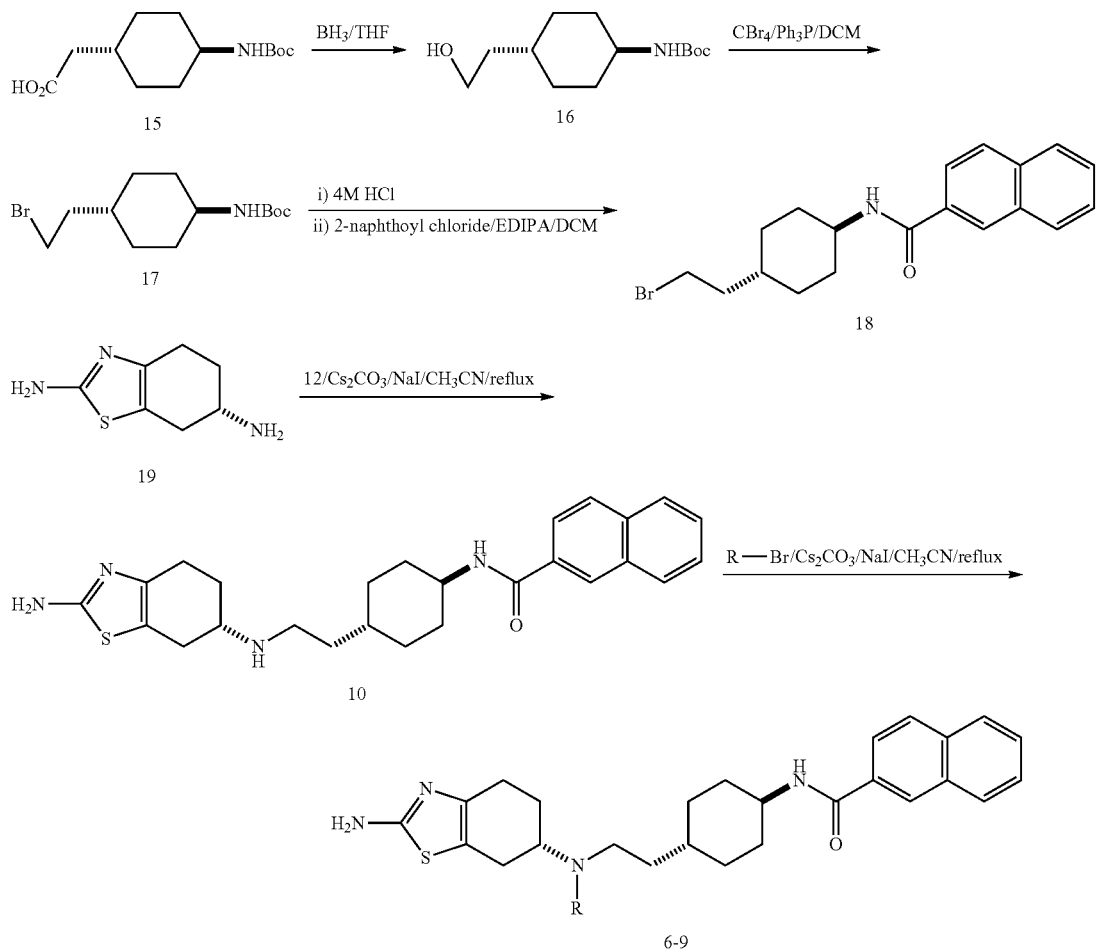

The synthesis of compounds 11 and 12 is outlined in Scheme 3. Briefly, (6S)-4,5,6,7-tetrahydro-1,3-benzothiazol-2,6-diamine (19) was reacted with the bromide 17 in the presence of $Cs_2CO_3$ and NaI in acetonitrile to give the key intermediate 20. Compound 15 was treated with n-propyl bromide, deprotected by 4M HCl, and condensed with benzofuran-2-carboxylic acid or cinnamic acid to give designed compound 11 or 12.

57.73, 53.11, 50.64, 40.57, 27.96, 26.99, 26.13, 25.21, 22.57, 12.31. Free base was converted into its HCl salt. Anal. Calcd for $C_{25}H_{32}N_4OS \cdot 2HCl \cdot 2H_2O$: C, 55.05; H, 7.02; N, 10.27. Found: C, 54.62; H, 7.10; N, 10.12.

Trans-tert-butyl-4-(2-hydroxyethyl)cyclohexylcarbamate (16) 1.0 M $BH_3$ (15 mL, 15 mmol) in THF was added to a solution of compound 15 (2.57 g, 10 mmol) in anhydrous THF (30 mL). The reaction mixture was stirred at 0° C. for 1

Scheme 3. Synthesis of compounds 11 and 12.

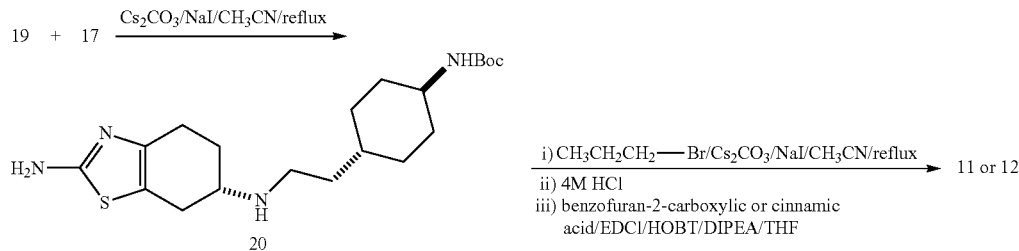

(S)-2-(4-((2-amino-4,5,6,7-tetrahydrobenzo[d]thiazol-6-yl)(propyl)amino)butyl)isoindoline-1,3-dione (13). N-(4-bromobutyl)-phthalimide (2.25 g, 7.98 mmol), cesium carbonate (2.6 g, 7.98 mmol), and sodium iodide (1.80 g, 12 mmol) were added to a solution of pramipexole 1 (1.53 g, 7.25 mmol) in acetonitrile (50 mL). After refluxing for 3 hours, the mixture was evaporated in vacuo. The residue was partitioned between ethyl acetate and water. The organic layer was separated and washed with brine, and dried over anhydrous $Na_2SO_4$. Flash column chromatography (MeOH/EtOAc, 5:95) gave 13 as a colorless oil (2.7 g, 90.4%). $^1$H NMR ($CDCl_3$, 300 MHz) δ 7.88-8.00 (m, 2H), 7.78-7.60 (m, 2H), 4.90 (s, 2H), 3.70 (t, J=7.2 Hz, 2H), 3.10-2.95 (m, 1H), 2.78-2.30 (m, 8H), 2.05-1.90 (m, 1H), 1.77-1.60 (m, 3H), 1.56-1.40 (m, 4H), 0.87 (t, J=7.2 Hz, 3H); $^{13}$C NMR ($CDCl_3$, 75 MHz) δ168.89, 165.83, 145.53, 134.28, 132.53, 123.58, 117.96, 57.59, 52.97, 50.41, 38.34, 27.01, 26.81, 26.71, 26.05, 25.33, 22.64, 12.24.

(S)—$N^6$-(4-aminobutyl)-$N^6$-propyl-4,5,6,7-tetrahydrobenzo[d]thiazole-2,6-diamine (14) Hydrazine hydrate (5 mL) was added to a solution of compound 13 (3.4 g, 8.25 mmol) in ethanol (30 mL) and the mixture was refluxed for 2 hours. The mixture was evaporated in vacuo. The residue was partitioned between ethyl acetate and water. The organic layer was separated and washed with brine, and dried over anhydrous $Na_2SO_4$. Evaporation of solvent afforded compound 14 as a colorless oil (2.32 g, 99%), which was used for the next step without further purification.

(S)—N-(4-((2-amino-4,5,6,7-tetrahydrobenzo[d]thiazol-6-yl)(propyl)amino)butyl)-2-naphthamide (5) 2-Naphthoyl chloride (0.92 g, 4.8 mmol) and DIPEA (0.62 g, 4.8 mmol) were added to a solution of compound 14 (1.13 g, 4.0 mmol) in anhydrous dichloromethane. After stirring at room temperature for 2 hours, the reaction mixture was concentrated in vacuo. The residue was purified by silica gel column chromatography (MeOH/EtOAc, 1:9) to afford compound 5 as a colorless solid (1.40 g, 80%). $^1$H NMR ($CDCl_3$, 300 MHz) δ 8.28 (s, 1H), 7.96-7.75 (m, 4H), 7.60-7.45 (m, 2H), 6.72 (t, J=5.7 Hz, 1H), 4.95 (s, 2H), 3.52 (q, J=6.2 Hz, 2H), 3.10-2.95 (m, 1H), 2.73-2.35 (m, 8H), 2.00-1.88 (m, 1H), 1.80-1.37 (m, 7H), 0.89 (t, J=7.2 Hz, 3H); $^{13}$C NMR ($CDCl_3$, 75 MHz) 168.1, 166.00, 145.46, 135.04, 133.01, 132.50, 129.26, 128.79, 128.14, 127.94, 127.67, 127.12, 124.06, 117.72, hour. The reaction was quenched with water and extracted with ethyl acetate. Solvent was removed in vacuo and the residue was purified by silica gel column chromatography (Hexane/EtOAc, 1:1) to give 16 as a colorless oil (2.40 g, 98%). $^1$H NMR ($CDCl_3$, 300 MHz) δ 4.39 (s, broad, 1H), 3.69 (t, J=6.6 Hz, 2H), 3.45-3.25 (m, 1H), 2.05-1.94 (m, 2H), 1.85-1.70 (m, 2H), 1.55-1.23 (m, 4H), 1.45 (s, 9H), 1.20-0.95 (m, 4H). $^{13}$C NMR ($CDCl_3$, 75 MHz) δ 155.67, 79.47, 61.17, 50.22, 40.03, 33.81, 33.76, 32.24, 28.83.

Trans-tert-butyl-4-(2-bromoethyl)cyclohexylcarbamate (17) Triphenylphosphine (3.9 g, 14.8 mmol) and carbon tetrabromide (4.9 g, 14.8 mmol) were added to a solution of compound 16 (3.0 g, 12.3 mmol) in dichloromethane (40 mL). The solution was stirred at 0° C. for 1 hour and room temperature for 1 hour. Solvent was removed in vacuo and the residue was purified by silica gel column chromatography (Hexane/EtOAc, 6:1) to give compound 17 as a colorless solid (3.7 g, 98%). $^1$H NMR ($CDCl_3$, 300 MHz) δ 4.5 (s, broad), 3.44 (t, J=7.0 Hz, 2H), 3.47-3.30 (m, 1H), 2.10-1.92 (m, 2H), 1.82-1.70 (m, 4H), 1.45 (s, 9H), 1.53-1.35 (m, 1H), 1.25-0.90 (m, 4H). $^{13}$C NMR ($CDCl_3$, 75 MHz) δ155.63, 79.49, 50.13, 39.92, 35.59, 33.80, 33.57, 32.17, 31.54, 31.29, 29.08, 28.83, 28.55.

Trans-N-(4-(2-bromoethyl)cyclohexyl)-2-naphthamide (18) 4.0 M HCl solution in dioxane (4.0 mL, 16.0 mmol) was added to a solution of compound 17 (1.0 g, 3.3 mmol) in dioxane (15 mL) and the reaction mixture was stirred at room temperature for 2 hours. Solvent was evaporated in vacuo and the residue was used directly for the next step without further purification. 2-Naphthoyl chloride (750 mg, 3.93 mmol) and triethylamine (707 mg, 7.0 mmol) were added to a solution of the above residue in dichloromethane (20 mL). After stirring at room temperature for 2 hours, the mixture was evaporated in vacuo. The residue was purified by silica gel column chromatography (hexane/EtOAc, 3:1) to give compound 18 as a colorless solid (0.92 g, 77% for two steps). $^1$H NMR ($CDCl_3$, 300 MHz) δ 8.29 (s, 1H), 7.98-7.80 (m, 4H), 7.65-7.50 (m, 2H), 6.15 (d, J=8.1 Hz, 1H), 4.10-3.95 (m, 1H), 3.52 (t, J=7.0 Hz, 2H), 2.30-2.15 (m, 2H), 1.97-1.80 (m, 4H), 1.65-1.48 (m, 1H), 1.43-1.10 (m, 4H); $^{13}$C NMR ($CDCl_3$, 75 MHz) δ 166.83, 134.65, 132.61, 132.12, 128.86, 128.39, 127.73, 127.55, 127.22, 126.72, 123.63, 49.08, 39.46, 35.19, 32.89, 31.79, 31.07.

Trans-N-(4-(2-((S)-2-amino-4,5,6,7-tetrahydrobenzo[d]thiazol-6-ylamino)ethyl)cyclohexyl)-2-naphthamide (10) Bromide 18 (1.18 g, 3.28 mmol), cesium carbonate (1.59 g, 4.90 mmol), and sodium iodide (0.737 g, 4.90 mmol) were added to a solution of compound 19 (0.554 g, 3.28 mmol) in acetonitrile (30 mL). After refluxing for 48 hours, the mixture was evaporated in vacuo. The residue was partitioned between ethyl acetate and water. The organic layer was separated and washed with brine, and dried over anhydrous sodium sulfate ($Na_2SO_4$). Flash column chromatography (MeOH/EtOAc, 1:6) gave compound 10 as a colorless solid (0.90 g, 61%). $^1$H NMR ($CDCl_3$, 300 MHz) δ 8.27 (s, 1H), 7.95-7.84 (m, 4H), 7.58-7.28 (m, 2H), 6.12 (d, J=8.7 Hz, 1H), 4.81 (s, 2H), 4.02-3.99 (m, 1H), 3.04-2.80 (m, 2H), 2.76-2.35 (m, 5H), 2.30-2.00 (m, 3H), 1.95-1.60 (m, 3H), 1.55-1.10 (m, 8H); $^{13}$C NMR ($CDCl_3$, 75 MHz) δ 166.76, 165.32, 145.11, 134.64, 132.63, 132.19, 128.86, 128.40, 127.74, 127.53, 127.17, 126.72, 123.59, 116.54, 54.09, 49.22, 45.05, 37.51, 35.01, 33.19, 31.88, 30.14, 29.51, 24.97; HRMS-Electrospray (m/z): [M+H]$^+$ calcd 449.2375. found 449.2369; purity HPLC 100.0%, $t_R$=29.903 min.

Trans-N-(4-(2-(((S)-2-amino-4,5,6,7-tetrahydrobenzo[d]thiazol-6-yl)(propyl)amino)ethyl)cyclohexyl)-2-naphthamide (6) n-Propyl bromide (38 mg, 0.28 mmol), cesium carbonate (108 mg, 0.33 mmol), and sodium iodide (50 mg, 0.33 mmol) were added to a solution of compound 10 (100 mg, 0.22 mmol) in acetonitrile (15 mL). After refluxing for 48 hours, the mixture was evaporated in vacuo. The residue was partitioned between ethyl acetate and water. The organic layer was separated and washed with brine, and dried over anhydrous $Na_2SO_4$. Flash column chromatography (MeOH/EtOAc, 1:6) gave 6 as a colorless oil (35 mg, 32%). $^1$H NMR ($CDCl_3$, 300 MHz) δ 8.27 (s, 1H), 7.89-7.80 (m, 4H), 7.56-7.40 (m, 2H), 6.21 (d, J=8.1 Hz, 1H), 4.93 (s, 2H), 4.10-3.90 (m, 1H), 3.15-2.95 (m, 1H), 2.80-2.30 (m, 8H), 2.20-1.90 (m, 3H), 1.89-1.61 (m, 3H), 1.55-1.05 (m, 9H), 0.90 (t, J=7.5 Hz, 3H); $^{13}$C NMR ($CDCl_3$, 75 MHz) δ 166.76, 165.55, 145.10, 134.61, 132.60, 132.19, 128.84, 128.35, 127.71, 127.50, 127.18, 126.68, 123.63, 117.33, 57.44, 52.62, 49.25, 48.52, 35.98, 35.17, 33.20, 31.95, 26.59, 25.78, 24.87, 22.16, 11.88; HRMS-Electrospray (m/z): [M+H]$^+$ calcd 491.2845. found 491.2845; purity HPLC 100.0%, $t_R$=31.816 min.

Trans-N-(4-(2-(((S)-2-amino-4,5,6,7-tetrahydrobenzo[d]thiazol-6-yl)(butyl)amino)ethyl)cyclohexyl)-2-naphthamide (7). Compound 7 was prepared under similar conditions as described for compound 6 (28%). $^1$H NMR ($CDCl_3$, 300 MHz) δ 8.28 (s, 1H), 7.92-7.81 (m, 4H), 7.57-7.40 (m, 2H), 6.26 (s, broad, 1H), 5.01 (s, 2H), 4.05-3.90 (m, 1H), 3.40-2.40 (m, 8H), 2.30-2.10 (m, 3H), 2.00-1.50 (m, 7H), 1.49-1.05 (m, 8H), 0.95 (t, J=7.2 Hz, 3H); $^{13}$C NMR ($CDCl_3$, 75 MHz) δ 167.18, 135.04, 133.01, 132.49, 129.28, 128.77, 128.13, 127.95, 127.65, 127.11, 124.07, 50.83, 49.49, 49.13, 35.63, 33.38, 32.16, 25.05, 20.94, 14.31; HRMS-Electrospray (m/z): [M+H]$^+$ calcd 505.3001. found 505.2995; purity HPLC 99.7%, $t_R$=34.009 min.

Trans-N-(4-(2-(((S)-2-amino-4,5,6,7-tetrahydrobenzo[d]thiazol-6-yl)(isopentyl)amino)ethyl)cyclohexyl)-2-naphthamide (8). Compound 8 was prepared under similar conditions as described for 6 (25%). $^1$H NMR ($CDCl_3$, 300 MHz) δ 8.27 (s, 1H), 7.93-7.80 (m, 4H), 7.56-7.48 (m, 2H), 6.15 (d, J=8.1 Hz, 1H), 4.87 (s, 2H), 4.10-3.90 (m, 1H), 3.50-2.50 (m, 8H), 2.30-2.10 (m, 3H), 2.00-1.10 (m, 14H), 0.94 (d, J=6.0 Hz, 6H). $^{13}$C NMR ($CDCl_3$, 75 MHz) δ 166.78, 144.81, 134.65, 132.61, 132.06, 128.88, 128.39, 127.74, 127.56, 127.24, 126.72, 123.64; HRMS-Electrospray (m/z): [M+H]$^+$ calcd 519.3158. found 519.3150; purity HPLC 98.3%, $t_R$=35.819 min.

Trans-N-(-4-(2-(((S)-2-amino-4,5,6,7-tetrahydrobenzo[d]thiazol-6-yl)(2-cyclohexylethyl)amino)ethyl)cyclohexyl)-2-naphthamide (9). Compound 9 was prepared under similar conditions as described for 6 (18%). $^1$H NMR ($CDCl_3$, 300 MHz) δ 8.29 (s, 1H), 7.90-7.70 (m, 4H), 7.55-7.35 (m, 2H), 6.36 (s, broad, 1H), 5.17 (s, 2H), 4.10-3.90 (m, 1H), 3.50-2.45 (m, 8H), 2.35-2.05 (m, 3H), 2.00-0.80 (m, 24H); $^{13}$C NMR ($CDCl_3$, 75 MHz) δ 166.81, 166.24, 144.63, 134.63, 132.60, 132.03, 128.89, 128.34, 127.71, 127.54, 127.31, 126.68, 123.72, 58.81, 49.06, 48.79, 48.63, 35.98, 35.38, 35.16, 34.80, 33.22, 32.88, 31.72, 29.69, 26.55, 26.37, 26.14, 24.63; HRMS-Electrospray (m/z): [M+H]$^+$ calcd 559.3471. found 559.3465; purity HPLC 100.0%, $t_R$=40.403 min.

Trans-tert-butyl-4-(2-((S)-2-amino-4,5,6,7-tetrahydrobenzo[d]thiazol-6-ylamino)ethyl)cyclohexylcarbamate (20). Bromide 17 (1.1 g, 3.6 mmol), cesium carbonate (1.47 g, 4.5 mmol), and sodium iodide (0.68 g, 4.5 mmol) were added to a solution of compound 19 (0.63 g, 3.0 mmol) in acetonitrile (40 mL). After refluxing for 48 hours, the mixture was evaporated in vacuo. The residue was partitioned between ethyl acetate and water. The organic layer was separated and washed with brine, and dried over anhydrous sodium sulfate ($Na_2SO_4$). Flash column chromatography (MeOH/EtOAc, 1:6) gave compound 20 as a colorless oil (0.8 g, 61%). $^1$H NMR ($CDCl_3$, 300 MHz) δ 4.93 (s, 2H), 4.02 (d, J=7.4 Hz, 1H), 3.50-3.30 (m, 1H), 3.10-2.95 (m, 1H), 2.80-2.35 (m, 8H), 2.05-1.90 (m, 3H), 1.85-1.60 (m, 3H), 1.55-1.00 (m, 9H), 1.44 (s, 9H), 0.87 (t, J=7.2 Hz, 3H).

Trans-N-(4-(2-(((S)-2-amino-4,5,6,7-tetrahydrobenzo[d]thiazol-6-yl)(propyl)amino)ethyl)cyclohexyl)benzofuran-2-carboxamide (11). 4.0 M HCl solution in dioxane (1.0 mL, 4.0 mmol) was added to a solution of compound 20 (87 mg, 0.2 mmol) in dioxane (10 mL) and the reaction mixture was stirred at room temperature for 2 hours. Solvent was evaporated in vacuo and the residue was used directly for the next step without further purification. To a solution of the residue in tetrahydrofuran (THF) (20 mL), were added benzofuran-2-carboxylic acid (32 mg, 0.2 mmol), 1-ethyl-3(3-dimethylaminopropyl)carbodiimide (EDCI) (38 mg, 0.2 mmol), 1-hydroxybenzotriazole (HOBT) (27 mg, 0.2 mmol), and diisopropylethylamine (DIPEA) (103 mg, 0.8 mmol). The reaction mixture was stirred at room temperature for 2 hours. Solvent was evaporated in vacuo. The residue was partitioned between ethyl acetate and water. The organic layer was separated and washed with brine, and dried over anhydrous $Na_2SO_4$. Flash column chromatography (MeOH/EtOAc, 1:6) gave compound 11 as a colorless oil (60 mg, 63%). $^1$H NMR ($CDCl_3$, 300 MHz) δ 7.68 (d, 7.6 Hz, 1H), 7.52-7.28 (m, 4H), 6.49 (d, J=8.2 Hz, 1H), 4.82 (s, broad, 2H), 3.98-3.85 (m, 1H), 3.50-2.25 (m, 8H), 2.20-1.10 (m, 16H), 0.94 (t, J=6.6 Hz, 3H); $^{13}$C NMR ($CDCl_3$, 75 MHz) δ 158.50, 155.06, 149.22, 128.06, 127.22, 124.08, 123.11, 112.08, 110.71, 52.80, 48.68, 35.63, 33.04, 31.74, 19.26, 11.97, 11.77; HRMS-Electrospray (m/z): [M+H]$^+$ calcd 481.2637. found 481.2637; purity HPLC 99.2%, $t_R$=29.761 min.

Trans-N-(4-(2-(((S)-2-amino-4,5,6,7-tetrahydrobenzo[d]thiazol-6-yl)(propyl)amino)ethyl)cyclohexyl)cinnamamide (12). 4.0 M HCl solution in dioxane (1.0 mL, 4.0 mmol) was added to a solution of compound 20 (87 mg, 0.2 mmol) in dioxane (10 mL) and the reaction mixture was stirred at room temperature for 2 hours. Solvent was evaporated in vacuo and the residue was used directly for the next step without further purification. To a solution of the residue in THF (20 mL) were added cinnamic acid (29 mg, 0.2 mmol), EDCI (38 mg, 0.2 mmol), HOBT (27 mg, 0.2 mmol), and DIPEA (103 mg, 0.8 mmol). The reaction mixture was stirred at room temperature for 2 hours. Solvent was evaporated in vacuo. The residue was partitioned between ethyl acetate and water. The organic layer was separated and washed with brine, and dried over anhydrous Na$_2$SO$_4$. Flash column chromatography (MeOH/EtOAc, 1:6) gave compound 12 as a colorless oil (75 mg, 80%). $^1$H NMR (CDCl$_3$, 300 MHz) δ 7.63 (d, J=15.6 Hz, 1H), 7.52-7.35 (m, 5H), 6.39 (d, J=15.6 Hz, 1H), 5.60 (s, broad, 1H), 4.90 (s, 2H), 3.95-3.80 (m, 1H), 3.30-2.30 (m, 8H), 2.20-1.95 (m, 3H), 1.93-1.02 (m, 13H), 0.92 (t, J=6.6 Hz, 3H); $^{13}$C NMR (CDCl$_3$, 75 MHz) δ 165.87, 165.05, 144.85, 140.66, 134.92, 129.54, 128.77, 127.73, 121.10, 69.73, 57.86, 52.54, 48.71, 35.18, 33.06, 31.80, 30.84, 26.34, 25.36, 24.76, 18.88, 11.79; HRMS-Electrospray (m/z): [M+H]$^+$ calcd 467.2845. found 467.2830; purity HPLC 95.4%, $t_R$=29.227 min.

Purity of compounds was determined by HPLC, including impurity tracings information.

| Impurity tracings | | | |
|---|---|---|---|
| Compound No. | Retention time (min) | Purity (%) | Retention time (min) | % |
| 6 | 31.816 | 100.0 | — | — |
| 7 | 34.009 | 99.7 | 33.453 | 0.3 |
| 8 | 35.819 | 98.3 | 23.632 | 1.7 |
| 9 | 40.403 | 100.0 | — | — |
| 10 | 29.903 | 100.0 | — | — |
| 11 | 29.761 | 99.2 | 23.715 | 0.8 |
| 12 | 29.227 | 95.4 | 28.895 | 4.6 |

The following additional compounds of the invention were prepared by the above synthetic schemes using appropriate starting materials:

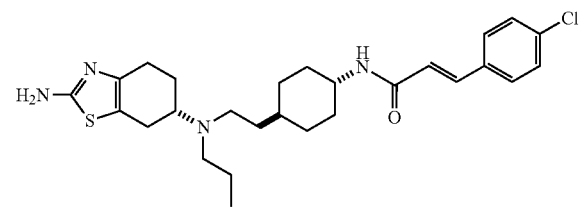

$^1$H NMR (400 MHz, CDCl$_3$), δ 7.56 (d, J=15.6 Hz, 1H), 7.41 (d, J=8.4 Hz, 2H), 7.32 (d, J=8.4 Hz, 2H), 6.35 (d, J=15.6 Hz, 1H), 5.65 (d, J=8.0 Hz, 1H), 4.88 (s, 2H), 3.91-3.80 (m, 1H), 3.08-3.00 (m, 1H), 2.75-2.38 (m, 8H), 2.30-1.92 (m, 3H), 1.84-1.60 (m, 3H), 1.50-1.10 (m, 9H), 0.90 (t, J=7.5 Hz, 3H); $^{13}$C NMR (100 MHz, CDCl$_3$), δ 165.56, 164.74, 145.15, 139.37, 135.36, 133.46, 129.05, 128.91, 121.67, 117.53, 57.40, 52.65, 48.81, 48.50, 36.03, 35.16, 33.18, 31.89, 26.63, 25.05, 24.92, 22.27, 11.89.

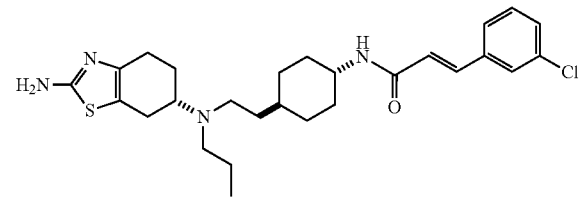

$^1$H NMR (400 MHz, CDCl$_3$), δ 7.55 (d, J=15.2 Hz, 1H), 7.48 (s, 1H), 7.38-7.26 (m, 3H), 6.37 (d, J=15.2 Hz, 1H), 5.65 (d, J=8.0 Hz, 1H), 4.84 (s, 2H), 3.92-3.80 (m, 1H), 3.08-2.98 (m, 1H), 2.76-2.38 (m, 8H), 2.10-1.92 (m, 3H), 1.82-1.63 (m, 3H), 1.50-1.20 (m, 9H), 0.91 (t, J=7.5 Hz, 3H); $^{13}$C NMR (100 MHz, CDCl$_3$), δ 165.48, 164.53, 145.19, 139.25, 136.83, 134.78, 130.08, 129.44, 127.30, 126.15, 122.52, 117.61, 57.39, 52.65, 48.93, 48.50, 36.09, 35.15, 33.17, 31.89, 26.65, 25.88, 24.93, 22.29, 11.89.

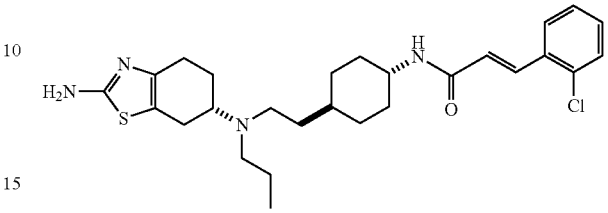

$^1$H NMR (400 MHz, CDCl$_3$), δ 7.95 (d, J=15.6 Hz, 1H), 7.55 (dd, J=7.2, 2.0 Hz, 1H), 7.40 (dd, J=7.2, 2.0 Hz, 1H), 7.30-7.20 (m, 2H), 6.39 (d, J=15.6 Hz, 1H), 5.72 (d, J=8.0 Hz, 1H), 4.89 (s, 2H), 3.92-3.80 (m, 1H), 3.07-2.96 (m, 1H), 2.76-2.40 (m, 8H), 2.10-1.95 (m, 3H), 1.82-1.64 (m, 3H), 1.50-1.10 (m, 9H), 0.90 (t, J=7.5 Hz, 3H); $^{13}$C NMR (100 MHz, CDCl$_3$), δ 165.59, 164.62, 145.12, 136.58, 134.69, 133.33, 130.32, 130.15, 127.54, 126.92, 124.14, 117.49, 57.42, 52.65, 48.93, 48.52, 36.04, 35.17, 33.15, 31.92, 26.62, 25.85, 24.91, 22.25, 11.89.

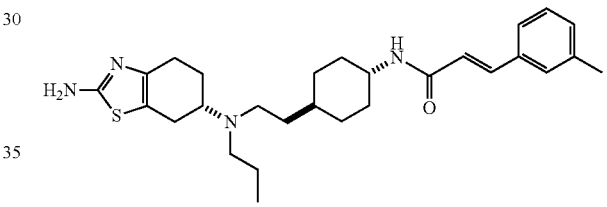

$^1$H NMR (400 MHz, CDCl$_3$), δ 7.58 (d, J=15.6 Hz, 1H), 7.35-7.15 (m, 4H), 6.36 (d, J=15.6 Hz, 1H), 5.54 (d, J=8.0 Hz, 1H), 4.83 (s, 2H), 3.92-3.80 (m, 1H), 3.10-2.98 (m, 1H), 2.78-2.40 (m, 8H), 2.37 (s, 3H), 2.10-1.95 (m, 3H), 1.82-1.64 (m, 3H), 1.50-1.12 (m, 9H), 0.91 (t, J=7.6 Hz, 3H); $^{13}$C NMR (100 MHz, CDCl$_3$), δ 165.48, 165.11, 145.18. 140.88, 138.41, 134.89, 130.39, 128.68, 128.47, 124.88, 120.89, 117.58, 57.43, 52.66, 48.82, 48.53, 36.04, 35.19, 33.23, 31.91, 26.64, 25.86, 24.93, 22.26, 21.35, 11.89.

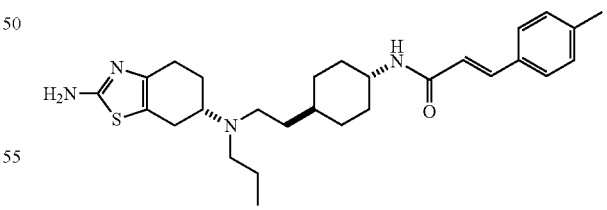

$^1$H NMR (400 MHz, CDCl$_3$), δ 7.54 (d, J=15.6 Hz, 1H), 7.31-7.27 (m, 2H), 7.06 (d, J=7.2 Hz, 1H), 6.42-6.30 (m, 2H), 5.35 (s, 2H), 3.88-3.72 (m, 1H), 3.00-2.88 (m, 1H), 2.65-2.30 (m, 8H), 2.28 (s, 3H), 2.00-1.83 (m, 3H), 1.78-1.57 (m, 3H), 1.42-0.90 (m, 9H), 0.80 (t, J=7.6 Hz, 3H); $^{13}$C NMR (100 MHz, CDCl$_3$), δ 165.87, 165.50, 144.90, 140.38, 139.60, 132.25, 129.45, 127.71, 120.39, 116.92, 57.42, 52.61, 48.80, 48.50, 36.10, 35.12, 33.08, 31.97, 26.61, 25.88, 24.88, 22.25, 21.36, 11.89.

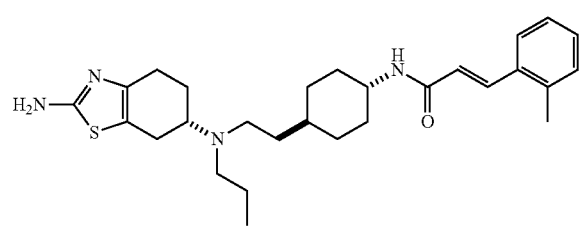

¹H NMR (400 MHz, CDCl₃), δ 7.87 (d, J=15.6 Hz, 1H), 7.44 (d, J=8.0 Hz, 1H), 7.20-7.08 (m, 3H), 6.32 (d, J=15.6 Hz, 1H), 6.20-5.95 (m, 1H), 5.20 (s, 2H), 3.88-3.80 (m, 1H), 3.03-2.93 (m, 1H), 2.70-2.30 (m, 8H), 2.37 (s, 3H), 2.04-1.93 (m, 3H), 1.80-1.60 (m, 3H), 1.42-1.00 (m, 9H), 0.83 (t, J=7.6 Hz, 3H); ¹³C NMR (100 MHz, CDCl₃), δ 165.96, 165.25, 145.00, 138.38, 137.42, 134.03, 130.69, 129.26, 126.12, 126.06, 122.42, 117.12, 57.43, 52.65, 48.87, 48.51, 36.10, 35.15, 33.13, 31.93, 26.63, 25.89, 24.91, 22.27, 19.83, 11.90.

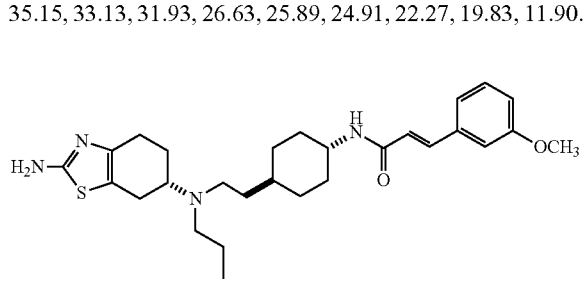

¹H NMR (400 MHz, CDCl₃), δ 7.54 (d, J=15.6 Hz, 1H), 7.23-6.94 (m, 3H), 6.85 (dd, J=8.0, 2.0 Hz, 1H), 6.38 (d, J=15.6 Hz, 1H), 5.92 (d, J=8.0 Hz, 1H), 5.07 (s, 2H), 3.88-3.80 (m, 1H), 3.78 (s, 3H), 3.03-2.93 (m, 1H), 2.70-2.30 (m, 8H), 2.04-1.90 (m, 3H), 1.80-1.60 (m, 3H), 1.50-1.00 (m, 9H), 0.83 (t, J=7.6 Hz, 3H); ¹³C NMR (100 MHz, CDCl₃), δ 165.81, 165.03, 159.82, 145.05, 140.47, 136.39, 129.75, 121.59, 120.34, 117.26, 115.24, 112.88, 57.43, 55.24, 52.63, 48.84, 48.50, 36.06, 35.15, 33.15, 31.91, 26.62, 25.87, 24.91, 22.25, 11.88.

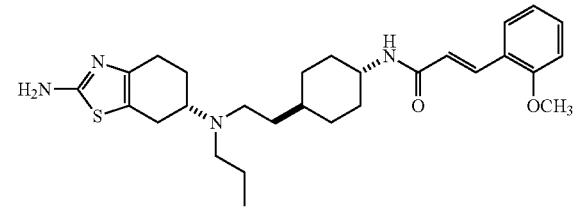

¹H NMR (400 MHz, CDCl₃), δ 7.83 (d, J=15.6 Hz, 1H), 7.40 (d, J=7.6 Hz, 1H), 7.27-7.21 (m, 1H), 6.97-6.82 (m, 2H), 6.52 (d, J=15.6 Hz, 1H), 6.11 (m, 1H), 5.26 (s, 2H), 3.88-3.80 (m, 1H), 3.79 (s, 3H), 3.03-2.93 (m, 1H), 2.70-2.30 (m, 8H), 2.04-1.88 (m, 3H), 1.78-1.58 (m, 3H), 1.50-0.90 (m, 9H), 0.80 (t, J=7.6 Hz, 3H); ¹³C NMR (100 MHz, CDCl₃), δ 166.04, 165.80, 158.13, 144.95, 135.85, 130.54, 128.82, 123.98, 122.21, 120.57, 116.99, 111.04, 57.44, 55.36, 52.62, 48.74, 48.52, 36.09, 35.15, 33.10, 31.97, 26.00, 25.88, 24.90, 22.24, 11.89.

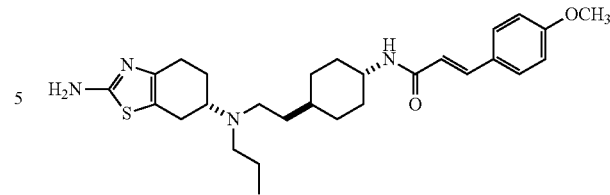

¹H NMR (400 MHz, CDCl₃), δ 7.50 (d, J=15.6 Hz, 1H), 7.35 (d, J=8.4 Hz, 2H), 6.77 (d, J=8.4 Hz, 2H), 6.29 (d, J=15.6 Hz, 1H), 6.30-6.25 (m, 1H), 5.28 (s, 2H), 3.83-3.80 (m, 1H), 3.73 (s, 3H), 3.00-2.90 (m, 1H), 2.65-2.30 (m, 8H), 2.00-1.83 (m, 3H), 1.78-1.58 (m, 3H), 1.40-0.93 (m, 9H), 0.80 (t, J=7.6 Hz, 3H); ¹³C NMR (100 MHz, CDCl₃), δ 166.12, 165.60, 160.66, 144.91, 140.01, 129.24, 127.73, 119.06, 116.89, 114.15, 57.42, 55.26, 52.60, 48.76, 48.48, 36.08, 35.11, 33.10, 31.94, 26.00, 25.87, 24.87, 22.23, 11.88.

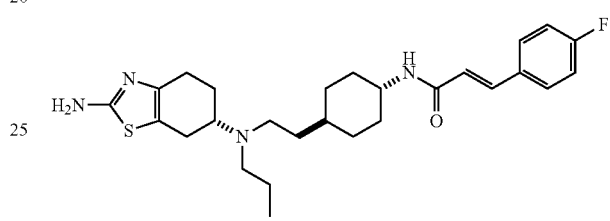

¹H NMR (400 MHz, CDCl₃), δ 7.58 (d, J=15.6 Hz, 1H), 7.50-7.47 (m, 2H), 7.07 (t, J=8.8 Hz, 2H), 6.29 (d, J=15.6 Hz, 1H), 5.52 (d, J=8.0 Hz, 1H), 4.80 (s, 2H), 3.90-3.80 (m, 1H), 3.20-3.09 (m, 1H), 2.80-2.40 (m, 8H), 2.13-2.00 (m, 3H), 1.80-1.70 (m, 3H), 1.60-1.07 (m, 9H), 0.92 (t, J=7.6 Hz, 3H); ¹³C NMR (100 MHz, CDCl₃), δ 165.55, 164.85, 164.73, 162.24, 145.12, 139.55, 131.19, 129.54, 129.46, 120.81, 116.00, 115.79, 57.79, 52.62, 48.79, 48.65, 35.19, 33.13, 31.83, 28.83, 26.47, 25.53, 24.82, 11.81.

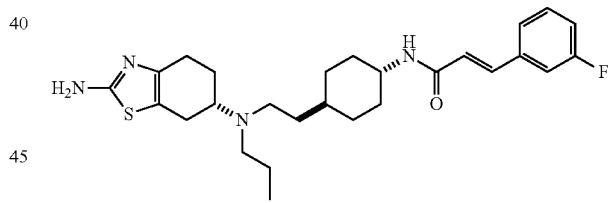

¹H NMR (400 MHz, CDCl₃), δ 7.53 (d, J=15.6 Hz, 1H), 7.30-6.95 (m, 4H), 6.39 (d, J=15.6 Hz, 1H), 6.12 (d, J=8.0 Hz, 1H), 5.13 (s, 2H), 3.90-3.80 (m, 1H), 3.05-2.95 (m, 1H), 2.70-2.30 (m, 8H), 2.03-1.90 (m, 3H), 1.80-1.60 (m, 3H), 1.50-1.00 (m, 9H), 0.91 (t, J=7.6 Hz, 3H); ¹³C NMR (100 MHz, CDCl₃), δ 165.88, 164.75, 145.02, 139.24, 137.34, 130.33 130.26, 123.86, 122.06, 117.19, 116.20, 113.90, 113.69, 57.42, 52.62, 48.92, 48.48, 36.03, 35.12, 33.08, 31.91, 26.61, 25.85, 24.89, 22.22, 11.87.

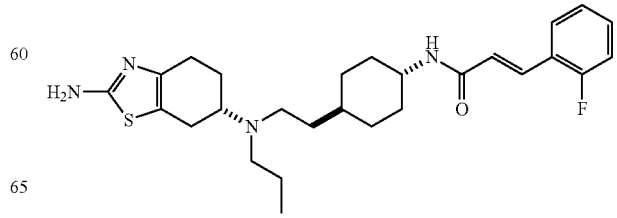

¹H NMR (400 MHz, CDCl₃), δ 7.65 (d, J=16.0 Hz, 1H), 7.50-6.98 (m, 4H), 6.53 (d, J=16.0 Hz, 1H), 6.00-5.84 (m, 1H), 5.02 (s, 2H), 3.90-3.80 (m, 1H), 3.05-2.95 (m, 1H), 2.70-2.30 (m, 8H), 2.03-1.90 (m, 3H), 1.80-1.60 (m, 3H), 1.50-1.00 (m, 9H), 0.91 (t, J=7.6 Hz, 3H); ¹³C NMR (100 MHz, CDCl₃), δ 165.73, 164.99, 162.55, 160.04, 145.09, 133.62, 130.80, 130.72, 129.60, 124.25, 124.31, 124.17, 123.05, 122.94, 117.32, 116.19, 115.97, 57.42, 52.65, 48.89, 48.51, 36.07, 35.15, 33.11, 31.91, 26.62, 25.87, 24.91, 22.25, 11.88.

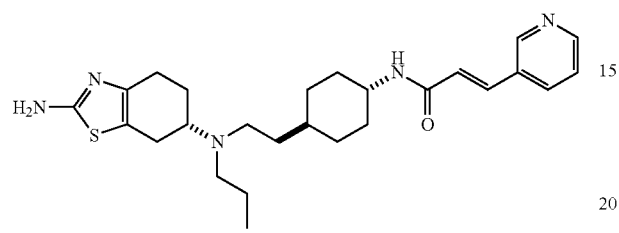

¹H NMR (400 MHz, CDCl₃), δ 8.73 (s, 1H), 8.55-8.53 (m, 1H), 7.75 (d, J=8.0 Hz, 1H), 7.58 (d, J=15.6 Hz, 1H), 7.30-7.26 (m, 1H), 6.45 (d, J=15.6 Hz, 1H), 5.96-5.80 (m, 1H), 4.96 (s, 2H), 3.90-3.80 (m, 1H), 3.05-2.95 (m, 1H), 2.70-2.34 (m, 8H), 2.05-1.90 (m, 3H), 1.80-1.60 (m, 3H), 1.50-1.03 (m, 9H), 0.91 (t, J=7.6 Hz, 3H); ¹³C NMR (100 MHz, CDCl₃), δ 165.65, 164.32, 150.19, 149.04, 145.11, 137.02, 131.39, 130.83, 123.69, 123.33, 117.44, 57.40, 52.65, 48.99, 48.49, 36.07, 35.15, 33.13, 31.90, 26.63, 25.86, 24.93, 22.27, 11.88.

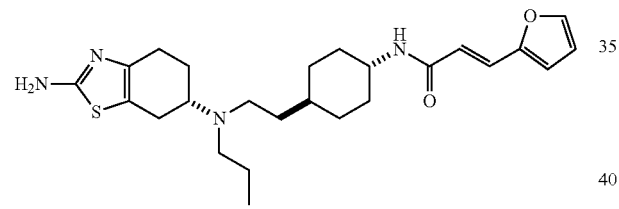

¹H NMR (400 MHz, CDCl₃), δ 7.38-7.33 (m, 2H), 6.49 (d, J=3.2 Hz, 1H), 6.40 (dd, J=3.2, 2.0 Hz, 1H), 6.25 (d, J=15.2 Hz, 1H), 5.65 (d, J=8.0 Hz, 1H), 4.96 (s, 2H), 3.88-3.78 (m, 1H), 3.05-2.95 (m, 1H), 2.70-2.34 (m, 8H), 2.05-1.90 (m, 3H), 1.80-1.60 (m, 3H m), 1.45-1.03 (, 9H), 0.91 (t, J=7.6 Hz, 3H); ¹³C NMR (100 MHz, CDCl₃), δ 165.63, 164.96, 151.41, 145.13, 143.84, 127.67, 118.86, 117.45, 113.52, 112.10, 57.37, 52.65, 48.83, 48.50, 36.11, 35.15, 33.18, 31.94, 26.64, 25.88, 24.89, 22.33, 11.91.

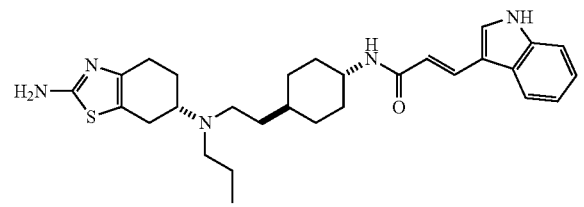

¹H NMR (400 MHz, CDCl₃), δ 9.05 (s, 1H), 7.90-7.80 (m, 2H), 7.42-7.20 (m, 4H), 6.42 (d, J=16.0 Hz, 1H), 5.56 (s, 1H), 4.96 (s, 2H), 3.88-3.82 (m, 1H), 3.05-2.98 (m, 1H), 2.76-2.40 (m, 8H), 2.05-1.95 (m, 3H), 1.90-1.60 (m, 3H), 1.50-1.03 (m, 9H), 0.84 (t, J=7.6 Hz, 3H); ¹³C NMR (100 MHz, CDCl₃), δ 166.45, 165.45, 145.24, 137.24, 134.37, 128.18, 125.46, 122.95, 121.00, 120.32, 117.75, 116.52, 113.68, 111.84, 57.49, 52.69, 48.79, 48.56, 36.17, 35.24, 33.37, 31.98, 26.66, 25.93, 25.05, 22.30, 11.84.

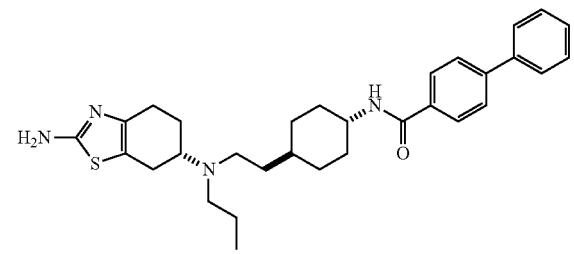

¹H NMR (400 MHz, CDCl₃), δ 7.83 (d, J=8.0 Hz, 2H), 7.65-7.40 (m, 7H), 6.10 (d, J=8.0 Hz, 1H), 4.94 (s, 2H), 4.00-3.90 (m, 1H), 3.08-2.98 (m, 1H), 2.76-2.40 (m, 8H), 2.18-1.95 (m, 3H), 1.90-1.62 (m, 3H), 1.50-1.03 (m, 9H), 0.84 (t, J=7.6 Hz, 3H); ¹³C NMR (100 MHz, CDCl₃), δ 166.99, 165.12, 143.68, 142.59, 138.59, 132.18, 127.45, 126.49, 125.93, 125.72, 125.70, 116.01, 55.90, 51.17, 47.72, 47.05, 34.65, 33.71, 31.75, 30.49, 25.18, 24.40, 23.43, 20.84, 10.44.

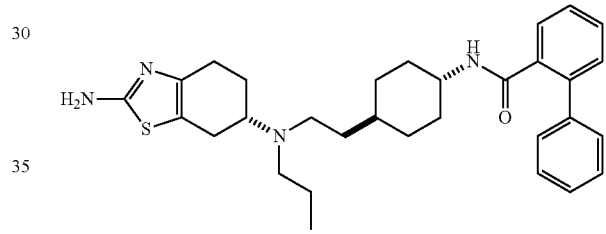

¹H NMR (400 MHz, CDCl₃), δ 7.75-7.70 (m, 1H), 7.55-7.37 (m, 7H), 4.99 (d, J=8.0 Hz, 1H), 4.84 (s, 2H), 3.70-3.60 (m, 1H), 3.04-2.95 (m, 1H), 2.74-2.38 (m, 8H), 2.12-1.90 (m, 1H), 1.86-1.60 (m, 5H), 1.50-0.60 (m, 9H), 0.84 (t, J=7.6 Hz, 3H); ¹³C NMR (100 MHz, CDCl₃), δ 168.45, 165.47, 145.16, 140.33, 139.38, 136.07, 130.06, 129.97, 128.89, 128.81, 128.64, 127.77, 127.64, 117.66, 57.37, 52.65, 48.79, 48.51, 36.06, 35.01, 32.38, 31.75, 26.64, 25.86, 24.89, 22.29, 11.68.

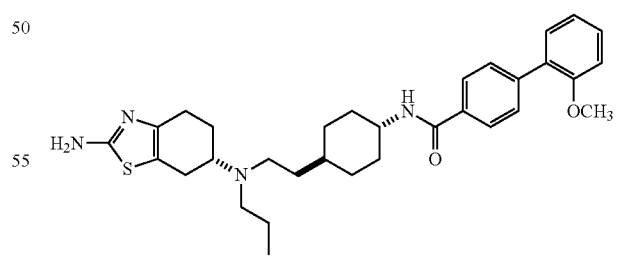

¹H NMR (400 MHz, CDCl₃), δ 7.77 (dd, J=6.8, 2.0 Hz, 2H), 7.60-7.58 (m, 2H), 7.39-6.96 (m, 4H), 6.05 (d, J=8.0 Hz, 1H), 4.94 (s, 2H), 3.96-3.84 (m, 1H), 3.78 (s, 3H), 3.04-2.95 (m, 1H), 2.74-2.40 (m, 8H), 2.10-1.90 (m, 3H), 1.83-1.60 (m, 3H), 1.50-1.10 (m, 9H), 0.87 (t, J=7.2 Hz, 3H); ¹³C NMR (100 MHz, CDCl₃), δ 166.67, 165.64, 156.44, 145.15, 141.68, 133.33, 130.73, 129.68, 129.63, 129.27, 126.55, 120.95, 117.45, 111.32, 57.39, 55.56, 52.66, 49.13, 48.54, 36.15, 35.20, 33.25, 32.00, 26.68, 25.91, 24.92, 22.34, 11.93.

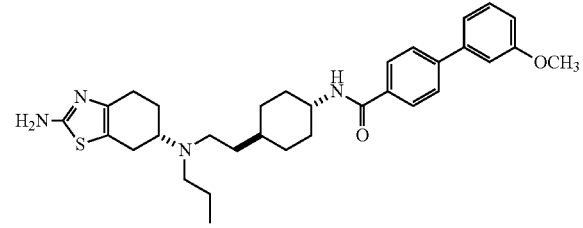

¹H NMR (400 MHz, CDCl₃), δ 7.80 (d, J=8.4 Hz, 2H), 7.60 (d, J=8.4 Hz, 2H), 7.35 (t, J=8.0 Hz, 1H), 7.20-6.90 (m, 3H), 6.08 (d, J=8.4 Hz, 1H), 4.92 (s, 2H), 3.96-3.84 (m, 1H), 3.83 (s, 3H), 3.04-2.95 (m, 1H), 2.74-2.37 (m, 8H), 2.10-1.90 (m, 3H), 1.82-1.60 (m, 3H), 1.46-1.10 (m, 9H), 0.86 (t, J=7.2 Hz, 3H); ¹³C NMR (100 MHz, CDCl₃), δ 166.44, 165.59, 160.00, 145.17, 143.92, 141.58, 133.82, 129.96, 127.38, 127.22, 119.69, 117.48, 113.22, 113.03, 57.39, 55.37, 52.66, 49.21, 48.53, 36.15, 35.19, 33.23, 31.99, 26.67, 25.89, 24.92, 22.33, 11.92.

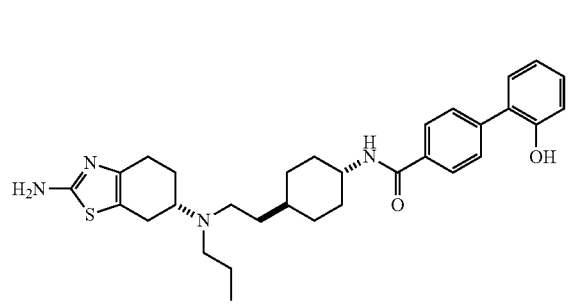

¹H NMR (400 MHz, CDCl₃), δ 7.83 (d, J=8.4 Hz, 2H), 7.58 (d, J=8.4 Hz, 2H), 7.30-7.23 (m, 2H), 7.02-6.90 (m, 2H), 5.99 (d, J=7.6 Hz, 1H), 4.72 (s, 2H), 3.96-3.84 (m, 1H), 3.08-2.98 (m, 1H), 2.74-2.40 (m, 8H), 2.18-1.90 (m, 3H), 1.82-1.60 (m, 3H), 1.50-1.12 (m, 9H), 0.86 (t, J=7.2 Hz, 3H); ¹³C NMR (100 MHz, CDCl₃), δ 166.49, 165.51, 152.94, 145.11, 140.93, 133.86, 130.35, 129.50, 129.38, 127.44, 127.34, 120.81, 116.29, 57.44, 52.65, 49.23, 48.53, 35.19, 33.22, 31.95, 31.92, 26.58, 25.81, 24.92, 22.19, 11.88.

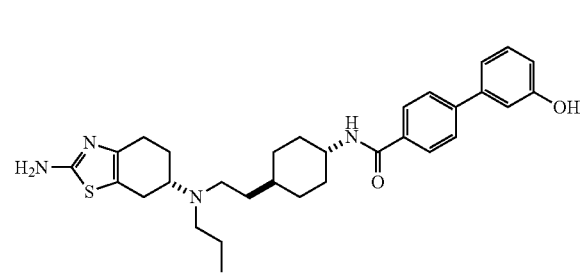

¹H NMR (400 MHz, CDCl₃), δ 7.80 (d, J=8.0 Hz, 2H), 7.59 (d, J=8.0 Hz, 2H), 7.30-7.09 (m, 3H), 6.88 (d, J=8.0 Hz, 2H), 6.04 (d, J=8.0 Hz, 1H), 4.73 (s, 2H), 3.96-3.84 (m, 1H), 3.08-2.98 (m, 1H), 2.75-2.40 (m, 8H), 2.18-1.90 (m, 3H), 1.82-1.60 (m, 3H), 1.50-1.12 (m, 9H), 0.84 (t, J=7.2 Hz, 3H); ¹³C NMR (100 MHz, CDCl₃), δ 166.72, 165.62, 157.06, 145.05, 144.12, 141.50, 133.55, 130.12, 127.36, 127.22, 118.94, 117.65, 115.35, 114.39, 57.36, 52.65, 49.31, 48.51, 35.95, 35.21, 33.17, 31.94, 26.58, 25.82, 24.91, 22.15, 11.90.

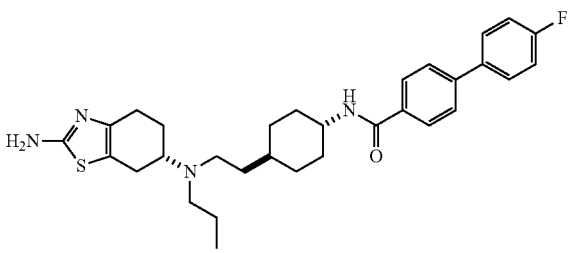

¹H NMR (400 MHz, CDCl₃), δ 7.80 (d, J=8.0 Hz, 2H), 7.60-7.50 (m, 4H), 7.12 (t, J=8.8 Hz, 2H), 6.05 (d, J=8.0 Hz, 1H), 4.90 (s, 2H), 3.96-3.83 (m, 1H), 3.05-2.97 (m, 1H), 2.73-2.37 (m, 8H), 2.18-1.90 (m, 3H), 1.82-1.60 (m, 3H), 1.50-1.10 (m, 9H), 0.83 (t, J=7.2 Hz, 3H); ¹³C NMR (100 MHz, CDCl₃), δ 166.35, 165.56, 145.17, 143.04, 136.21, 136.17, 133.68, 128.86, 128.78, 127.48, 127.02, 117.49, 115.96, 115.75, 57.39, 52.65, 49.23, 48.52, 36.11, 35.19, 33.22, 31.99, 26.66, 25.88, 24.91, 22.29, 11.91.

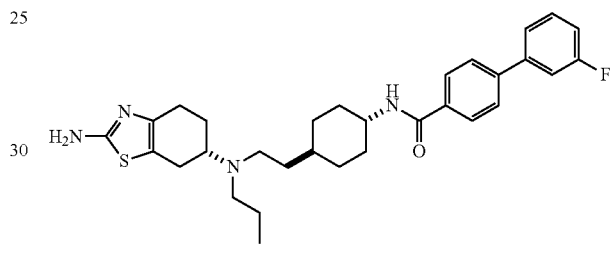

¹H NMR (400 MHz, CDCl₃), δ 7.81 (d, J=8.0 Hz, 2H), 7.58 (d, J=8.0 Hz, 2H), 7.42-7.02 (m, 4H), 6.02 (d, J=8.0 Hz, 1H), 4.82 (s, 2H), 3.96-3.83 (m, 1H), 3.06-2.97 (m, 1H), 2.73-2.38 (m, 8H), 2.18-1.90 (m, 3H), 1.82-1.60 (m, 3H), 1.50-1.12 (m, 9H), 0.83 (t, J=7.2 Hz, 3H); ¹³C NMR (100 MHz, CDCl₃), δ 166.26, 165.47, 145.21, 142.71, 134.28, 130.48, 127.51, 127.17, 122.86, 117.57, 114.86, 114.66, 114.21, 113.99, 57.43, 52.66, 49.25, 48.53, 38.09, 35.19, 33.23, 31.96, 26.66, 25.88, 24.94, 22.28, 11.88.

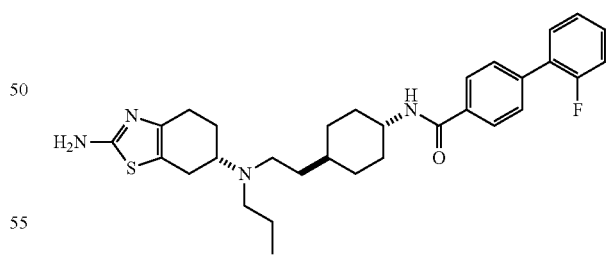

¹H NMR (400 MHz, CDCl₃), δ 7.81 (d, J=8.0 Hz, 2H), 7.58 (d, J=8.0 Hz, 2H), 7.42-7.10 (m, 4H), 6.03 (d, J=8.0 Hz, 1H), 4.85 (s, 2H), 3.96-3.83 (m, 1H), 3.06-2.93 (m, 1H), 2.71-2.35 (m, 8H), 2.18-1.90 (m, 3H), 1.82-1.60 (m, 3H), 1.50-1.14 (m, 9H), 0.84 (t, J=7.2 Hz, 3H); ¹³C NMR (100 MHz, CDCl₃), δ 166.41, 165.51, 145.20, 138.77, 130.65, 129.69, 129.17, 128.12, 127.01, 124.55, 117.58, 116.35, 57.39, 52.66, 49.22, 48.53, 36.14, 35.19, 33.23, 31.97, 26.67, 25.89, 24.93, 22.33, 11.91.

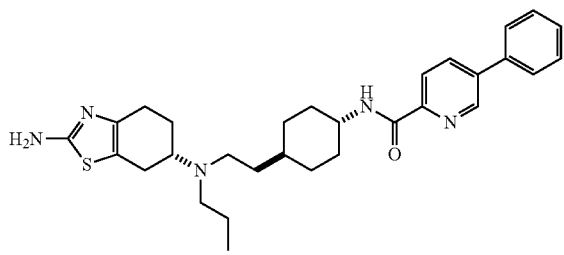

¹H NMR (CDCl₃, 400 MHz) δ 8.77 (s, 1H), 8.22 (d, J=8.4, 1H), 8.00-7.82 (m, 2H), 7.60-7.40 (m, 5H), 5.08 (s, 2H), 3.95-3.80 (m, 1H), 3.32-3.20 (m, 1H), 2.90-2.45 (m, 8H), 2.20-2.04 (m, 3H), 1.90-1.72 (m, 3H), 1.70-1.00 (m, 9H), 0.88 (t, J=7.6 Hz, 3H); ¹³C NMR (CDCl₃, 100 MHz) δ 166.28, 163.37, 148.73, 146.51, 144.51, 138.98, 137.01, 135.58, 129.25, 128.70, 128.31, 127.27, 122.26, 58.29, 53.88, 52.61, 48.91, 48.53, 42.20, 35.24, 32.88, 31.79, 26.07, 24.96, 24.58, 11.75.

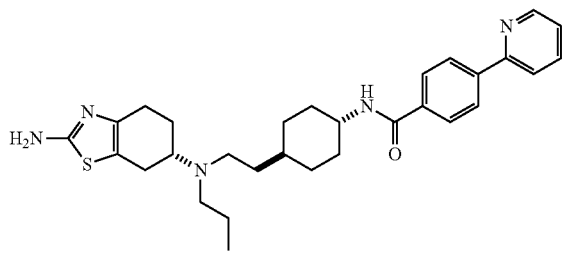

¹H NMR (CDCl₃, 400 MHz) δ 8.66 (d, J=4.4 Hz, 1H), 8.00-7.65 (m, 6H), 7.23-7.20 (m, 1H), 6.28 (d, J=4.4 Hz, 1H), 5.12 (s, 2H), 4.00-3.83 (m, 1H), 3.02-2.94 (m, 1H), 2.70-2.35 (m, 8H), 2.20-1.84 (m, 3H), 1.80-1.60 (m, 3H), 1.50-1.10 (m, 9H), 0.84 (t, J=7.2 Hz, 3H); ¹³C NMR (CDCl₃, 100 MHz) δ 166.39, 165.89, 156.25, 149.79, 145.00, 141.92, 136.92, 135.17, 127.41, 126.91, 122.71, 120.83, 117.06, 57.46, 52.62, 49.27, 48.53, 35.98, 35.15, 33.09, 31.97, 26.59, 25.83, 24.89, 22.17, 11.88.

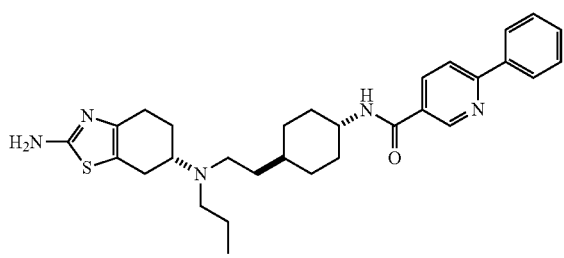

¹H NMR (CDCl₃, 400 MHz) δ 9.00 (d, J=2.0 Hz, 1H), 8.12 (dd, J=8.4, 2.4 Hz, 1H), 7.97 (d, J=8.0 Hz, 1H), 7.73 (d, J=8.4 Hz, 1H), 7.50-7.32 (m, 3H), 6.37 (d, J=8.0 Hz, 1H), 5.04 (s, 2H), 3.95-3.80 (m, 1H), 3.02-2.94 (m, 1H), 2.75-2.35 (m, 8H), 2.10-1.60 (m, 6H), 1.45-1.00 (m, 9H), 0.83 (t, J=7.6 Hz, 3H); ¹³C NMR (CDCl₃, 100 MHz) δ 165.54, 164.84, 159.64, 147.89, 145.16, 138.38, 135.95, 129.71, 128.89, 128.71, 127.18, 120.03, 117.49, 57.38, 52.64, 49.39, 48.49, 36.09, 35.12, 33.09, 31.94, 26.66, 25.86, 24.89, 22.29, 11.89.

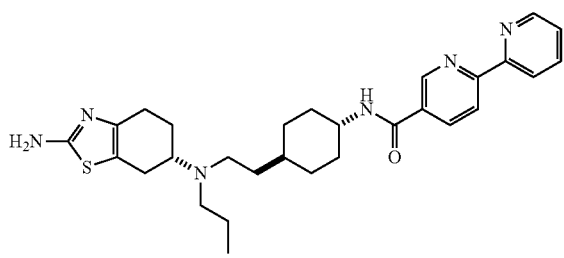

¹H NMR (CDCl₃, 400 MHz) δ 8.52 (s, 1H), 8.00 (d, J=8.0 Hz, 2H), 7.82 (d, J=8.0 Hz, 2H), 7.64 (d, J=8.0 Hz, 1H), 7.56 (d, J=8.0 Hz, 2H), 6.03 (d, J=7.6 Hz, 1H), 4.84 (s, 2H), 4.00-3.88 (m, 1H), 3.06-2.94 (m, 1H), 2.70-2.35 (m, 8H), 2.37 (s, 3H), 2.20-1.86 (m, 3H), 1.82-1.60 (m, 3H), 1.46-1.10 (m, 9H), 0.84 (t, J=7.2 Hz, 3H); ¹³C NMR (CDCl₃, 100 MHz) δ 166.38, 165.48, 153.60, 150.28, 145.19, 142.06, 137.45, 134.80, 132.41, 127.31, 126.71, 120.34, 117.56, 57.40, 52.65, 49.23, 48.53, 36.11, 35.19, 33.22, 31.97, 26.66, 25.86, 24.91, 22.29, 18.25, 11.90.

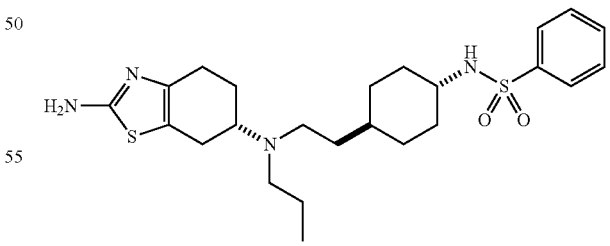

¹H NMR (CDCl₃, 400 MHz) δ 9.04 (d, J=2.4 Hz, 1H), 8.72 (d, J=4.8 Hz, 1H), 8.48 (m, 2H), 8.19 (dd, J=8.4, 2.4 Hz, 1H), 7.86 (t, J=7.6 Hz, 1H), 7.37 (dd, J=8.4, 4.8 Hz, 1H), 6.02 (d, J=7.6 Hz, 1H), 4.75 (s, 2H), 4.02-3.90 (m, 1H), 3.22-3.04 (m, 1H), 2.70-2.35 (m, 8H), 2.20-2.00 (m, 3H), 1.92-1.10 (m, 12H), 0.92 (t, J=7.2 Hz, 3H); ¹³C NMR (CDCl₃, 100 MHz) δ 165.53, 164.82, 158.27, 155.19, 149.35, 147.77, 145.13, 137.08, 135.71, 130.10, 124.34, 121.66, 120.59, 117.44, 57.42, 52.64, 49.42, 48.51, 35.14, 33.11, 31.91, 30.97, 26.62, 25.81, 24.89, 22.19, 11.89.

¹H NMR (CDCl₃, 400 MHz) δ 7.89-7.84 (m, 2H), 7.60-7.50 (m, 3H), 4.78 (s, 2H), 4.49 (d, J=7.6 Hz, 1H), 3.16-2.96 (m, 2H), 2.70-2.20 (m, 8H), 2.00-1.60 (m, 6H), 1.46-1.10 (m, 9H), 0.84 (t, J=7.2 Hz, 3H); ¹³C NMR (CDCl₃, 100 MHz) δ 165.49, 145.13, 141.50, 132.45, 129.06, 126.87, 57.35, 53.26, 52.61, 48.38, 34.63, 34.05, 31.92, 31.87, 26.64, 25.86, 24.82, 22.23, 11.84.

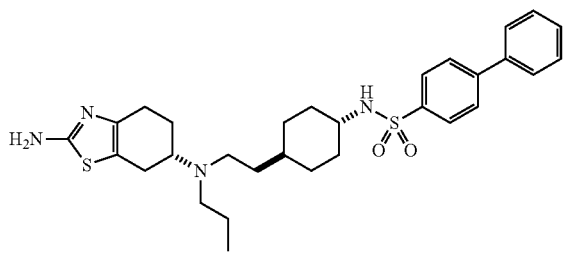

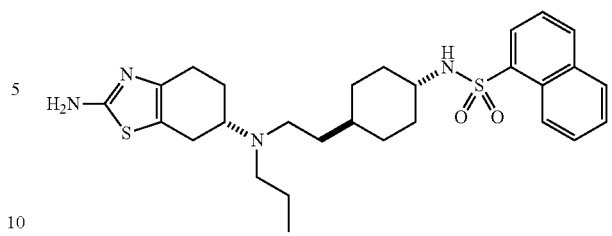

¹H NMR (CDCl₃, 400 MHz) δ 7.94 (d, J=8.4 Hz, 2H), 7.80-7.60 (m, 4H), 7.58-7.40 (m, 3H), 5.42 (s, 1H), 5.05 (s, 2H), 3.20-2.96 (m, 2H), 2.70-2.30 (m, 8H), 2.00-1.60 (m, 6H), 1.46-1.10 (m, 9H), 0.86 (t, J=7.2 Hz, 3H); ¹³C NMR (CDCl₃, 100 MHz) δ 165.97, 145.20, 144.92, 140.18, 139.34, 132.31, 129.08, 128.48, 127.66, 127.41, 117.17, 57.22, 53.27, 52.55, 48.29, 34.53, 33.96, 32.02, 31.83, 26.72, 26.02, 24.53, 22.18, 11.89.

¹H NMR (CDCl₃, 400 MHz) δ 8.65 (d, J=8.0 Hz, 1H), 8.30 (d, J=8.0 Hz, 1H), 8.06 (d, J=8.0 Hz, 1H), 7.95 (d, J=8.0 Hz, 1H), 7.70-7.50 (m, 3H), 5.19 (d, J=7.6 Hz, 1H), 4.92 (s, 2H), 3.18-2.90 (m, 2H), 2.70-2.30 (m, 8H), 1.96-1.82 (m, 1H), 1.75-1.58 (m, 5H), 1.42-0.80 (m, 9H), 0.83 (t, J=7.2 Hz, 3H); ¹³C NMR (CDCl₃, 100 MHz) δ 165.71, 145.05, 135.95, 134.25, 134.11, 129.32, 129.11, 128.19, 128.14, 126.79, 124.52, 124.23, 117.37, 57.25, 53.38, 52.57, 48.29, 35.85, 34.55, 33.94, 31.93, 26.68, 25.93, 24.69, 22.25, 11.86.

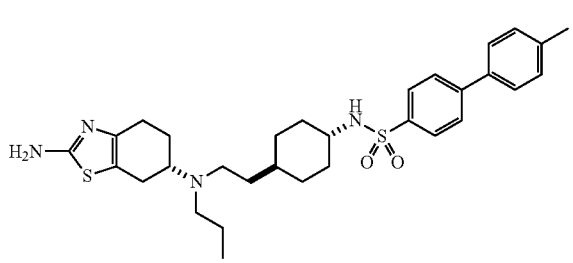

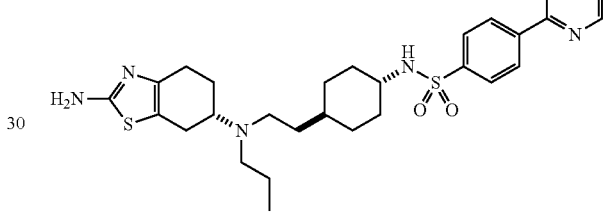

¹H NMR (CDCl₃, 400 MHz) δ 7.92 td, J=8.8 Hz, 2H), 7.67 (d, J=8.8 Hz, 2H), 7.0 (d, J=8.0 Hz, 2H), 7.27 (d, J=8.0 Hz, 2H), 5.68 (s, 1H), 5.28 (s, 2H), 3.18-2.90 (m, 2H), 2.70-2.30 (m, 8H), 2.33 (s, 3H), 1.96-1.60 (m, 6H), 1.42-1.15 (m, 9H), 0.82 (t, J=7.2 Hz, 3H); ¹³C NMR (CDCl₃, 100 MHz) δ 166.19, 145.08, 144.82, 139.86, 138.46, 136.40, 129.79, 127.38, 127.36, 127.14, 117.00, 57.20, 53.25, 52.54, 48.30, 35.79, 34.53, 33.91, 32.05, 26.72, 26.03, 24.53, 22.21, 21.24, 11.92.

¹H NMR (CDCl₃, 400 MHz) δ 8.83 (d, J=4.8 Hz, 2H), 8.55 (d, J=8.8 Hz, 2H), 8.06-7.95 (m, 2H), 7.30-7.22 (m, 1H), 5.57 (s, 1H), 5.11 (s, 2H), 3.18-2.95 (m, 2H), 2.70-2.30 (m, 8H), 1.96-1.85 (m, 1H), 1.82-1.60 (m, 5H), 1.46-0.80 (m, 9H), 0.83 (t, J=7.2 Hz, 3H); ¹³C NMR (CDCl₃, 100 MHz) δ 166.09, 163.23, 157.46, 144.83, 143.44, 141.21, 128.76, 127.13, 119.96, 57.47, 53.31, 52.54, 48.35, 34.53, 33.88, 31.95, 31.80, 26.59, 25.84, 24.57, 21.87, 11.80.

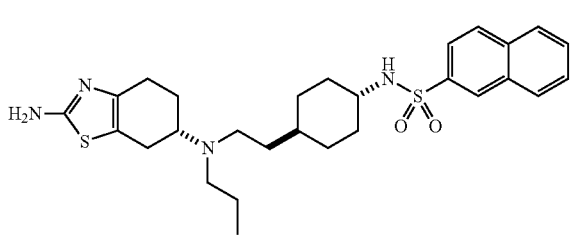

¹H NMR (CDCl₃, 400 MHz) δ 8.47 (s, 1H), 8.00-7.82 (m, 4H), 7.70-7.60 (m, 2H), 5.20 (d, J=7.2 Hz, 1H), 4.93 (s, 2H), 3.20-2.90 (m, 2H), 2.70-2.30 (m, 8H), 1.96-1.60 (m, 6H), 1.42-1.15 (m, 9H), 0.82 (t, J=7.2 Hz, 3H); ¹³C NMR (CDCl₃, 100 MHz) δ 165.73, 145.05, 138.32, 134.71, 132.17, 129.45, 129.29, 128.68, 128.10, 127.93, 127.50, 122.37, 117.42, 57.21, 53.27, 52.55, 48.28, 35.84, 34.53, 34.04, 31.97, 26.72, 26.00, 24.62, 22.26, 11.87.

¹H NMR (CDCl₃, 400 MHz) δ 8.98 (d, J=1.6 Hz, 1H), 8.80 (d, J=4.8 Hz, 2H), 8.62 (d, J=8.0 Hz, 1H), 7.99 (d, J=8.0 Hz, 1H), 7.59 (t, J=8.0 Hz, 1H), 7.23 (t, J=4.8 Hz, 1H), 5.53 (s, 1H), 5.12 (s, 2H), 3.18-2.90 (m, 2H), 2.70-2.30 (m, 8H), 1.96-1.80 (m, 3H), 1.70-1.58 (m, 3H), 1.42-0.80 (m, 9H), 0.82 (t, J=7.2 Hz, 3H); ¹³C NMR (CDCl₃, 100 MHz) δ 166.04, 163.10, 157.41, 144.91, 142.41, 138.70, 131.72, 129.32, 128.78, 126.64, 119.85, 117.01, 57.33, 53.29, 52.56, 48.33, 35.75, 34.56, 33.92, 31.97, 26.66, 25.96, 24.67, 22.14, 11.83.

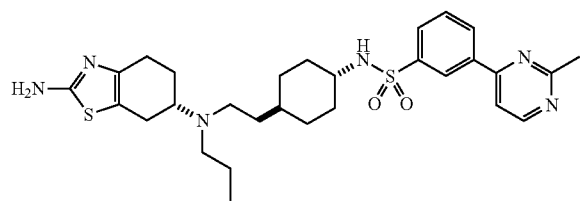

¹H NMR (CDCl₃, 400 MHz) δ 8.74 (d, J=4.0 Hz, 1H), 8.58 (s, 1H), 8.30 (d, J=8.0 Hz, 1H), 7.99 (d, J=8.0 Hz, 1H), 7.69-7.20 (m, 2H), 4.72 (s, 2H), 4.60 (d, J=8.0 Hz, 1H), 3.18-2.90 (m, 2H), 2.81 (s, 3H), 2.70-2.30 (m, 8H), 1.96-1.55 (m, 6H), 1.42-0.80 (m, 9H), 0.84 (t, J=7.6 Hz, 3H); ¹³C NMR (CDCl₃, 100 MHz) δ 168.79, 165.39, 162.14, 158.00, 145.16, 142.60, 138.13, 130.94, 129.79, 128.81, 125.58, 114.00, 57.31, 53.41, 52.58, 48.34, 34.59, 34.10, 31.90, 29.71, 26.27, 24.81, 22.28, 11.83.

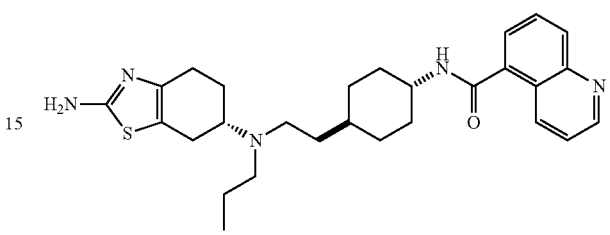

¹H NMR (CDCl₃, 400 MHz) δ 7.62 (d, J=8.4 Hz, 2H), 750-7.22 (m, 5H), 5.92 (d, J=8.0 Hz, 1H), 4.89 (s, 2H), 3.98-3.84 (m, 1H), 3.08-3.00 (m, 1H), 2.76-2.40 (m, 8H), 2.18-1.62 (m, 6H), 1.50-1.10 (m, 9H), 0.88 (t, J=7.6 Hz, 3H); ¹³C NMR (CDCl₃, 100 MHz) δ 165.55, 161.07, 148.55, 145.18, 138.02, 133.58, 129.06, 128.70, 128.46, 126.07, 123.34, 117.55, 57.40, 52.67, 49.27, 48.52, 36.12, 35.15, 33.21, 31.96, 26.66, 25.89, 24.94, 22.31, 11.89.

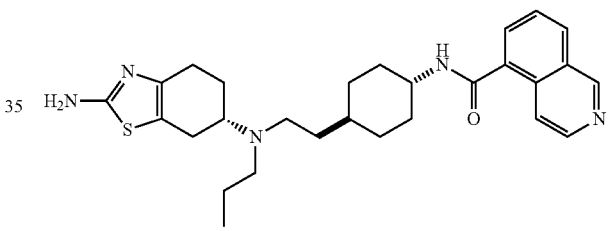

¹H NMR (CDCl₃, 400 MHz) δ 7.60-7.30 (m, 9H), 5.35 (d, J=8.0 Hz, 1H), 4.93 (s, 2H), 3.80-3.63 (m, 1H), 3.59 (s, 2H), 3.08-2.95 (m, 1H), 2.76-2.40 (m, 8H), 2.00-1.85 (m, 3H), 1.80-1.60 (m, 3H), 1.50-1.10 (m, 9H), 0.84 (t, J=7.6 Hz, 3H); ¹³C NMR (CDCl₃, 100 MHz) δ 170.10, 165.59, 145.14, 140.55, 140.12, 134.13, 129.83, 128.86, 127.65, 127.44, 127.02, 117.46, 57.33, 52.60, 48.83, 48.43, 43.59, 36.04, 34.98, 32.95, 31.96, 31.84, 26.65, 25.86, 24.87, 22.29, 11.89.

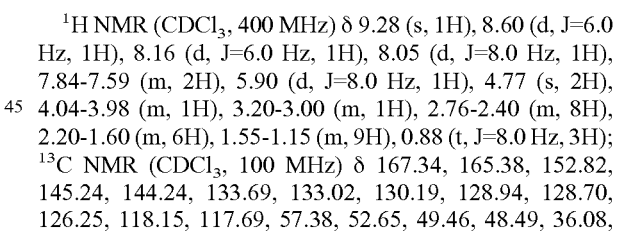

¹H NMR (CDCl₃, 400 MHz) δ 8.31-8.28 (m, 2H), 8.11 (d, J=8.0 Hz, 2H), 7.75 (d, J=8.0 Hz, 1H), 7.76-7.59 (m, 2H), 4.70 (s, 2H), 4.04-3.93 (m, 1H), 3.20-3.00 (m, 1H), 2.76-2.40 (m, 8H), 2.20-1.85 (m, 3H), 1.80-1.10 (m, 12H), 0.90 (t, J=8.0 Hz, 3H); ¹³C NMR (CDCl₃, 100 MHz) δ 187.41, 165.34, 163.58, 150.10, 146.48, 145.24, 137.41, 130.00, 129.66, 129.28, 127.76, 120.71, 118.91, 57.52, 52.68, 48.86, 48.60, 35.21, 33.09, 32.02, 26.62, 25.76, 24.93, 22.17, 11.87.

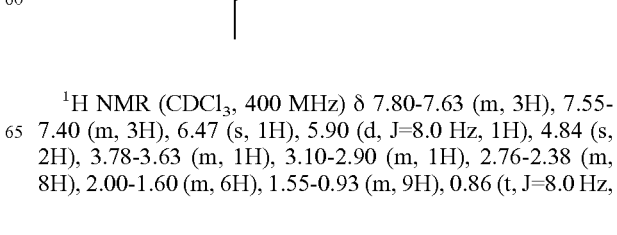

¹H NMR (CDCl₃, 400 MHz) δ 8.93-8.68 (m, 2H), 8.13 (dd, J=7.6, 1.2 Hz, 1H), 7.67-7.43 (m, 3H), 6.05 (d, J=8.0 Hz, 1H), 4.92 (s, 2H), 4.04-3.93 (m, 1H), 3.20-3.00 (m, 1H), 2.76-2.38 (m, 8H), 2.20-1.60 (m, 6H), 1.55-1.10 (m, 9H), 0.88 (t, J=8.0 Hz, 3H); ¹³C NMR (CDCl₃, 100 MHz) δ 167.62, 165.54, 150.88, 148.17, 145.16, 134.82, 134.17, 131.99, 128.23, 125.72, 125.11, 121.94, 117.49, 57.35, 52.63, 49.39, 48.48, 36.09, 35.12, 33.18, 31.94, 26.66, 25.88, 24.88, 22.32, 11.92.

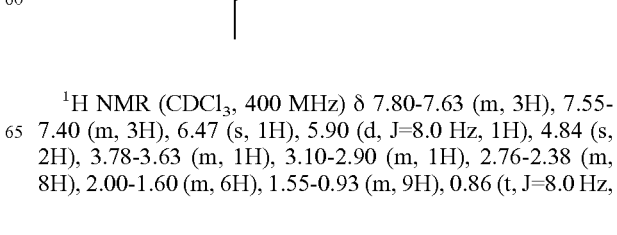

¹H NMR (CDCl₃, 400 MHz) δ 9.28 (s, 1H), 8.60 (d, J=6.0 Hz, 1H), 8.16 (d, J=6.0 Hz, 1H), 8.05 (d, J=8.0 Hz, 1H), 7.84-7.59 (m, 2H), 5.90 (d, J=8.0 Hz, 1H), 4.77 (s, 2H), 4.04-3.98 (m, 1H), 3.20-3.00 (m, 1H), 2.76-2.40 (m, 8H), 2.20-1.60 (m, 6H), 1.55-1.15 (m, 9H), 0.88 (t, J=8.0 Hz, 3H); ¹³C NMR (CDCl₃, 100 MHz) δ 167.34, 165.38, 152.82, 145.24, 144.24, 133.69, 133.02, 130.19, 128.94, 128.70, 126.25, 118.15, 117.69, 57.38, 52.65, 49.46, 48.49, 36.08, 35.15, 33.23, 31.92, 26.67, 25.88, 24.94, 22.32, 11.89.

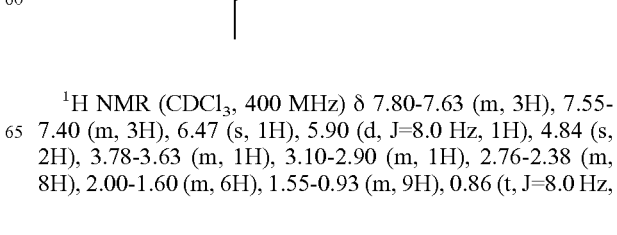

¹H NMR (CDCl₃, 400 MHz) δ 7.80-7.63 (m, 3H), 7.55-7.40 (m, 3H), 6.47 (s, 1H), 5.90 (d, J=8.0 Hz, 1H), 4.84 (s, 2H), 3.78-3.63 (m, 1H), 3.10-2.90 (m, 1H), 2.76-2.38 (m, 8H), 2.00-1.60 (m, 6H), 1.55-0.93 (m, 9H), 0.86 (t, J=8.0 Hz,

3H); $^{13}$C NMR (CDCl$_3$, 100 MHz) δ 165.74, 165.44, 145.19, 141.05, 137.35, 133.39, 131.78, 130.82, 129.91, 129.02, 126.71, 117.59, 107.38, 57.37, 52.64, 49.07, 48.53, 36.10, 35.06, 32.56, 31.81, 26.66, 25.88, 24.89, 22.32, 11.90.

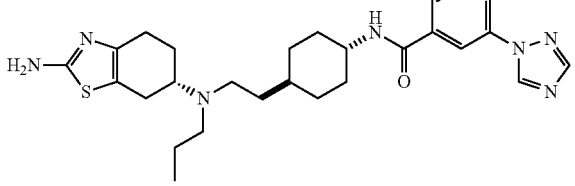

$^1$H NMR (CDCl$_3$, 400 MHz) δ 8.65 (s, 1H), 8.11 (s, 1H), 8.12-8.10 (m, 2H), 7.84-7.55 (m, 3H), 6.20 (d, J=7.6 Hz, 1H), 4.88 (s, 2H), 4.00-3.88 (m, 1H), 3.16-2.98 (m, 1H), 2.76-2.40 (m, 8H), 2.16-1.60 (m, 6H), 1.55-1.10 (m, 9H), 0.86 (t, J=7.6 Hz, 3H); $^{13}$C NMR (CDCl$_3$, 100 MHz) δ 165.50, 165.29, 152.81, 145.18, 141.09, 137.19, 136.86, 130.12, 126.37, 122.48, 118.51, 117.55, 57.37, 52.65, 49.51, 48.49, 36.09, 35.15, 33.11, 31.93, 26.65, 25.86, 24.91, 22.29, 11.90.

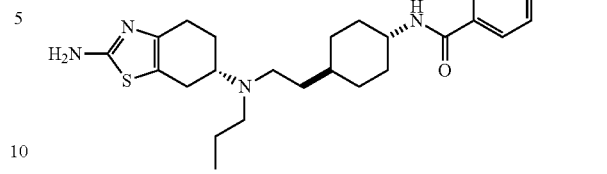

$^1$H NMR (CDCl$_3$, 400 MHz) δ 7.88 (d, J=6.8 Hz, 2H), 7.72 (d, J=7.2 Hz, 1H), 7.54-7.49 (m, 2H), 7.32 (s, 1H), 7.18 (s, 1H), 6.60 (d, J=8.0 Hz, 1H), 5.02 (s, 2H), 4.00-3.86 (m, 1H), 3.16-2.98 (m, 1H), 2.76-2.40 (m, 8H), 2.16-1.60 (m, 6H), 1.55-1.10 (m, 9H), 0.85 (t, J=7.6 Hz, 3H); $^{13}$C NMR (CDCl$_3$, 100 MHz) δ 165.68, 165.46, 145.09, 137.54, 137.02, 135.55, 130.59, 130.04, 125.58, 123.78, 120.46, 118.23, 117.34, 57.34, 52.65, 49.51, 48.49, 36.10, 35.14, 33.03, 31.97, 26.64, 25.86, 24.92, 22.27, 11.90.

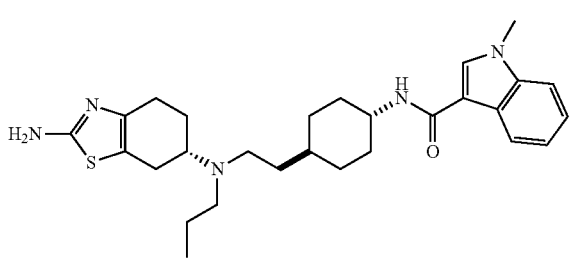

$^1$H NMR (CDCl$_3$, 400 MHz) δ 7.92 (dd, J=7.2, 1.6 Hz, 1H), 7.65 (s, 1H), 7.40-7.24 (m, 3H), 5.80 (d, J=8.0 Hz, 1H), 4.88 (s, 2H), 4.10-3.86 (m, 1H), 3.82 (s, 3H), 3.16-2.98 (m, 1H), 2.76-2.40 (m, 8H), 2.20-1.64 (m, 6H), 1.55-1.30 (m, 9H), 0.88 (t, J=7.6 Hz, 3H); $^{13}$C NMR (CDCl$_3$, 100 MHz) δ 165.52, 164.38, 145.18, 137.24, 132.23, 125.27, 122.45, 121.30, 119.99, 117.59, 111.22, 110.09, 57.40, 52.66, 48.55, 48.53, 36.17, 35.25, 33.59, 33.23, 32.08, 26.67, 25.91, 24.94, 22.33, 11.91.

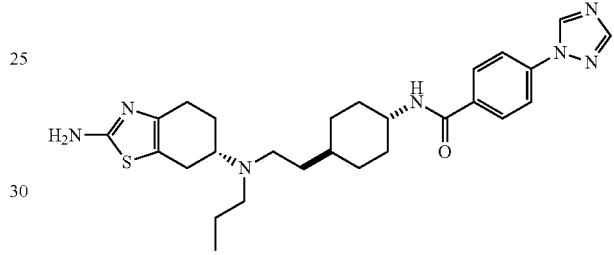

$^1$H NMR (CDCl$_3$, 400 MHz) δ 7.97 (d, J=2.4 Hz, 1H), 7.85 (d, J=8.8 Hz, 2H), 7.80-7.74 (m, 3H), 6.49 (t, J=2.4 Hz, 1H), 6.11 (d, J=8.0 Hz, 1H), 4.94 (s, 2H), 4.00-3.84 (m, 1H), 3.10-2.96 (m, 1H), 2.76-2.40 (m, 8H), 2.16-1.60 (m, 6H), 1.55-1.20 (m, 9H), 0.86 (t, J=7.6 Hz, 3H); $^{13}$C NMR (CDCl$_3$, 100 MHz) δ 165.78, 165.60, 145.15, 142.11, 141.73, 132.63, 128.37, 126.84, 118.55, 117.47, 108.29, 57.40, 52.66, 49.32, 48.52, 36.13, 35.18, 33.18, 31.97, 26.65, 25.89, 24.94, 22.30, 11.89.

$^1$H NMR (CDCl$_3$, 400 MHz) δ 8.63 (s, 1H), 8.12 (s, 1H), 7.90 (d, J=8.8 Hz, 2H), 7.74 (d, J=8.8 Hz, 2H), 6.16 (d, J=8.0 Hz, 1H), 4.96 (s, 2H), 4.00-3.84 (m, 1H), 3.30-2.96 (m, 1H), 2.76-2.40 (m, 8H), 2.16-1.60 (m, 6H), 1.55-1.10 (m, 9H), 0.85 (t, J=7.6 Hz, 3H); $^{13}$C NMR (CDCl$_3$, 100 MHz) δ 165.63, 165.38, 152.89, 145.13, 140.98, 138.91, 134.56, 128.68, 119.55, 117.42, 57.39, 52.65, 49.46, 48.49, 36.09, 35.15, 33.14, 31.93, 26.63, 25.86, 24.93, 22.28, 11.88.

Compounds having an affinity for the dopamine D3 receptor have been disclosed, for example, in WO 95/04713, WO 96/23760, WO 97/45503, WO 98/27081, WO 99/58499, WO 05/118588, WO 06/040182, WO 06/082456, WO 06/066885, and WO 08/026,046. Some of these compounds possess moderate affinities and/or selectivities for the dopamine D$_3$ receptor, and therefore have been proposed as suitable for treating diseases of the central nervous system. Unfortunately, the affinity and selectivity of these compounds towards the D$_3$ receptor and/or their pharmacological profile are not satisfactory. Consequently, there is an ongoing need to provide new compounds that preferably have a high affinity for the D$_3$ receptor and an improved selectivity. The compounds also should have a good pharmacological profile, e.g., a high brain plasma ratio, a high bioavailability, a good metabolic stability, and/or a decreased inhibition of the mitochondrial respiration.

The present compounds exhibit these beneficial properties. In particular, crystal structures for the human β2 adrenergic (β2AD) G-protein coupled receptor (GPCR) were solved (26, 27). The human D$_3$ receptor structure was modeled upon the high-resolution crystal structures of β2AD receptor because these two proteins belong to the same GPCR sub-family (28) and share close sequence homology. Because the crystal structure of β2AD receptor was solved with an inverse agonist bound to it, a modeled D$_3$ structure (FIG. 1) is theorized, but not relied upon, to represent the conformational state bound to either antagonists or inverse agonists.

The binding of pramipexole (compound 1) to the $D_3$ receptor structure was modeled through computational docking, followed by extensive refinement. The predicted model (FIG. 1) showed that the primary amino group in the thiazole ring of compound 1 forms a hydrogen bonding network with the hydroxyl groups of Ser192 and Ser193. The thiazole ring in compound 1 is parallel to the imidazole ring in His349, thereby providing a favorable π-π stacking interaction. The protonated nitrogen in compound 1 forms a salt bridge with the negatively charged Asp110. The n-propyl group in compound 1 inserts into a hydrophobic channel formed by Cys114, Phe345, Phe346, Trp342 and Try373.

FIG. 1 shows the predicted binding model of compound 1 to the human $D_3$ receptor. Side chains of crucial residues in the binding site are shown as stick and labeled. Hydrogen bonds between compound 1 and $D_3$ are depicted in dotted lines. Figures were generated by Pymol.

The predicted model of compound 1 complexed with the $D_3$ receptor suggested ample available room to accommodate a larger hydrophobic group where the n-propyl group in compound 1 binds. In the adjacent area is another well-defined, but smaller, hydrophobic cavity formed by Cys114, Phe197, and Trp342 residues. Compound 5 (comparative) therefore was synthesized to explore the interactions with these two pockets.

Compound 5 was tested for its binding affinities to the dopamine receptors using the same methods as described previously (See Table 1 below) (21). It was found that compound 5 has a $K_i$ value of 0.043 nM to the $D_3$ receptor, being 18-times more potent than compound 1. Compound 5, however, also potently binds to the high affinity state of the $D_2$ receptor with a $K_i$ value of 2.7 nM, thus displaying a 62-fold selectivity for the $D_3$ receptor over the $D_2$ receptor. Similar to compound 1, compound 5 has a weak affinity to the $D_1$-like receptors and has a $K_i$ value of 11,000 nM. Although compound 5 has a very high affinity to the $D_3$ receptor, its selectivity over the $D_2$ receptor is modest.

Table 1 summarizes the binding affinities at the $D_1$-like, $D_2$, and $D_3$ receptors in binding assays using rat brain. Data represent the mean±SEM of three to five independent determinations. For compounds producing a 2-site fit in competition with [$^3$H]-spiperone, $K_i$ values are presented for the high and low affinity components and are indicated by the designation "(h)" or "(l)". All other $K_i$ values are based on a single-site model.

In a design of prior art compound 4, it was shown that introduction of a trans-cyclohexyl group into the linker region yielded ligands with much improved selectivity for the $D_3$ receptor over the $D_2$ receptor compared to a linear 4-carbon linker. Therefore, compound 6 was designed to investigate whether introduction of a rigid cyclohexyl group into compound 5 may improve the selectivity. Compound 6 binds to the $D_3$ and $D_2$ receptors with $K_i$ values of 0.40 nM and 307 nM, respectively. Hence, compound 6 is a potent $D_3$ ligand and displays an excellent selectivity of 763-fold for the $D_3$ receptor over the $D_2$ receptor.

Compounds 7-10 then were designed and synthesized to investigate the effect of the n-propyl group of compound 6 on binding and selectivity. Compound 7, with an n-butyl group, has a slightly weaker affinity for the $D_3$ receptor than compound 6, and exhibited a 2-site competition curve at the $D_2$ receptor, with roughly a 10-fold less selectivity for the $D_3$ receptor over the $D_2$ receptor with a high affinity binding component. Compound 8, with an isopentyl group, is 5-times less potent than compound 6 to the $D_3$ receptor, but has a similar binding affinity to the $D_2$ receptor. Compound 9, with a bulky cyclohexylethyl group, is 55-times less potent than compound 6 to the $D_3$ receptor, but is only 3-times less potent than compound 6 to the $D_2$ receptor. Compound 10, with a hydrogen atom at this site, has a $K_i$ value of 7.6 nM to the $D_3$ receptor, being 19-times less potent than compound 6, but their binding affinity to the $D_2$ receptor are essentially the same. Therefore, binding data suggests, but is not relied upon, that substitution on this nitrogen atom has a major effect on binding to the $D_3$ receptor, but modest influence on binding to the $D_2$ receptor. The data shows that the n-propyl group in compound 6 enhances the binding affinity to the $D_3$-receptor by 19-fold compared to the hydrogen atom in compound 10.

The influence of the naphthyl group in compound 6 on binding and selectivity also was investigated. Compound 11, in which the naphthyl group is replaced by a 2-benzofuran, binds to the $D_3$ receptor with the same affinity ($K_i$=0.5 nM) as compound 6, but its selectivity over the $D_2$ receptor is decreased to 133-fold, due to an increased binding affinity to the $D_2$ receptor. Compound 12, in which a cinnamyl group replaces the naphthyl group, retains a high binding affinity for the $D_3$-receptor $K_i$=0.41 nM) and displays 800- and >30,000-fold selectivity over the $D_2$ and $D_1$-like receptors. These data suggest, but not relied upon, that the modifications of the naphthyl group can have a significant effect on the selectivity.

TABLE 1

| Compound No. | $K_i$ ± SEM (nM) | | | Selectivity | |
| --- | --- | --- | --- | --- | --- |
| | $D_3$ [$^3$H]PD128907 | $D_2$ [$^3$H]Spiperone | $D_1$-like [$^3$H]SCH23390 | $D_2$-like/ $D_3$ | $D_1$-like/ $D_3$ |
| 1 (pramipexole) | 0.78 | 3.1 ± 0.3 (h) 6400 ± 1700 (l) | >100,000 | 4 | >100,000 |
| 4 (prior art) | 5.7 ± 0.4 | >10000 | >50000 | >1000 | >5000 |
| 5 (comparative) | 0.043 ± 0.006 | 2.7 ± 0.4 (h) 6700 ± 1500 (l) | 11,000 ± 500 | 62 | >100,000 |
| 6 | 0.40 ± 0.057 | 307 ± 38 | 3,400 ± 300 | 763 | >7,000 |
| 7 | 0.74 ± 0.083 | 55 ± 12 (h) 1300 ± 180 (l) | 5,400 ± 500 | 74 | >7,000 |
| 8 | 2.2 ± 0.10 | 345 ± 33 | 13,000 ± 1,000 | 157 | >5,000 |
| 9 (comparative) | 23 ± 2.7 | 1,200 ± 170 | 4,400 ± 800 | 53 | 194 |
| 10 (intermediate) | 7.6 ± 0.87 | 670 ± 140 | 64,000 ± 7,000 | 88 | >8,000 |
| 11 | 0.51 ± 0.10 | 68 ± 4.6 | 4,900 ± 600 | 133 | >9,000 |
| 12 | 0.41 ± 0.031 | 330 ± 69 | 13,000 ± 1,700 | 800 | >30,000 |

Compounds 5, 6, and 12 have good aqueous solubility. For example, the dihydrochloride salt form of compound 6 has an aqueous solubility greater than 100 mg/ml. This excellent aqueous solubility provides an ability to evaluate an in vivo functional profiles in animals.

Recently, in vivo functional assays for the $D_3$ and $D_2$ receptors have been validated. (24,25). Yawning in rats provides a sensitive measure of in vivo agonist activity at the dopamine $D_3$ receptor (24,25), while the induction of hypothermia has been shown to be mediated by agonist activity at the $D_2$ receptor (32,33). By employing these validated assays, compounds 5, 6, and 12 were evaluated for their in vivo functional activity at the $D_3$ and $D_2$ receptors. Compound 1, a known $D_3$ and $D_2$ agonist, was used as a control in the evaluations. The results are summarized in FIG. 2.

Figure 2A:
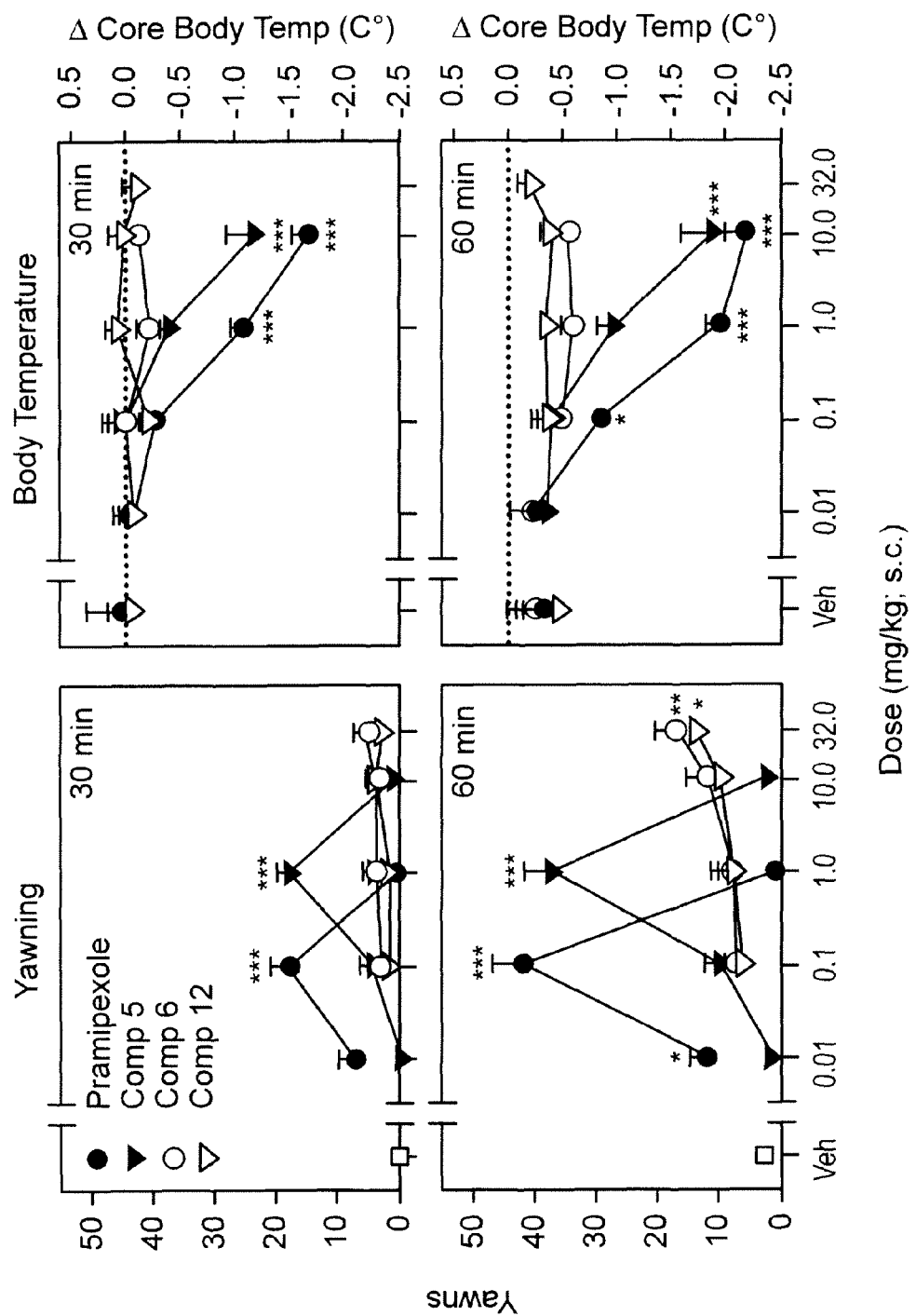
FIG. 2 contains graphs (a) illustrating the yawning and body temperature of rats treated with compounds 1, 5, 6, and 12 at 30 and 60 minutes, and (b) yawns/30 minutes and body temperature for rats treated with compound 1 and either vehicle or 10.0 or 32.0 mg/kg of compound 12.

FIG. 2 illustrates the functional evaluations of the $D_3$ and $D_2$ activity of pramipexole and compounds 5, 6, and 12 in yawning and hypothermia assays in rats. The top and middle panels of FIG. 2 (a) show induction of yawning or hypothermia by $D_3$ ligands. The bottom panels of FIG. 2 (b) show effects of pramipexole and compound 12 in yawning and hypothermia assays.

As seen in FIG. 2, and consistent with data obtained in previous studies (24,25), increases in yawning were observed over low doses (0.01 to 0.1 mg/kg) of compound 1 with inhibition of yawning, and the induction of hypothermia occurring at higher doses. These data indicate that compound 1 functions as a preferential $D_3$ agonist in vivo and a $D_2$ agonist at higher doses.

Figure 3:
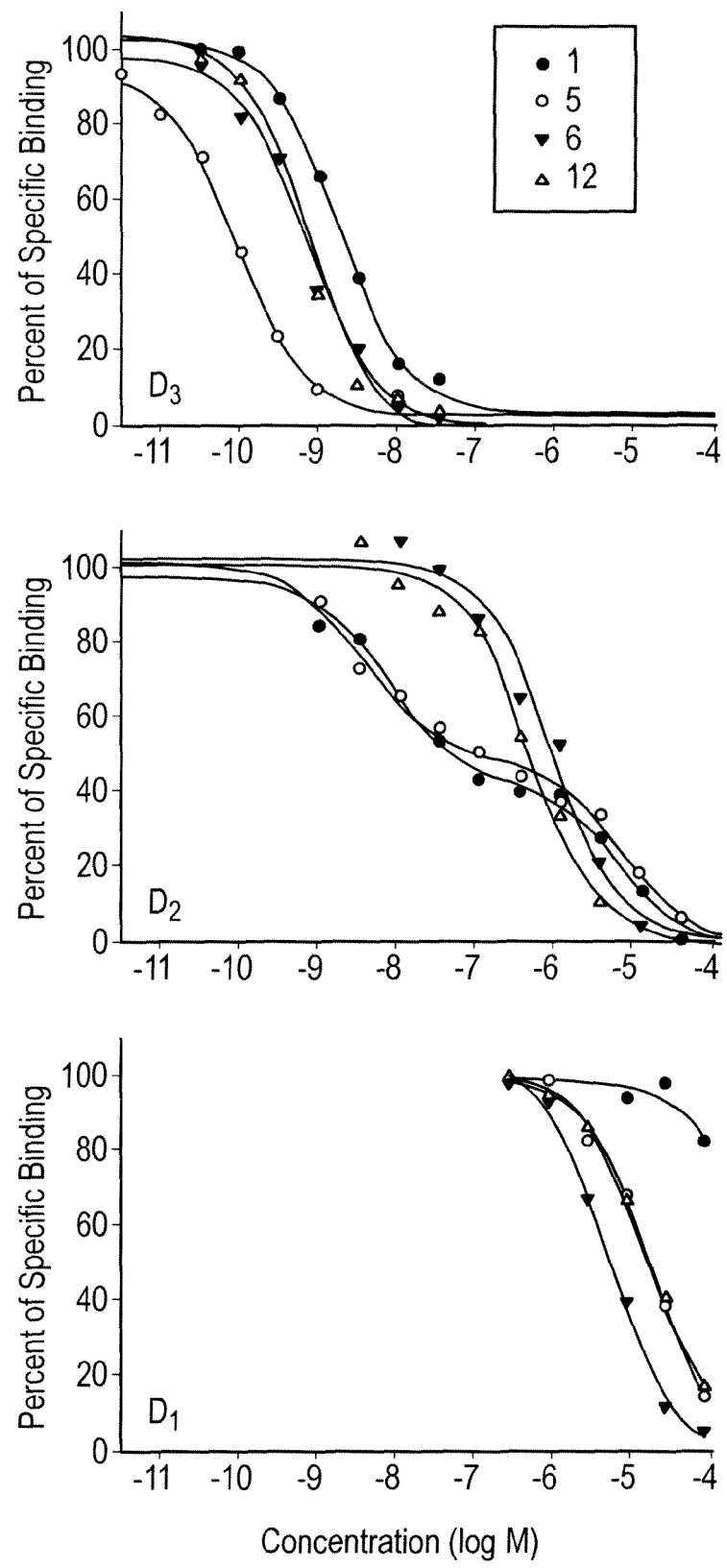
FIG. 3 contains competitive binding curves for compounds 1, 5, 6, and 12 in an in vitro binding assay.

Compound 5 induced yawning and produced an inverted U-shaped dose-response curve. The maximum levels of yawning induced by compound 5 are very similar to that induced by compound 1. Further more, hypothermia was induced by compound 5 at higher doses, concurrent with decreases in yawning. These data show that compound 5 functions as a full agonist at the $D_3$ and $D_2$ receptors in vivo, consistent with the 2-site competition curve observed in the [$^3$H]spiperone binding assay for compound 1 and compound 5 (FIG. 3). Furthermore, the in vivo data suggest that compound 5 is bioavailable.

Unlike compounds 1 and 5, the dose-response curves for compounds 6 and 12 induced yawning were relatively flat, and failed to reach significance during the initial 30 minute observation period. While significant levels of yawning induced by compounds 6 and 12 were observed after 60 minutes, the dose-response curves for both compounds remained relatively flat. Moreover, compounds 6 and 12 failed to induce changes in body temperature over the initial hour of observation, an effect that is indicative of $D_2$ agonist activity. Together, the low levels of yawning, combined with the absence of any hypothermic effect suggest that compounds 6 and 12 function as weak partial agonists at the $D_3$ receptor, with no detectable agonist activity at the $D_2$ receptor.

Figure 2B:
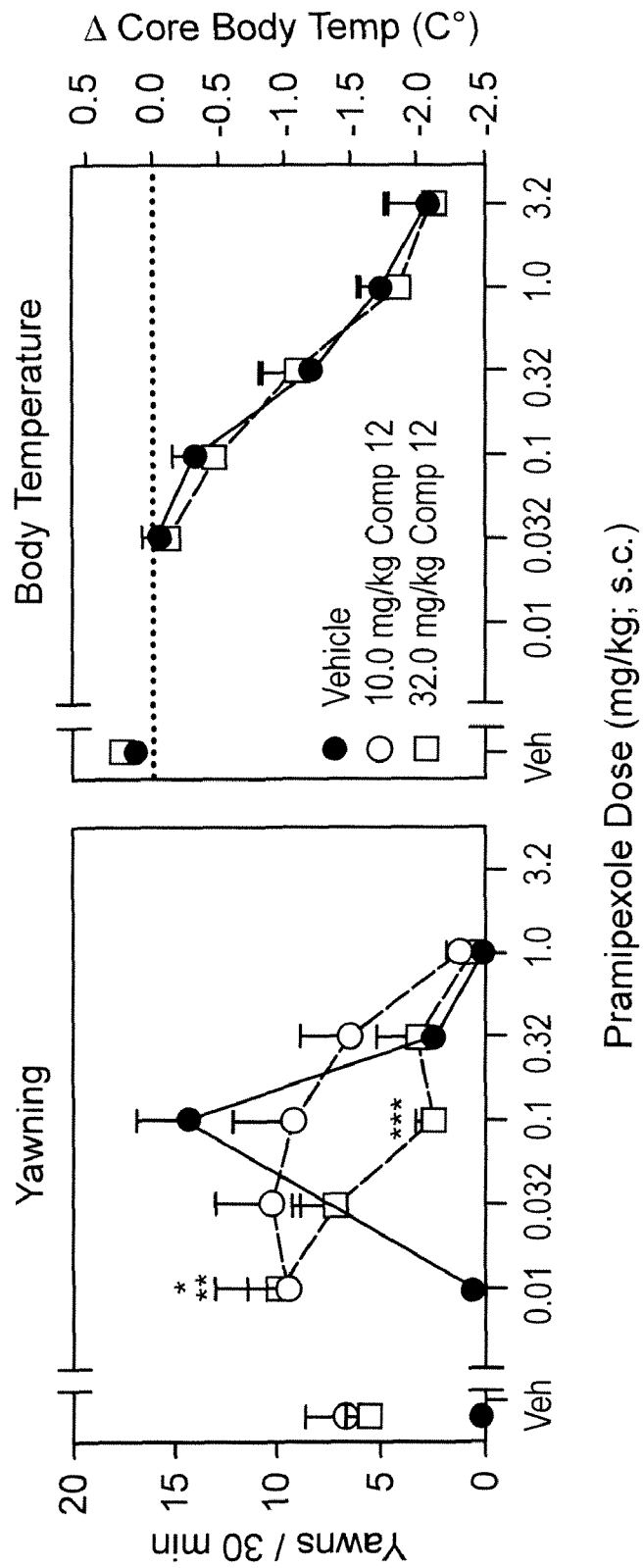

The ability of compound 12 to alter pramipexole induced yawning and hypothermia was evaluated and the data are shown in FIG. 2(b). Similar to the effects of compound 12 alone, but unlike the effects of $D_3$-selective antagonists, low levels of yawning were observed during the initial 30 minutes after administration of either 10.0 or 32.0 mg/kg of compound 12. This effect persisted upon administration of low doses of pramipexole as significant increases in yawning were observed when rats were pretreated with compound 12 (10.0 or 32.0 mg/kg). However, compound 12 resulted in a dose-dependent decrease in the amount of yawning observed following the maximally effective dose of pramipexole at 0.1 mg/kg. No significant effects of compound 12 were observed at higher doses of pramipexole (0.32 and 1 mg/kg). These data suggest that compound 12 is capable of antagonizing the $D_3$-mediated effects of pramipexole.

However, the profile of activity for compound 12 is different from that observed for selective $D_3$ antagonists, which generally produce selective rightward and/or downward shifts of the ascending limb of the yawning dose-response curve for $D_3$-preferring agonists without increasing the amount of yawning observed at low doses. In fact, the effects of compound 12 alone, and in combination with pramipexole, suggest that it is more similar to the partial agonist, aripiprazole, than an antagonist. Moreover, compound 12 failed to alter the induction of hypothermia by pramipexole, an effect that is indicative of $D_2$ agonist activity, which can be reliably blocked by both selective and non-selective $D_2$ antagonists (32,33). Together, the data provides evidence that compound 12 is a partial agonist at the $D_3$ receptor with no detectable agonist or antagonist activity at the $D_2$ receptor, thus possessing a novel in vivo functional profile.

In summary, a series of enantiomerically pure compounds of structural formula (I) have been synthesized, and their binding and selectivity to the $D_3$, $D_1$-like and $D_2$ receptor has been evaluated. The present invention therefore identifies several potent and highly selective $D_3$ ligands with excellent aqueous solubility. In vivo functional evaluations show, for example, that while compound 5 functions as a full $D_3$ agonist, compound 12 behaves as a selective $D_3$ partial agonist with no activity at the $D_2$ receptor.

The present invention therefore is directed to a class of potent and selective $D_3$ ligands that are highly potent and selective for the $D_3$ receptor over the other dopamine receptor subtypes and that have a unique of pharmacological and behavioral profile. The present ligands have the therapeutic potential for the treatment of, for example, drug abuse, Parkinson's diseases, restless leg syndrome, and other conditions in which modulation of the $D_3$ receptor is desirable.

Experimental Protocols
Computational Modeling Methods

The human dopamine subtype 3 ($D_3$) receptor was homology-modeled using the crystal structure of human β2 Adrenergic (β2AD) receptor (PDB entry: 2RH1) at 2.4 Å resolution as the template (26). The sequence alignment used was based on sequence analysis of 493 members of the amine sub-family of GPCR proteins (35). Initial 3D models of the human $D_3$ were generated using the program Modeller (version 9v2) (36). The initial $D_3$ receptor models from Modeller then were inserted into a 2-palmitoyl-2-oleoyl-sn-glycero-3-phosphatidylcholine (POPC) membrane (37) in a TIP3 water environment. Molecular dynamic (MD) simulations were performed to further refine the modeled structures of the $D_3$ receptor using Gromacs (version 3.3.1) with united atom representation for the receptor (38).

For docking, all the binding poses of the compounds with the $D_3$ receptor were predicted using the GOLD program (version 3.1) (39,40). The center of the binding site for the $D_3$ receptor was set at center of the Asp110 with a radius of 13 Å, large enough to cover the binding pocket. For each genetic algorithm (GA) run, a maximum number of 200,000 operations were performed on a population of 5 islands of 100 individuals. Operator weights for crossover, mutation, and migration were set to 95, 95, and 10, respectively. The docking simulations were terminated after 10 runs for each compound. GoldScore implemented in Gold was used as the fitness function to evaluate the docked conformations. The ten conformations ranked highest by each fitness function were saved for analysis of the predicted docking modes. For the docking poses reported in FIG. 1, these were the highest ranked conformations from the docking simulations.

In Vitro Dopamine Receptor Binding Assays

Determination of $D_3$ dopamine receptor affinity and selectivity were performed in membranes prepared from the brains of adult, male Sprague-Dawley rats (Harlan Sprague-Dawley, Indianapolis, Ind.). All compounds were dissolved in 100% ethanol at a concentration of 5 mM.

[$^3$H]PD 128907 binding assays. [$^3$H]PD 128907 binding assays for D3 receptors dopamine receptors were performed as previously described in detail (30,31). Rat ventral striatum (nucleus accumbens and olfactory tubercles) was prepared in assay buffer (50 mM Tris, 1 mM EDTA; pH 7.4 at 23° C.) to yield a final concentration of 10 mg original wet weight (o.w.w.)/ml. Membranes were incubated with [$^3$H]PD 128907 (0.3 nM; 116 Ci/mmol; Amersham, Arlington Heights, Ill.) and various concentrations of competing compounds ($10^{-10}$ to $10^{-4}$ M). Nonspecific binding was defined by 1 μM spiperone. Assay tubes were incubated at 23° C. for 3 hours. The reaction was terminated by rapid vacuum filtration. Data were analyzed using SigmaPlot 8.0.2. using the $K_D$ value for [$^3$H]PD 128907 of 0.3 nM (30). $K_i$ values are expressed at the mean±SEM of 3-6 independent determinations.

[$^3$H]Spiperone binding assays. [$^3$H]spiperone binding assays for $D_2$-like receptors were performed as previously described in detail (29,31) and as described for [$^3$H]PD 128907 except for the following. Assays were performed using membranes prepared from rat caudate-putamen, which predominantly express the $D_2$ subtype of $D_2$-like receptors, and the final membrane homogenate concentration was 1.5 mg o.w.w./ml. The assay buffer was 50 mM Tris-HCl, 5 mM KCl, 2 mM $MgCl_2$, and 2 mM $CaCl_2$, pH 7.4 at 23° C.; the concentration of [$^3$H]spiperone (24 Ci/mmol; Amersham) was 0.2 nM; and the incubation time was 90 minutes at 23° C. Nonspecific binding was defined in the presence of 1 μM (+)-butaclamol. $K_i$ values were determined using the $K_D$ value for [$^3$H]spiperone of 0.1 nM (29).

[$^3$H]SCH 23390 binding assays. [$^3$H]SCH 23390 binding assays for $D_1$-like dopamine receptors were performed as previously described in detail (31) and as described for [$^3$H]spiperone binding, except the concentration of [$^3$H]SCH 23390 (73 Ci/mmol; Amersham) was 0.3 nM. $K_i$ values were determined using the $K_D$ value for [$^3$H]SCH 23390 of 0.3 nM (31).

The binding curves for compounds 1, 5, 6 and 12 are shown in FIG. 3.

In Vivo Yawning and Hypothermia Assays in Rats

Rats were purchased from Harlan (Indianapolis, Ind.) and housed three to a cage for yawning studies, and one to a cage for hypothermia studies. Rats used in the hypothermia studies had a radio-telemetric probe (E-4000 E-Mitter, Mini-Mitter, Bend, Oreg., USA) implanted into their peritoneal cavity, and were allowed 7 days to recover prior to experimentation as previously described (25). Yawning studies were performed as previously described (24,25), with yawning defined as a prolonged (about 1 second), wide opening of the mouth followed by a rapid closure. The capacity of pramipexole and other compounds investigated to induce yawning and hypothermia was assessed using a single dosing procedure (one dose per rat), with yawns recorded for a period of 60 minutes, and hypothermia for a period of 120 minutes after s.c. (1 ml/kg) administration of compounds. The capacity of CJ-1037 to alter the induction of yawning and hypothermia by pramipexole was assessed using a multiple dosing procedure in which rats were first treated with CJ-1037 (0.0, 10.0, or 32.0 mg/kg) followed by five successive doses of pramipexole each separated by 30 minutes. Yawning was recorded for 30 minutes after each injection. Determination of changes in core body temperature for compounds alone were determined by comparing body temperature 30 and 60 minutes after each single dose of compounds to that obtained 1 minute prior to injection of that compound, while the effects of compound 12 on pramipexole-induced hypothermia were determined by comparing the differences in core body temperature 30 minutes after each dose of compound 12 alone, or in combination with pramipexole to the body temperature obtained 1 min prior to the injection of compound 12. Yawns and changes in core body temperature are presented as the mean±standard error of the mean (SEM) with 8 (yawning) or 6 (hypothermia) rats per group. A one-way, repeated-measures ANOVA with post-hoc Dunnett's tests was used to determine significant changes in yawning or body temperature compared to vehicle treated animals, while significant effects of compound 12 on pramipexole-induced yawning and hypothermia were determined by two-way, repeated-measures ANOVA with post-hoc Bonferroni tests (GraphPad Prism; GraphPad Software Inc., San Diego, Calif.).

REFERENCES

1. J. N. Joyce, Dopamine D3 receptor as a therapeutic target for antipsychotic and antiparkinsonian drugs. *Pharmacol. Ther.* 2001, 90, 231-259.
2. M. Pilla et al., Selective inhibition of cocaine-seeking behaviour by a partial dopamine D3 receptor agonist. *Nature*, 1999, 400, 371-375.
3. G. F. Koob et al., Cocaine addition therapy—Are we partially there? *Nature Medicine*, 1999, 5, 993-995.
4. J. Montplaisir et al., Restless legs syndrome improved by pramipexole: a double-blind randomized trial. *Neurology* 1999, 52, 938-943.
5. B. Levant, The $D_3$ dopamine receptor: neurobiology and potential clinical relevance. *Pharmacol. Rev.* 1997, 49, 231-252.
6. A. H. Newman et al. Dopamine $D_3$ Receptor Partial Agonists and Antagonists as Potential Drug Abuse Therapeutic Agents. *J. Med. Chem.*, 2005, 48, 3663-3679.
7. P. Grundt et al., Heterocyclic Analogues of N-(4-(4-(2,3-Dichlorophenyl)piperazin-1-yl)butyl)arylcarboxamides with Functionalized Linking Chains as Novel Dopamine D3 Receptor Ligands Potential Substance Abuse Therapeutic Agents *J. Med. Chem.* 2007, 50, 4135-4146.
8. D. J. Wustrow et al., Studies of the active conformation of a novel series of benzamide dopamine $D_2$ agonists. *J. Med. Chem.* 1994, 37, 4251-4257.
9. D. Wustrow et al., Aminopyrimidines with high affinity for both serotonin and dopamine receptors. *J. Med. Chem.* 1998, 41, 760-771.
10. T. B. Belliotti et al., Novel cyclohexyl amides as potent and selective $D_3$ dopamine receptor ligands. *Bioorg. Med. Chem. Letts.* 1997, 7, 2403-2408.
11. M. J. Robarge et al., Design and synthesis of [(2,3-dichlorophenyl)piperazin-1-yl]alkylfluorenylcarboxamides as novel ligands selective for the dopamine $D_3$ receptor subtype. *J. Med. Chem.* 2001, 44, 3175-3186.
12. L. Bettinetti et al., Interactive SAR studies: rational discovery of super-potent and highly selective $D_3$ receptor antagonists and partial agonists. *J. Med. Chem.* 2002, 45, 4594-4597.
13. A. Hackling et al., N-(ö-(4-(2-Methoxyphenyl)piperazin-1-yl)alkyl) carboxamides as dopamine $D_2$ and $D_3$ receptor ligands. *J. Med. Chem.* 2003, 46, 3883-3899.

14. M. Leopoldo et al., Structure-affinity relationship study on N-[4-(4-arylpiperazin-1-yl)butyl]arylcarboxamides as potent and selective dopamine $D_3$ receptor ligands. *J. Med. Chem.* 2002, 45, 5727-5735.
15. G. Campiani et al., Synthesis and pharmacological evaluation of potent and highly selective $D_3$ receptor ligands: inhibition of cocaine-seeking behavior and the role of dopamine $D_3/D_2$ receptors. *J. Med. Chem.* 2003, 46, 3822-3839.
16. G. Campiani et al., Pyrrolo[1,3]benzothiazepine-based serotonin and dopamine receptor antagonists: molecular modeling, further structure activity relationship studies, and identification of novel atypical antipsychotic agents. *J. Med. Chem.* 2004, 47, 143-157.
17. P. Grundt et al., Novel Heterocyclic Trans Olefin Analogues of N-{4-[4-(2,3-Dichloro phenyl)piperazin-1-yl] butyl}arylcarboxamides as Selective Probes with High Affinity for the Dopamine $D_3$ Receptor. *J. Med. Chem.* 2005, 48, 839-848.
18. J. Varady et al., Molecular modeling of the three-dimensional structure of dopamine 3 subtype receptor. Discovery of novel and potent $D_3$ ligands through a hybrid pharmacophore- and structure-based database searching approach. *J. Med. Chem.* 2003, 46, 4377-4392.
19. S. R. Haadsma-Svensson et al. Dopamine $D_3$ receptor antagonists. 1. Synthesis and structure-activity relationship of 5,6-dimethoxyl-N-alkyl- and N-alkylaryl-substituted 2-aminoindans. *J. Med. Chem.* 2001, 44, 4716-4732.
20. M. Ji et al., Design, synthesis and structure-activity relationship studies of hexahydropyrazinoquinolines as a novel class of potent and selective dopamine receptor 3 (D3) ligands. *Bioorg. Med. Chem. Lett.,* 2005, 15, 1701-1705.
21. K. Ding et al., Enantiomerically Pure Hexahydropyrazinoquinolines as Potent and Selective Dopamine 3 Subtype Receptor Ligands, *J. Med. Chem.* 2005, 48, 3171-3181.
22. J. Chen et al., Design of Novel Hexahydropyrazinoquinolines as Potent and Selective Dopamine D3 Receptor Ligands with Improved Solubility. *Bioorg. Med. Chem. Lett.* 2006, 16, 443-446.
23. M. J. Millan et al., Differential actions of antiparkinson agents at multiple classes of monoaminergic receptor. I. A multivariate analysis of the binding profiles of 14 drugs at 21 native and cloned human receptor subtypes. *J. Pharmacol. Exp. Ther.* 2002, 303, 791-804.
24. G. T. Collins et al., Dopamine agonist-induced yawning in rats: a dopamine D3 receptor-mediated behavior. *J. Pharmacol. Exp. Ther.* 2005, 314, 310-9.
25. G. T. Collins et al., Yawning and hypothermia in rats: effects of dopamine D3 and D2 agonists and antagonists. *Psychopharmacology (Berl).* 2007, 193, 159-70.
26. V. Cherezov et al., High resolution crystal structure of an engineered human beta2-adrenergic G protein-coupled receptor. *Science,* 2007, 318, 1258-1265.
27. S. G. Rasmussen et al., Crystal structure of the human beta2 adrenergic G-protein-coupled receptor. *Nature,* 2007, 450, 383-7.
28. T. Kenakin, The classification of seven transmembrane receptors in recombinant expression systems. *Pharmacol. Rev.* 1996, 48, 413-463.
29. B. Levant et al., Characterization of [3H]quinpirole binding to D2-like dopamine receptors in rat brain. *J. Pharmacol. Exp. Ther.* 1992, 262, 929-935.
30. G. N. Bancroft et al., Binding of [3H]PD 128907, a putatively selective ligand for the D3 dopamine receptor, in rat brain: a receptor binding and quantitative autoradiographic study. *Neuropsychopharmacology* 1998, 18, 305-316.
31. B. Levant, Characterization of dopamine receptors. In Current Protocols in Pharmacology; Enna, S. J.; Williams, M.; Ferkany, J. W.; Kenakin, T.; Porsolt, R. D.; Sullivan, J. P., Eds.; John Wiley & Sons: New York, 1998, pp 1.6.1-1.6.16.
32. D. Boulay et al., Dopamine D2 receptor knock-out mice are insensitive to the hypolocomotor and hypothermic effects of dopamine D2/D3 receptor agonists. *Neuropharmacology.* 1999, 38, 1389-96.
33. F. Chaperon et al., Evidence for regulation of body temperature in rats by dopamine D2 receptor and possible influence of D1 but not D3 and D4 receptors. *Neuropharmacology.* 2003, 44, 1047-53.
34. M. Fujikawa et al., Partial agonistic effects of OPC-14597, a potential antipsychotic agent, on yawning behavior in rats. *Pharmacol. Biochem. Behav.* 1996, 53, 903-909.
35. J. M. Baldwin et al., An Alpha-carbon template for the transmembrane helices in the rhodopsin family of G-protein-coupled receptors. *J. Mol. Biol.* 1997, 272, 144-164.
36. A. Sali et al., Comparative protein modelling by satisfaction of spatial restraints. *J. Mol. Biol.* 1993, 234, 779-815.
37. H. Heller et al., Molecular dynamics simulation of a bilayer of 200 lipids in the gel and in the liquid-crystal phases. *J. Phys. Chem.* 1993, 97, 8343-8360.
38. H. J. C. Berendsen, The Netherlands, http://www.gromacs.org, 2002.
39. G. Jones et al. Development and validation of a genetic algorithm for flexible docking. *J. Mol. Biol.* 1997, 267, 727-748.
40. M. L. Verdonk et al., Improved protein-ligand docking using GOLD. *Proteins,* 2003, 52, 609-623.

APPENDIX A

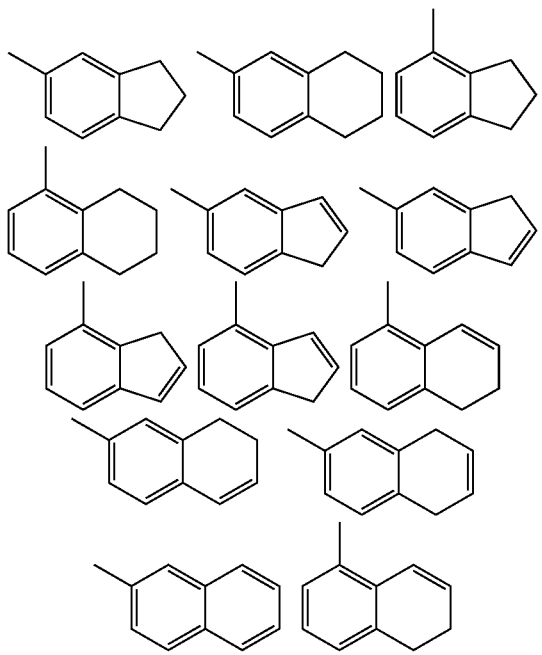

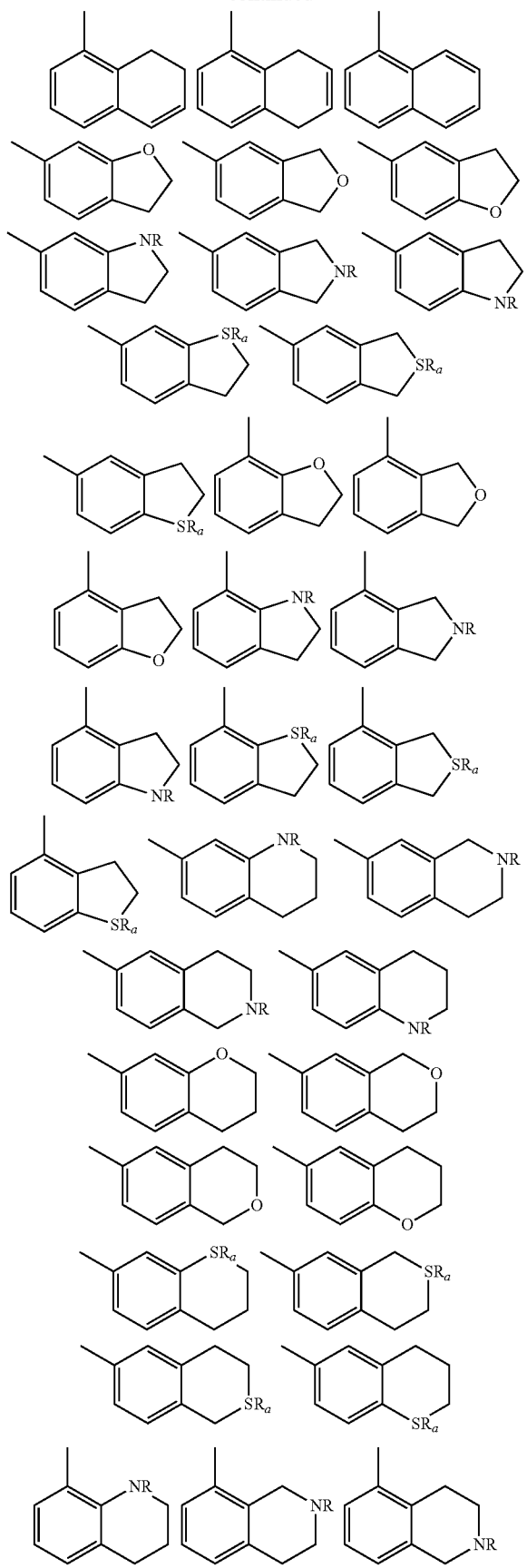
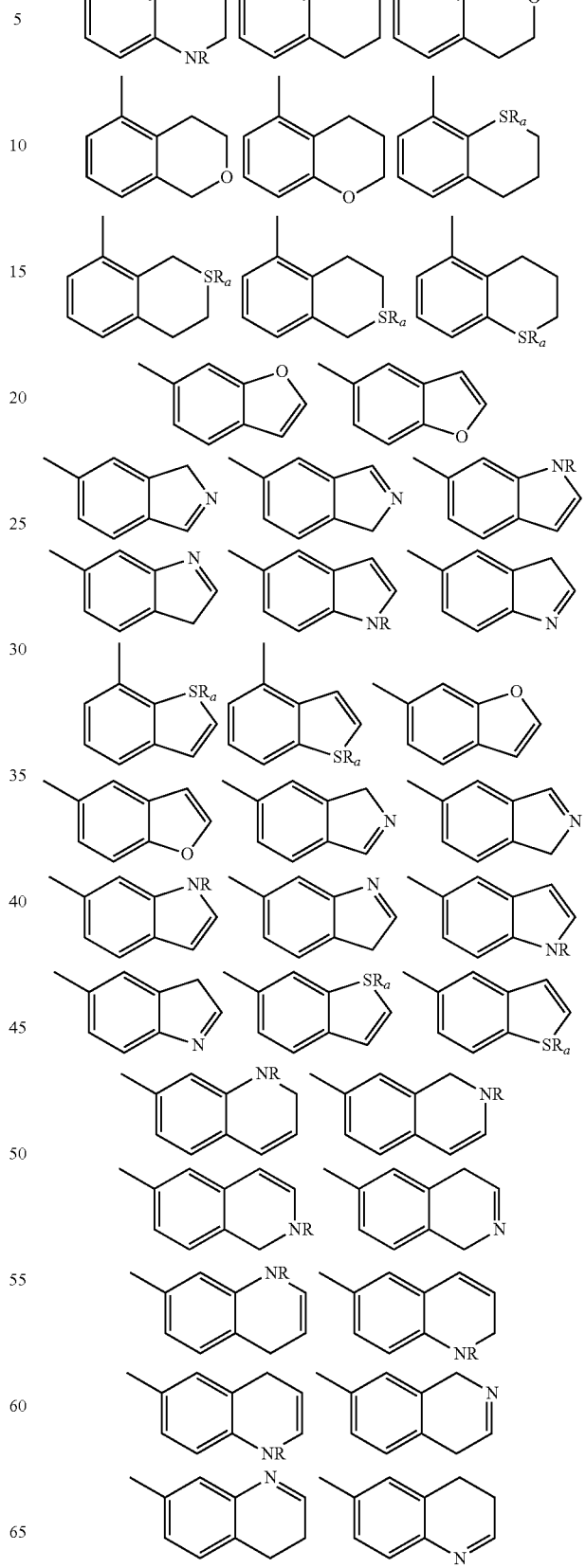

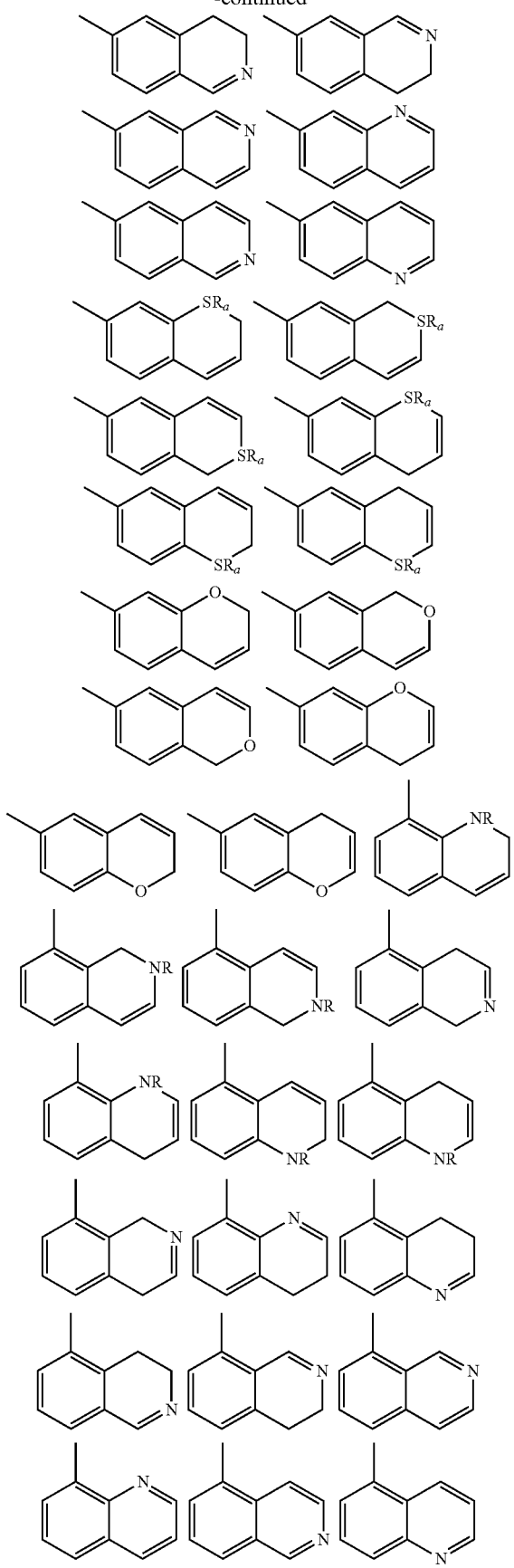
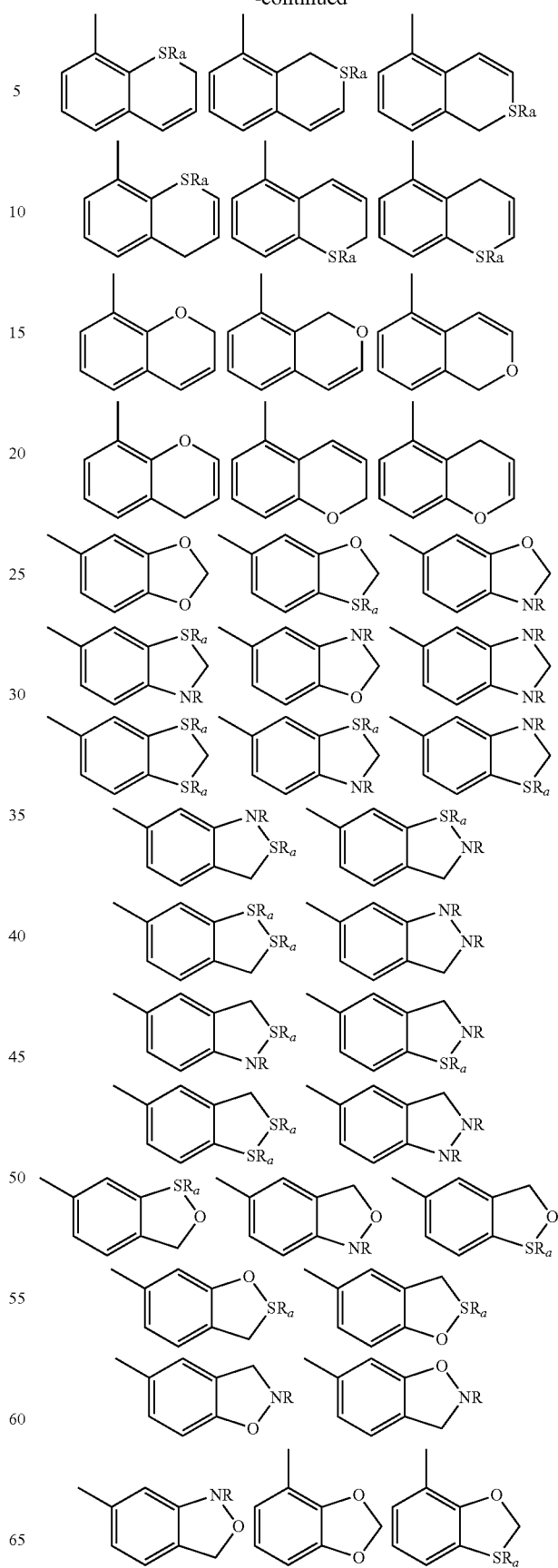

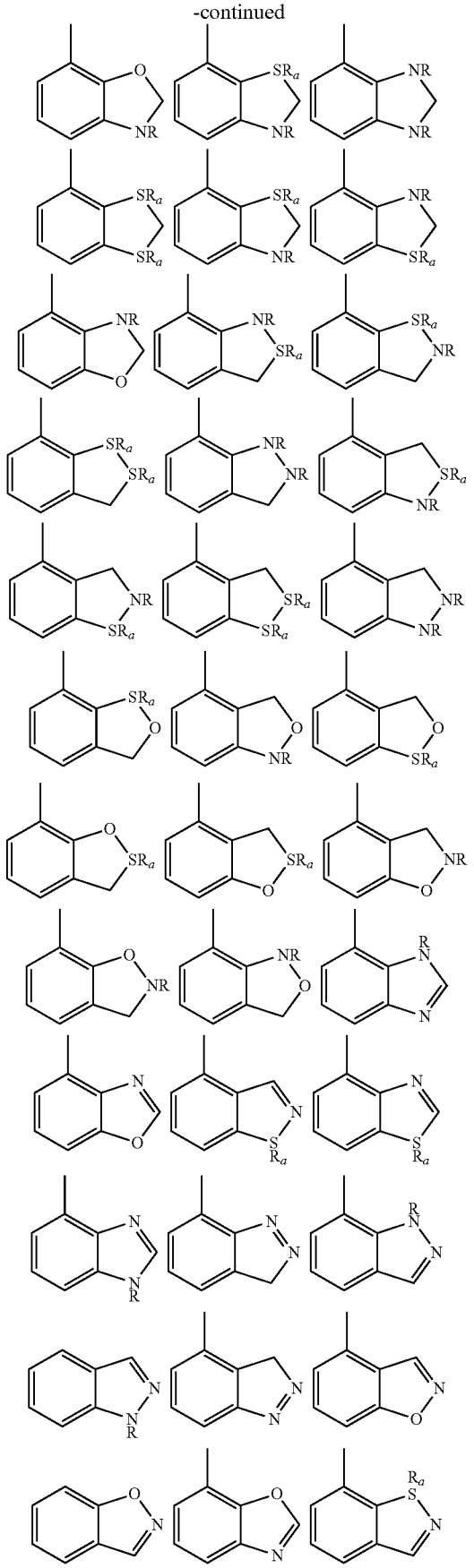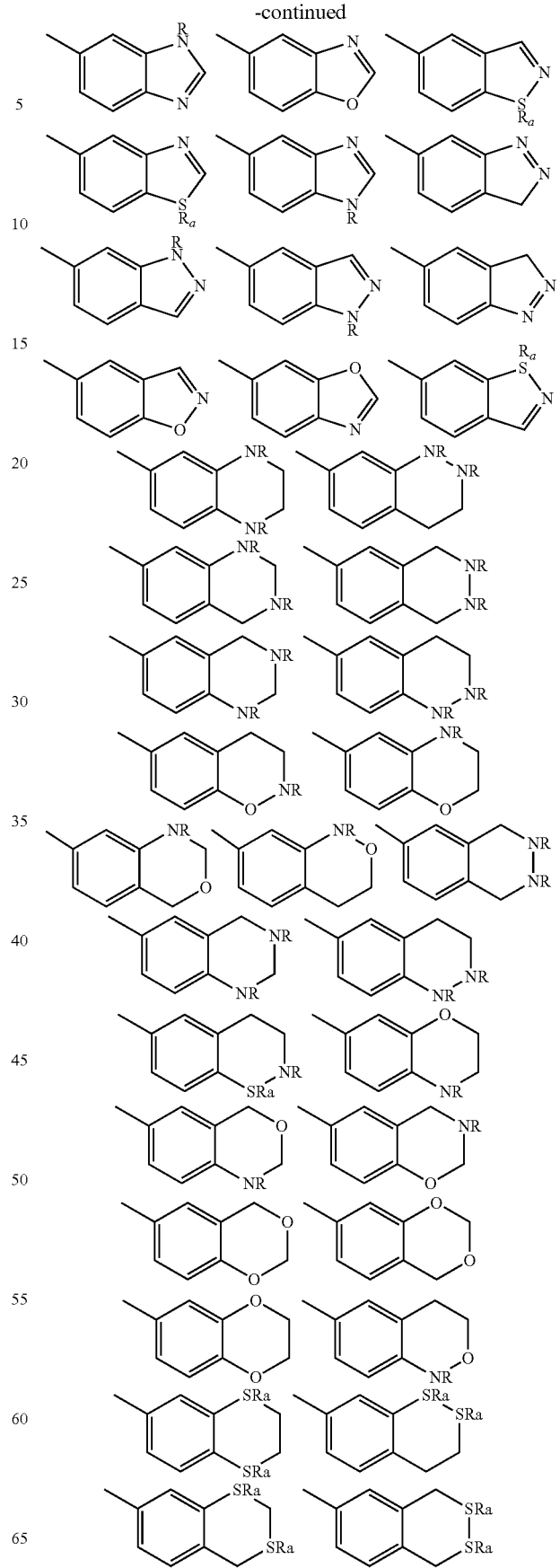

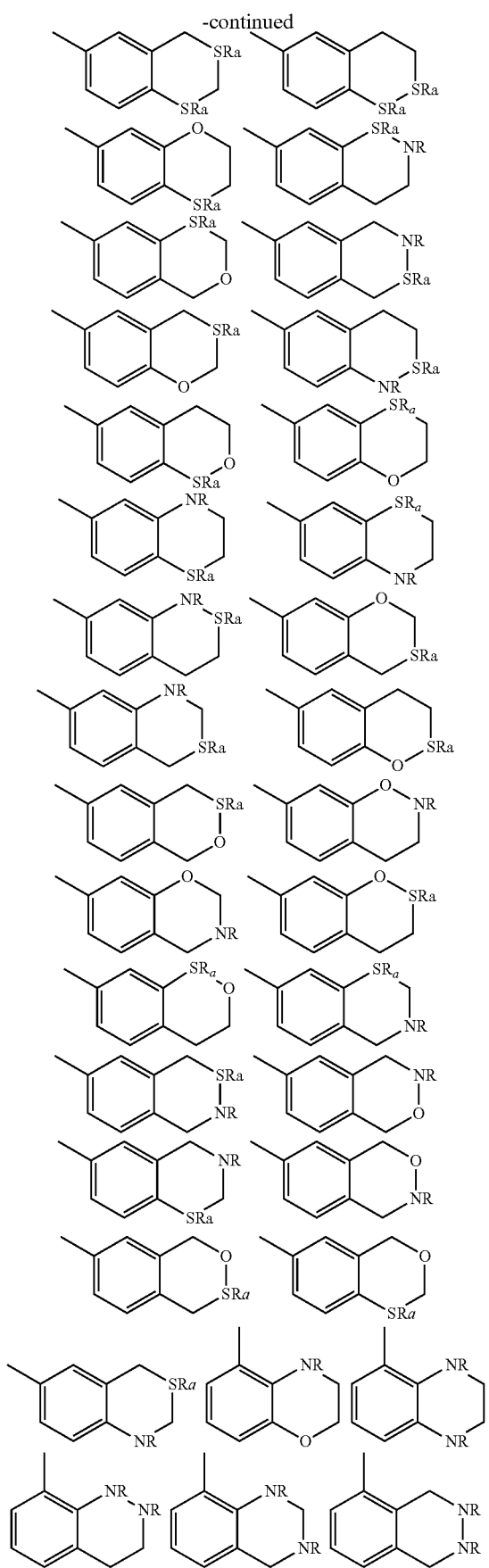
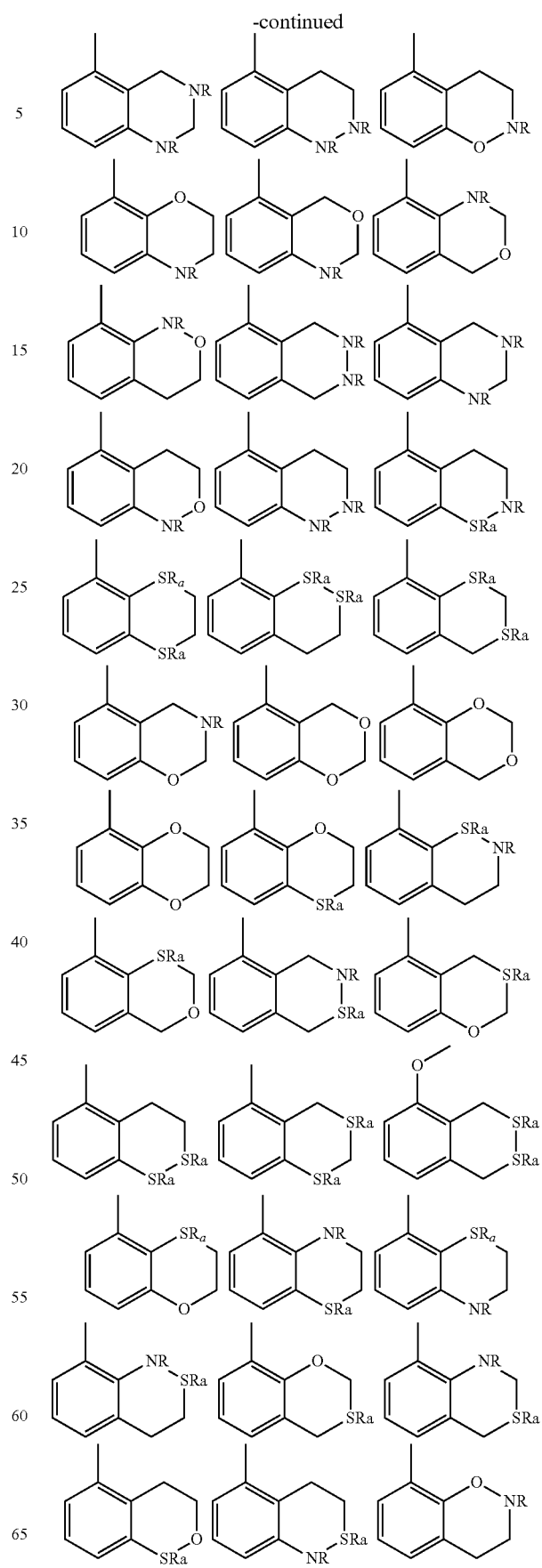

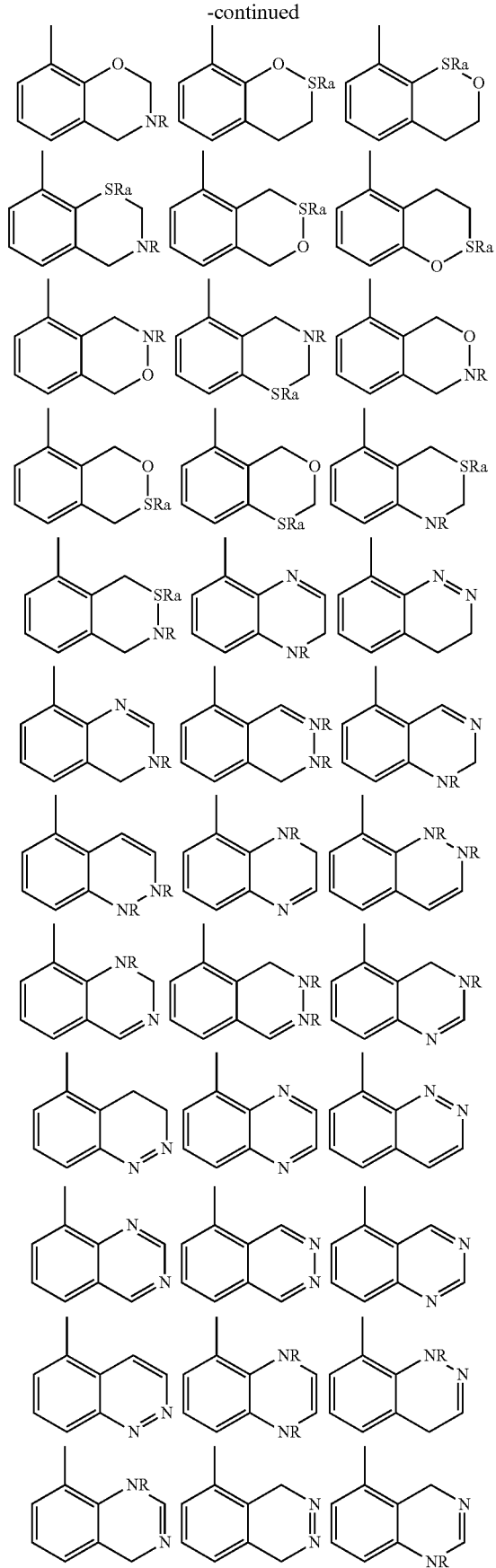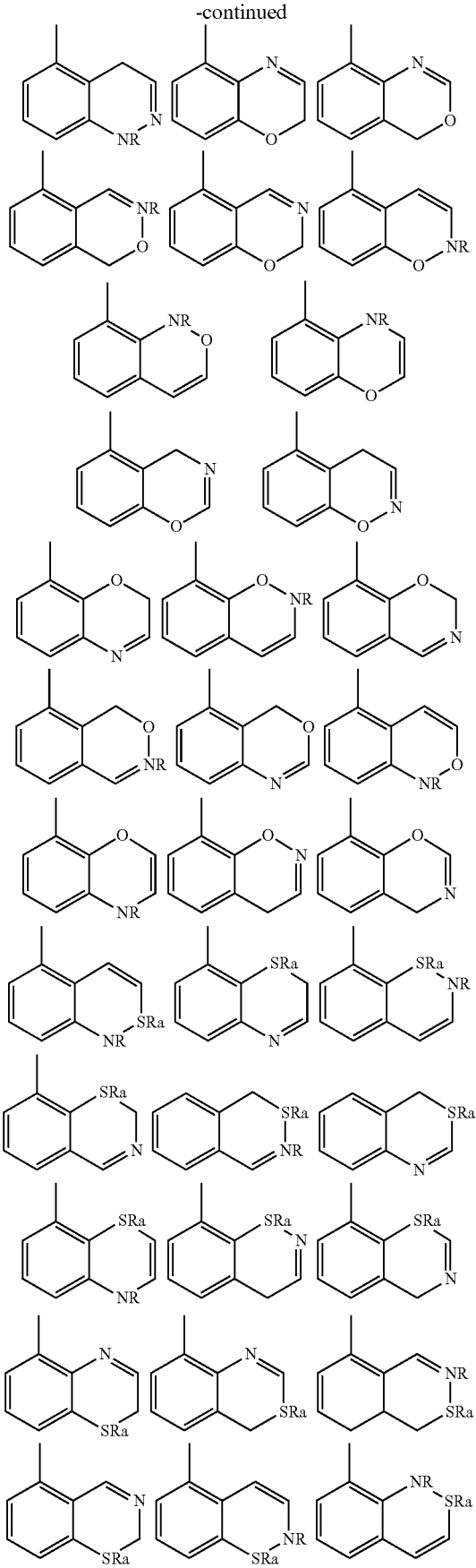

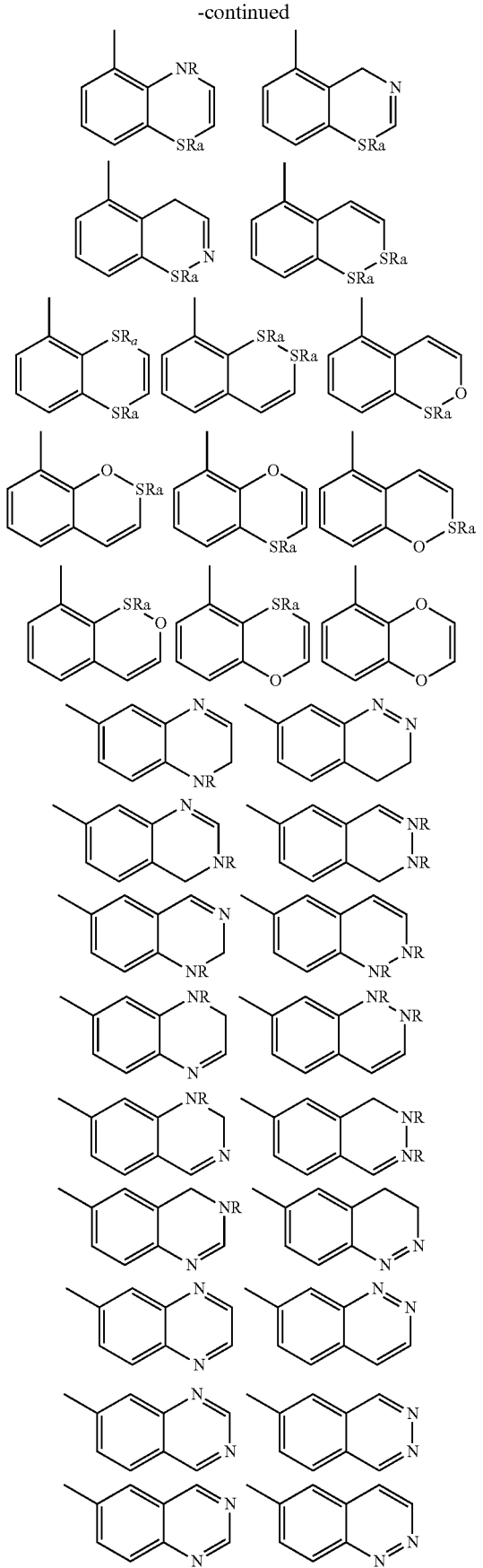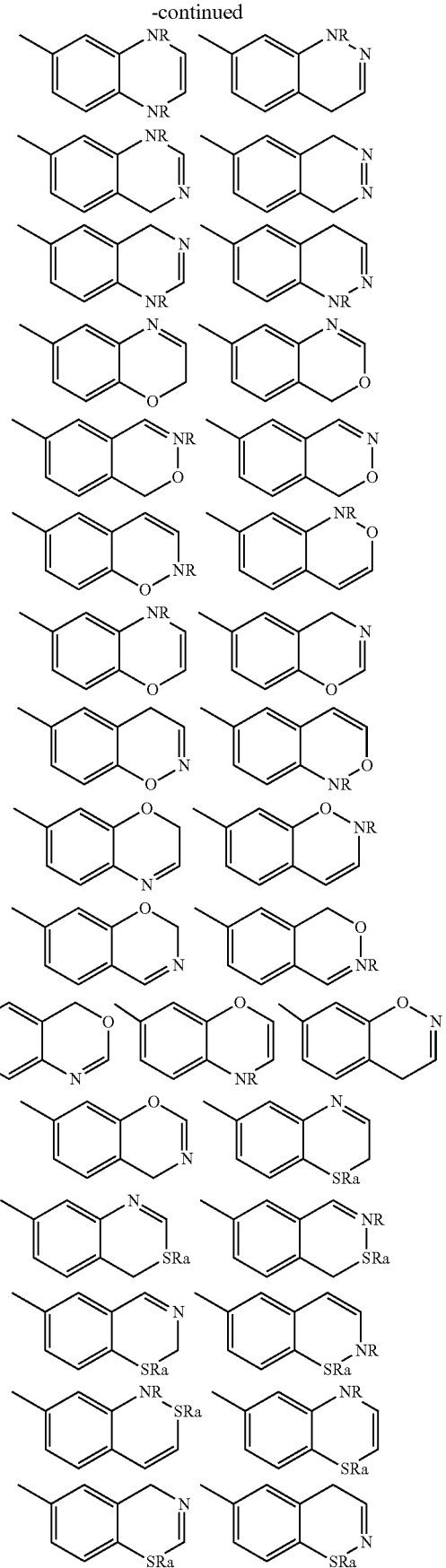

-continued

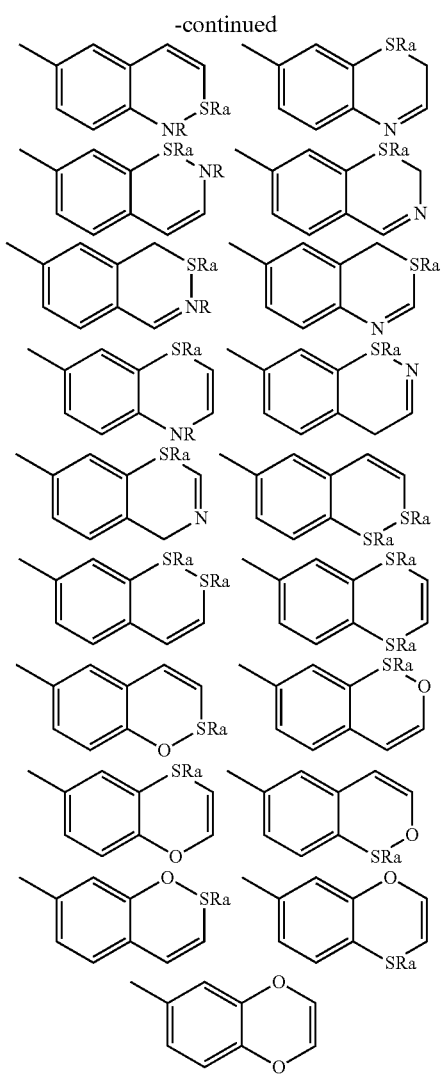

wherein R and $R_a$, independently, are selected from the group consisting of hydrogen, $C_{1-6}$alkyl, $C_{3-8}$cycloalkyl, heterocycloalkyl, aryl, and heteroaryl.

What is claimed:

1. A compound having a structural formula

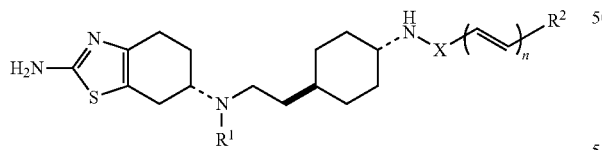

wherein X is C=O or $SO_2$, $R^1$ is $C_{1-6}$ alkyl, $R^2$ is unsubstituted or substituted and is aryl, heteroaryl, —$(CH_2)_{1-3}$aryl, or —$(CH_2)_{1-3}$heteroaryl, and n is 0 or 1, or a pharmaceutically acceptable salt thereof.

2. The compound of claim 1 wherein X is C=O.
3. The compound of claim 1 wherein X is $SO_2$.
4. The compound of claim 1 wherein $R^1$ is $C_{1-4}$ alkyl.
5. The compound of claim 1 wherein $R^1$ is n-propyl.
6. The compound of claim 1 wherein $R^2$ is aryl.
7. The compound of claim 6 wherein $R^2$ is phenyl or naphthyl.

8. The compound of claim 1 wherein $R^2$ is heteroaryl.

9. The compound of claim 8 wherein $R^2$ is selected from the group consisting of pyridyl, pyrrolyl, indolyl, furanyl, benzofuranyl, thiophenyl, quinolinyl, isoquinolinyl, and pyrimidinyl.

10. The compound of claim 1 wherein $R^2$ is substituted with a group selected from the group consisting of halo, $OC_{1-3}$ alkyl, phenyl, OH, pyridinyl, pyrimidinyl, pyrazinyl, imidazolyl, pyrazolinyl, triazolyl, pyrazolyl, $C_{1-3}$alkylphenyl, $C_{1-3}$alkylpyrimidinyl, $C_{1-3}$alkylpyridinyl, $C_{1-3}$alkylOphenyl, HOphenyl, and halophenyl.

11. The compound of claim 10 wherein halo is chloro or fluoro and $C_{1-3}$alkyl is methyl.

12. The compound of claim 1 wherein $R^2$ is selected from the group consisting of thienyl, furyl, oxazolyl, quinolyl, thiophenyl, isoquinolyl, indolyl, triazinyl, triazolyl, isothiazolyl, isoxazolyl, imidazolyl, benzothiazolyl, pyrimidinyl, thiazolyl, thiadiazolyl, pyridinyl, pyridazinyl, pyrazolyl, pyrazinyl, quinolyl, tetrazolyl, oxazolyl, pyrrolyl, benzimidazolyl, benzofuranyl, cinnolinyl, indazolyl, indolizinyl, phthalazinyl, triazinyl, isoindolyl, purinyl, oxadiazolyl, furazanyl, benzofurazanyl, benzothiophenyl, benzotriazolyl, benzothiazolyl, benzisothiazolyl, benzoxazolyl, benzisoxazolyl, benzimidazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrrolopyrimidinyl, and azaindolyl.

13. The compound of claim 1 wherein

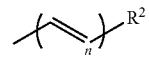

is selected from the group consisting of

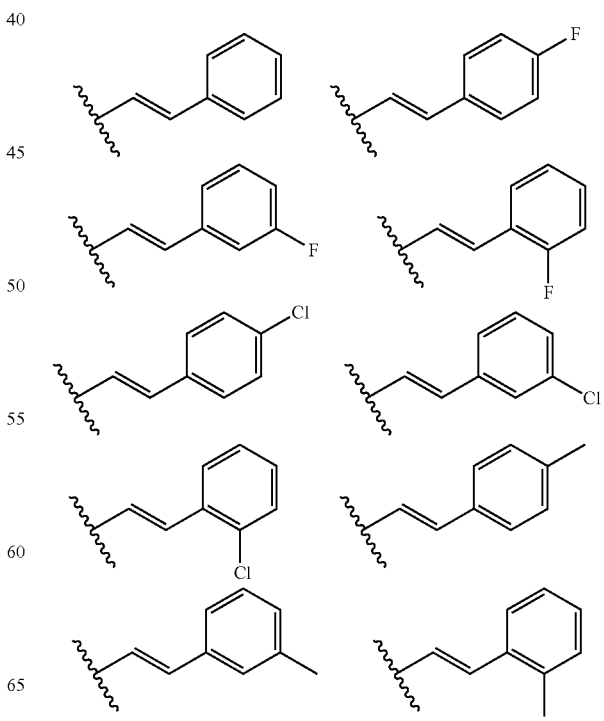

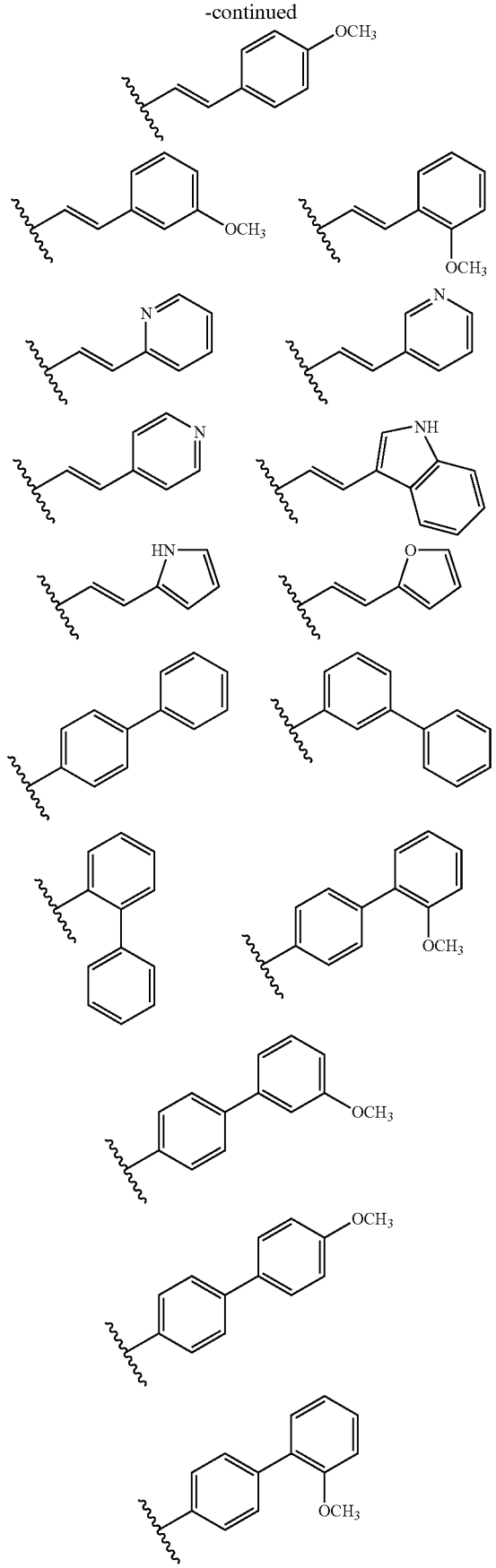
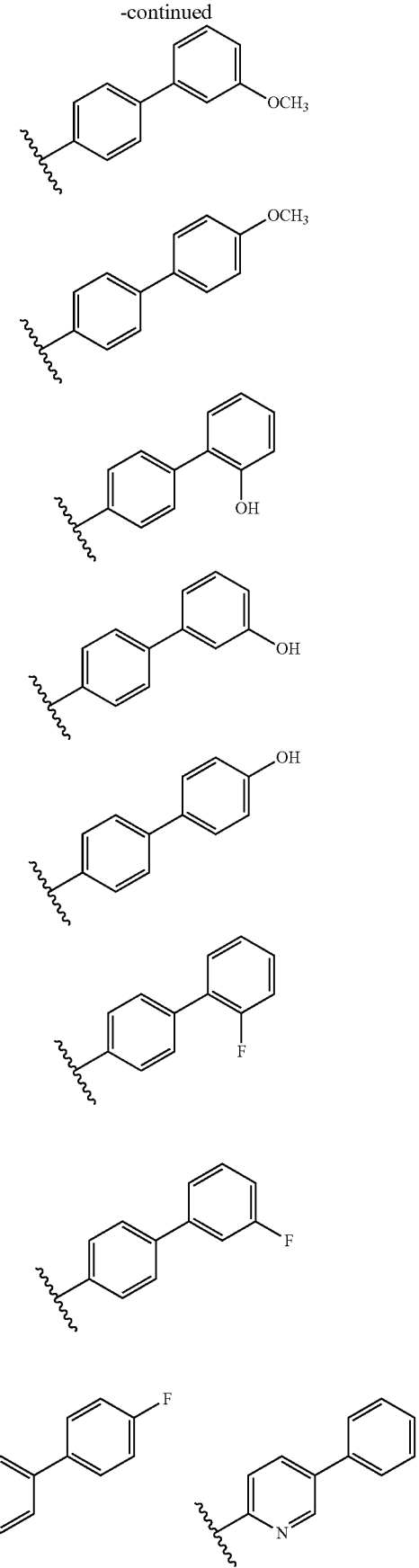

-continued
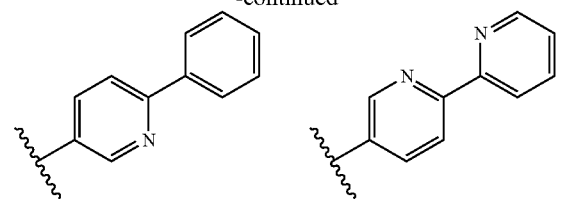
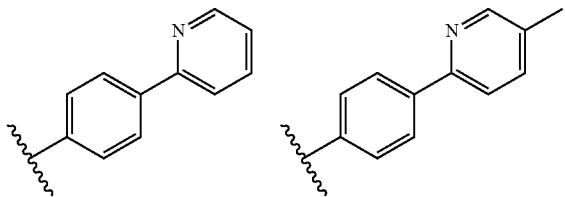
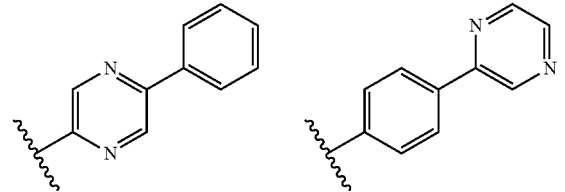
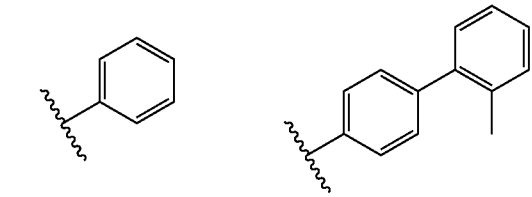
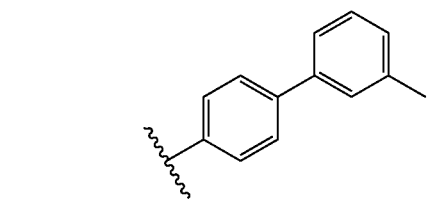
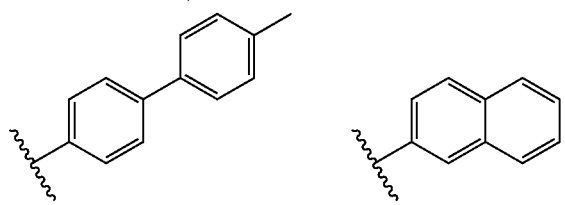
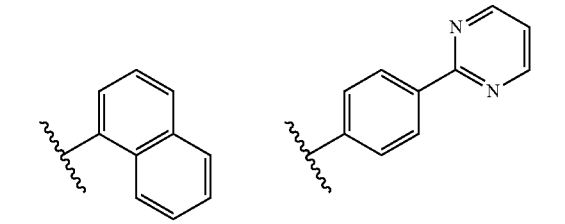
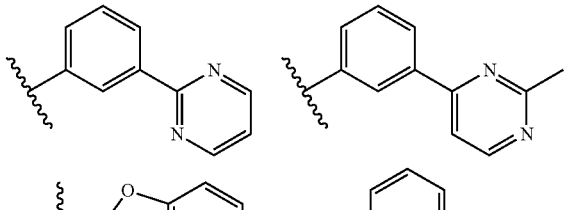
-continued
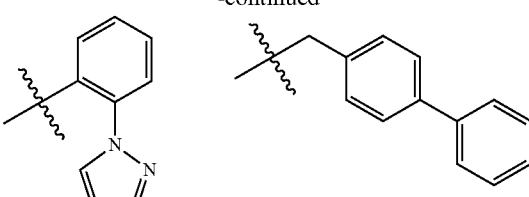
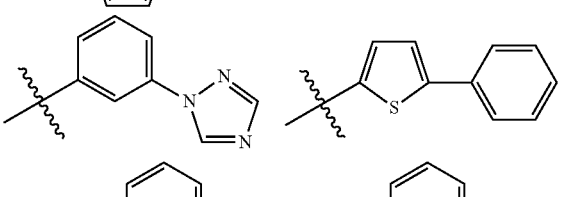
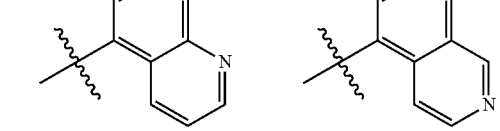
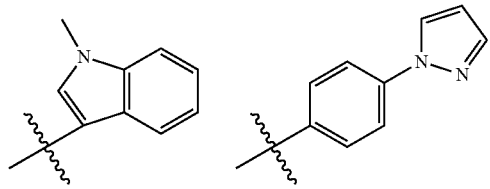
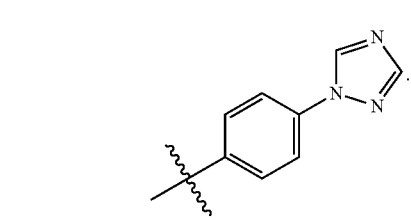
and
14. The compound of claim 1 having a structural formula
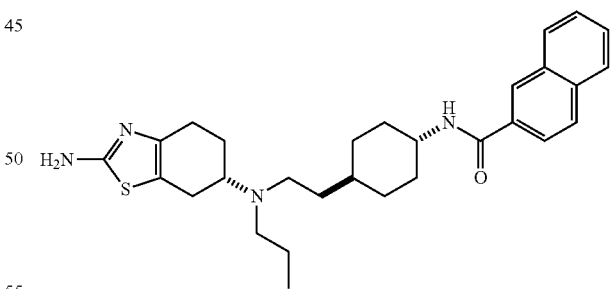
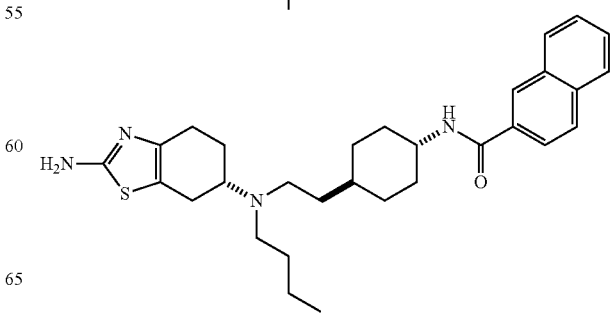

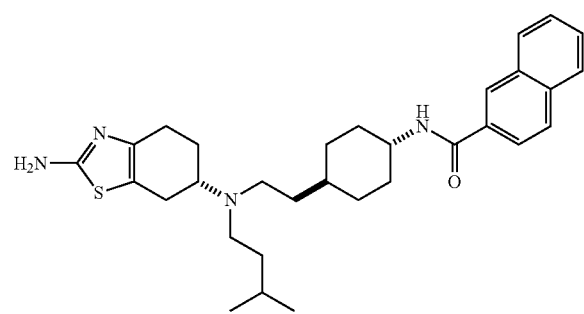
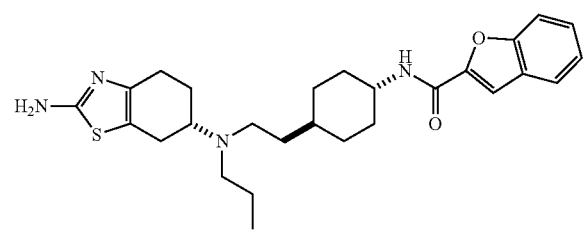
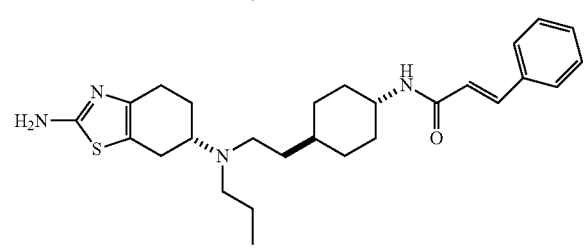
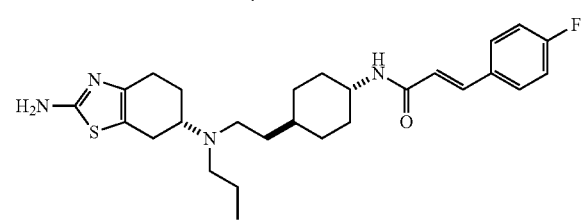
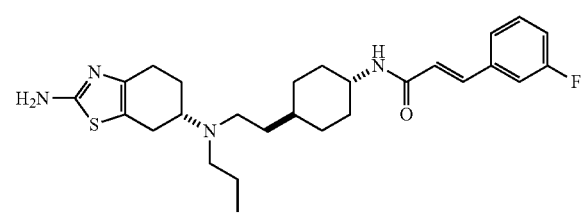
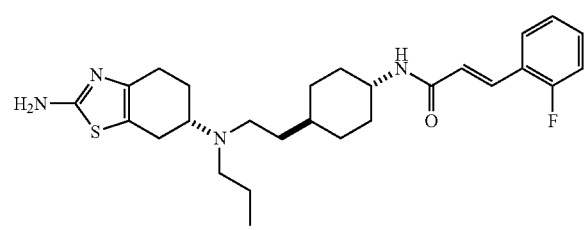
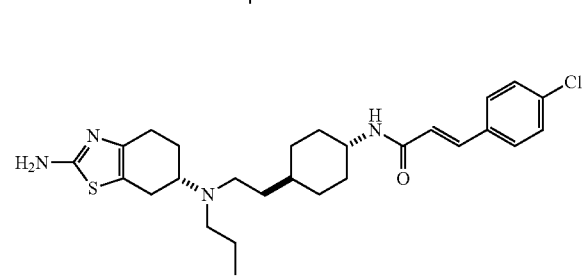
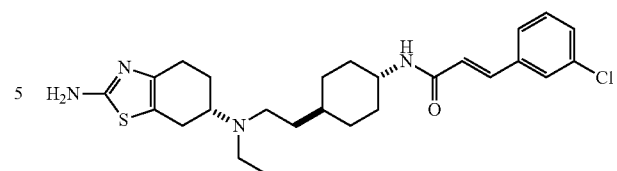
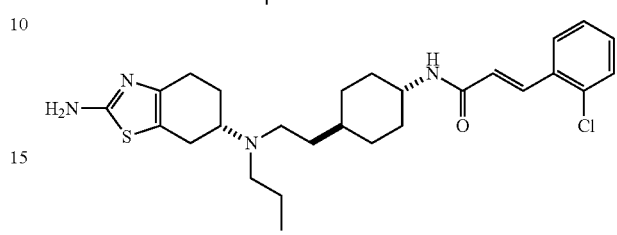
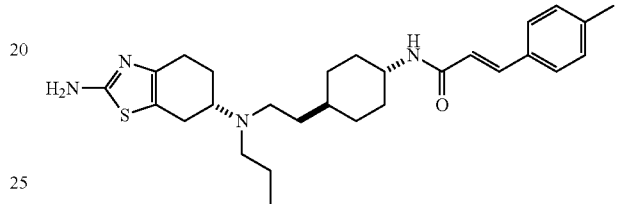
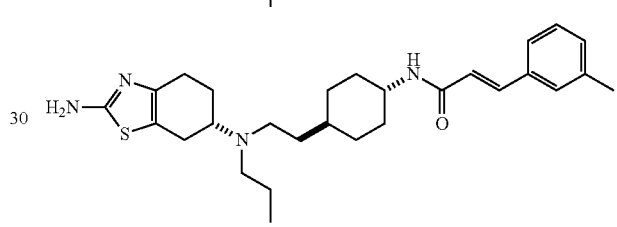
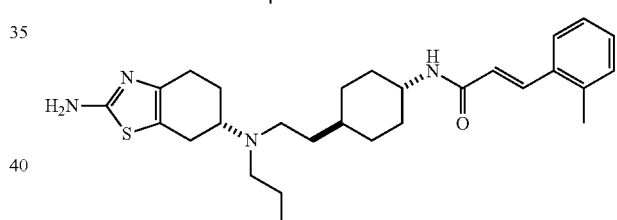
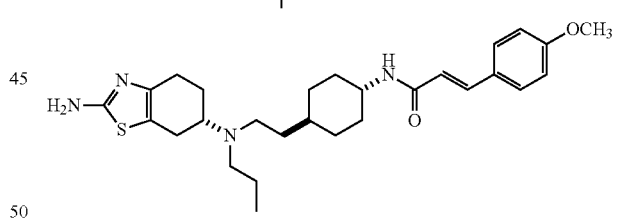
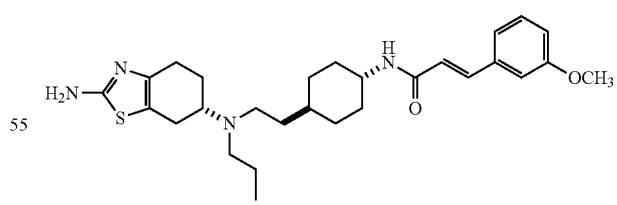
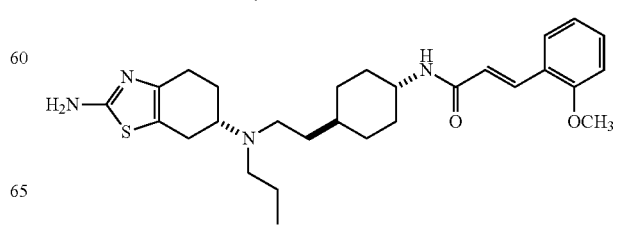

77
-continued
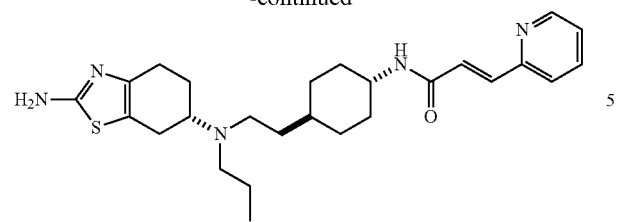
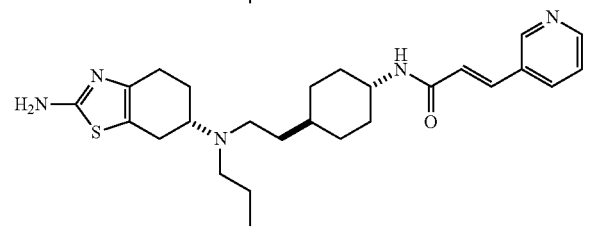
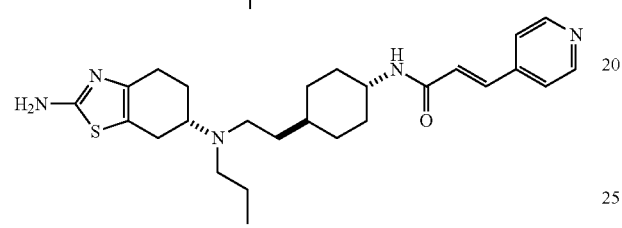
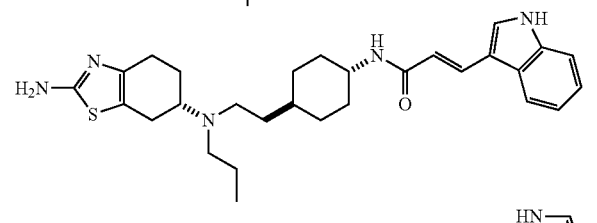
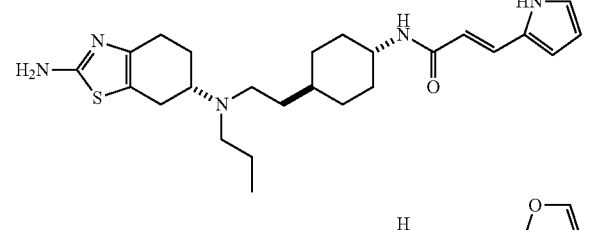
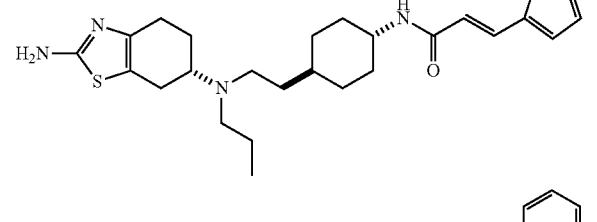
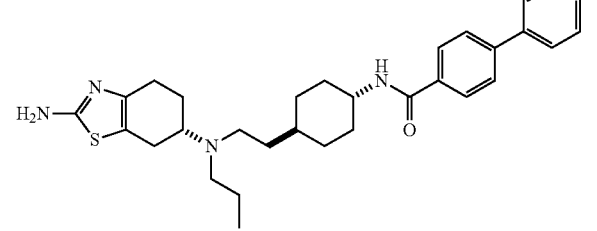
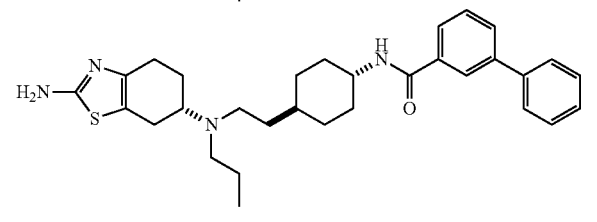
78
-continued
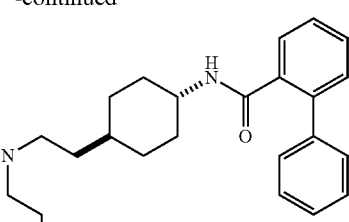
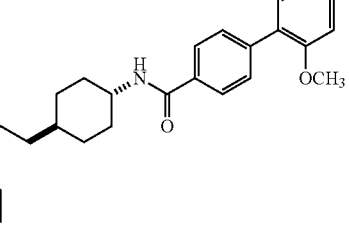
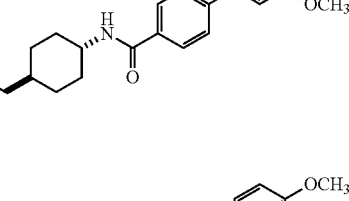
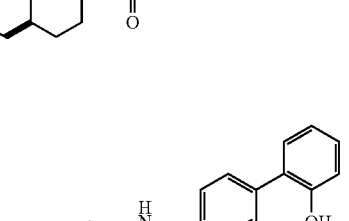
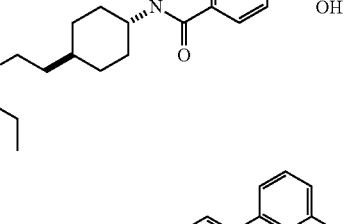
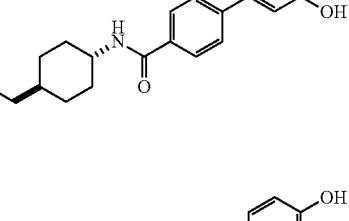
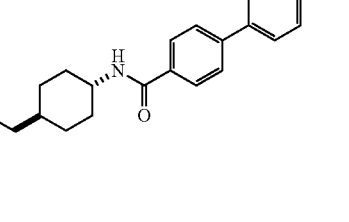

-continued
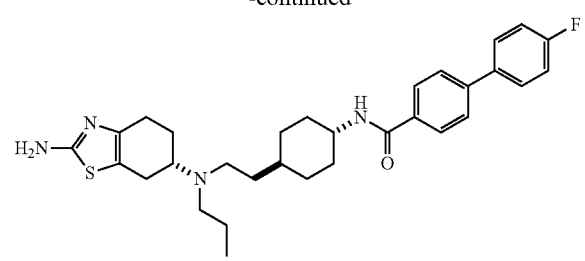
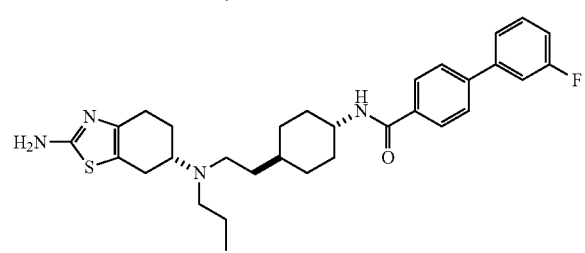
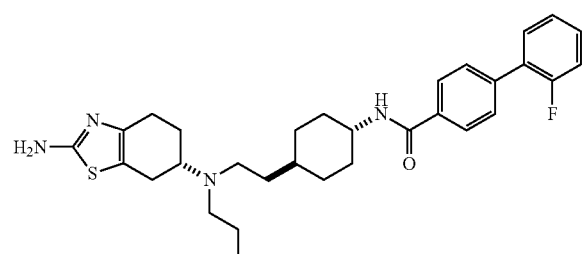
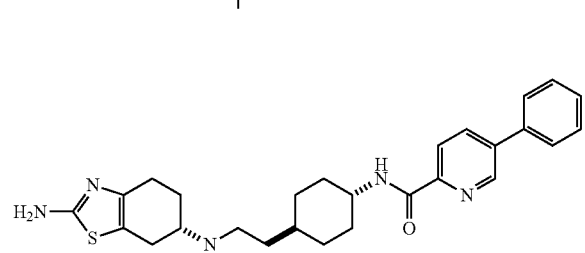
-continued
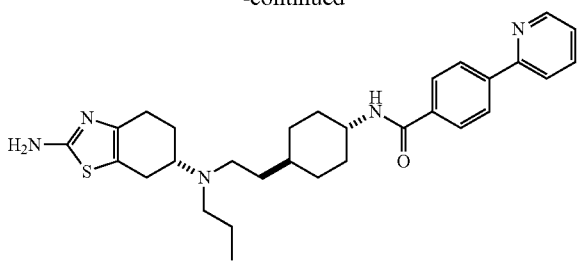
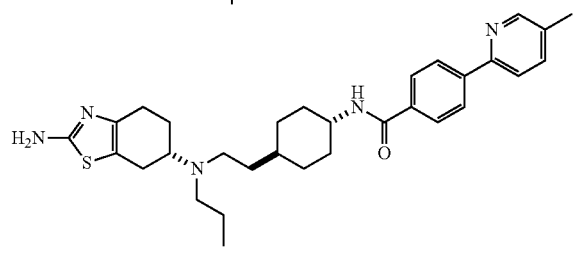
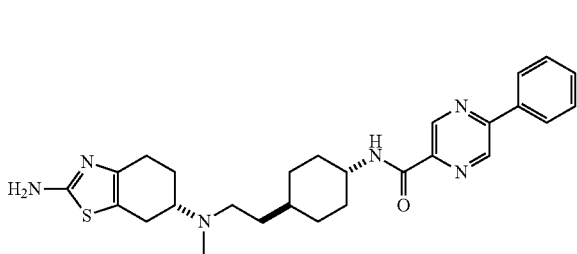
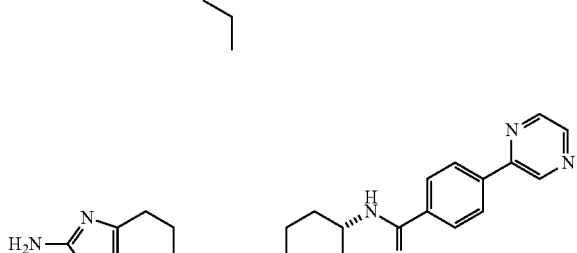

81
-continued
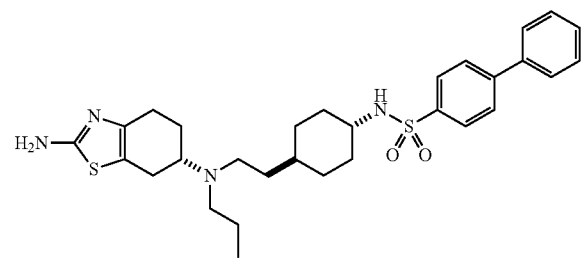
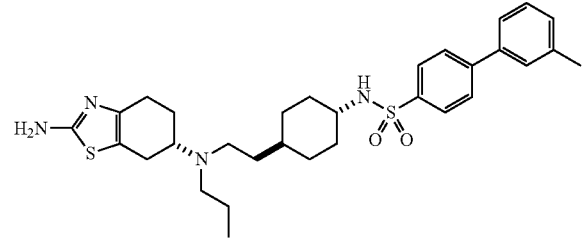
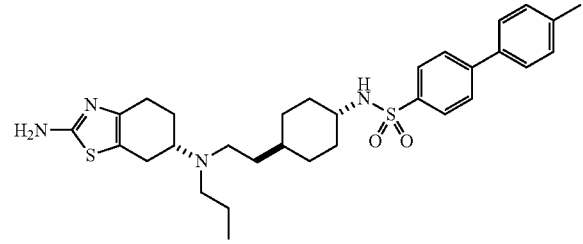
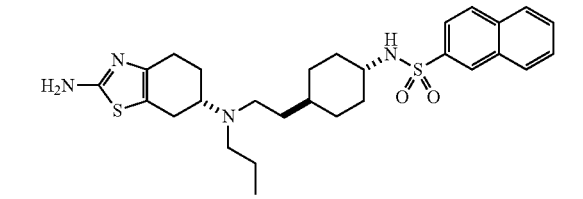
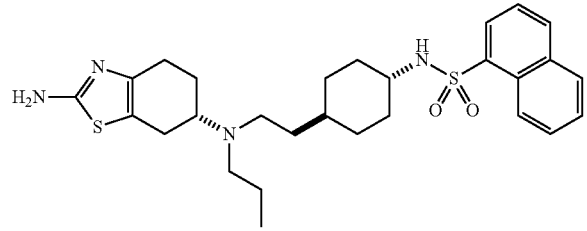
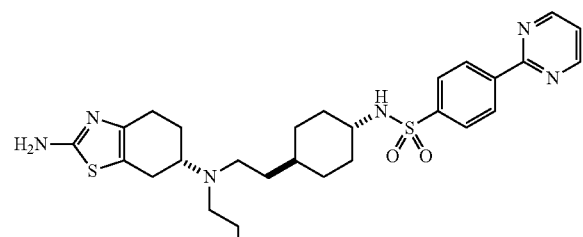
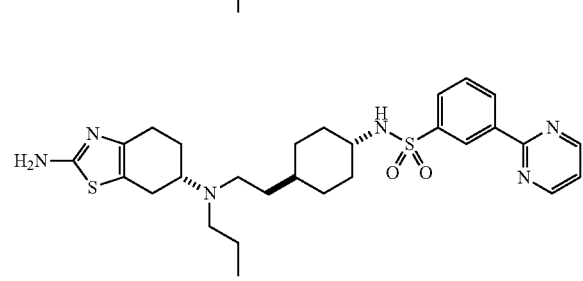
82
-continued
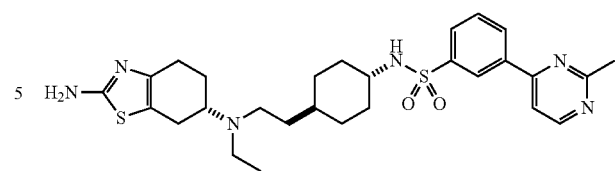
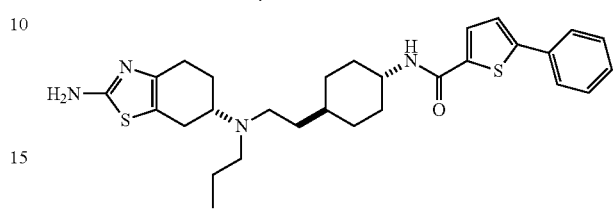
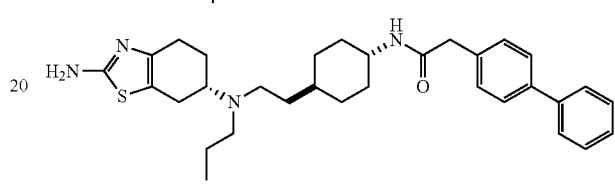
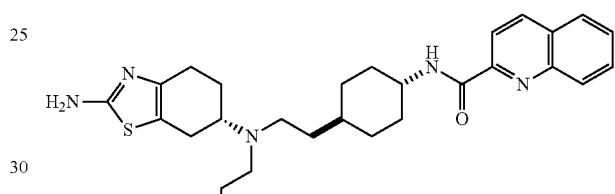
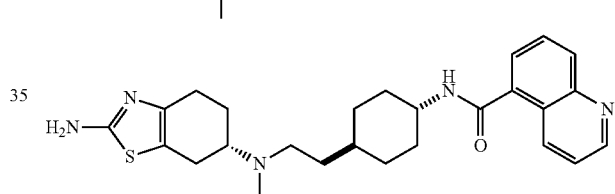
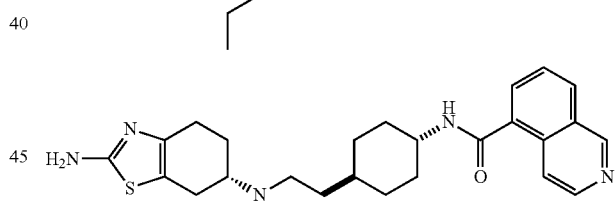
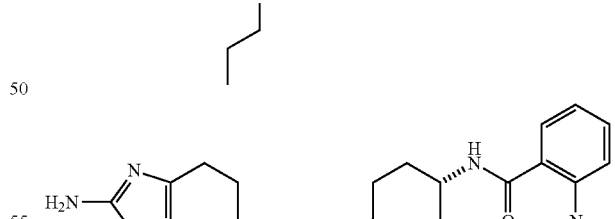
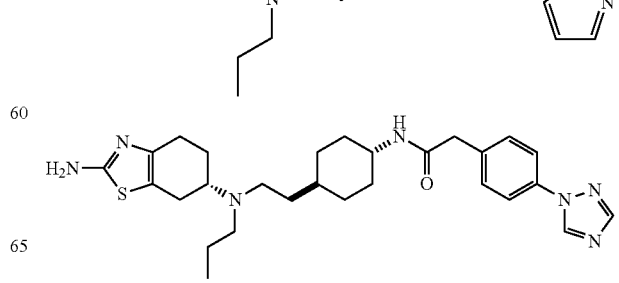

15. A method of treating a disease or condition wherein modulation of dopamine $D_3$ receptors provides a benefit comprising administering a compound of claim 1 to an individual in need thereof, wherein the disease or condition is selected from the group consisting of symptoms of Parkinson's disease, restless leg syndrome, schizophrenia, depression, symptoms of Tourette's syndrome, and chronic pain.

16. The method of claim 15 further comprising administering a therapeutically effective amount of a second therapeutic agent useful in the treatment of the disease or condition.

17. The method of claim 15 wherein the compound of claim 1 and the second therapeutic agent are administered simultaneously.

18. The method of claim 15 wherein the compound of claim 1 and the second therapeutic agent are administered from a single composition.

19. The method of claim 15 wherein the compound of claim 1 and the second therapeutic agent are administered from separate compositions.

20. The method of claim 19 wherein the compound of claim 1 is administered prior to the second therapeutic agent.

21. The method of claim 19 wherein the compound of claim 1 is administered after the second therapeutic agent.

22. The method of claim 16 wherein the second therapeutic agent is selected from the group consisting of an antipsychotic agent, an antidepressant agent, a monoamine oxidase inhibitor, a 5-HT reuptake inhibitor, a serotonin-1 B antagonist, a serotonin-2A antagonist, a histamine-3 antagonist or agonist, and an antiparkinsonian agent.

23. The method of claim 16 wherein the second therapeutic agent is selected from the group consisting of clozapine, olanzapine, quetiapine, risperidone, ziprasidone, haloperidol, aripiprazole, a tricyclic antidepressant, amitriptyline, dothiepin, doxepin, trimipramine, butriptyline, clomipramine, desipramine, imipramine, iprindole, lofepramine, nortriptyline, protriptyline, isocarboxazid, phenelzine, tranylcyclopramine, fluvoxamine, sertraline, fluoxetine, paroxetine, elzasonan, eplivanserin, MDL-100907, cipralisant, ABT239, TISQ, GSK-189254A, a dopaminergic antiparkinsonian agent, and levodopa, alone or in combination with a peripheral decarboxylase inhibitor, benserazide, or carbidopa, or with a dopamine agonist, bromocriptine, lysuride, or pergolide, and mixtures thereof.

24. A kit comprising:
    (a) a packaged composition comprising a compound of claim 1;
    (b) optionally, a packaged composition comprising a second therapeutic agent useful in a treatment of a disease or condition wherein modulation of $D_3$ receptors provide a benefit;
    (c) an insert providing instructions for a simultaneous or sequential administration of (a), or (a) and (b), to treat a disease or condition wherein modulation of $D_3$ receptors provide a benefit in a human;
    (d) a container for (a), (b), and (c),
    wherein the disease or condition is selected from the group consisting of symptoms of Parkinson's disease, restless leg syndrome, schizophrenia, depression, symptoms of Tourette's syndrome, and chronic pain.

25. A composition comprising (a) a compound of claim 1, (b) a second therapeutic agent useful in the treatment of a disease or condition wherein modulation of $D_3$ receptors provide a benefit, and (c) an optional excipient and/or pharmaceutically acceptable carrier,
    wherein the disease or condition is selected from the group consisting of symptoms of Parkinson's disease, restless leg syndrome, schizophrenia, depression, symptoms of Tourette's syndrome, and chronic pain.

26. The compound of claim 1 wherein $R^2$ is selected from the group consisting of

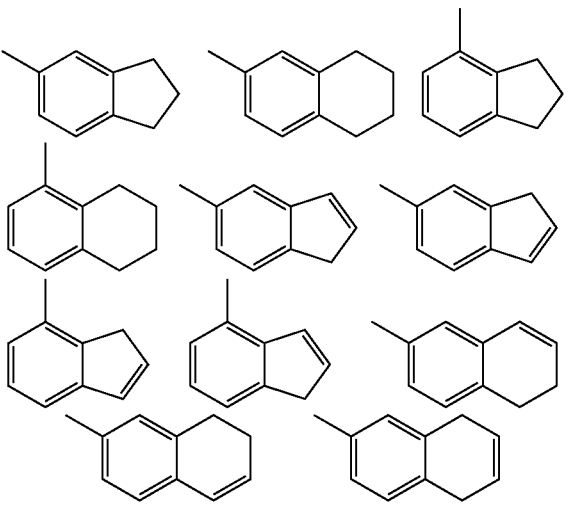

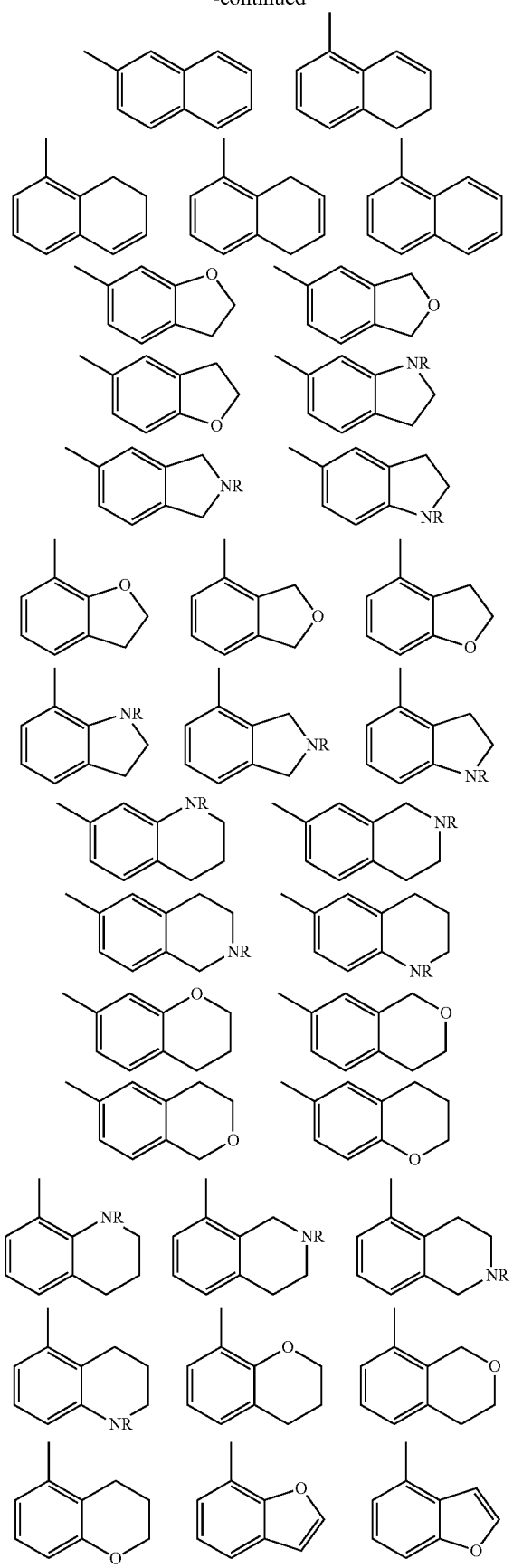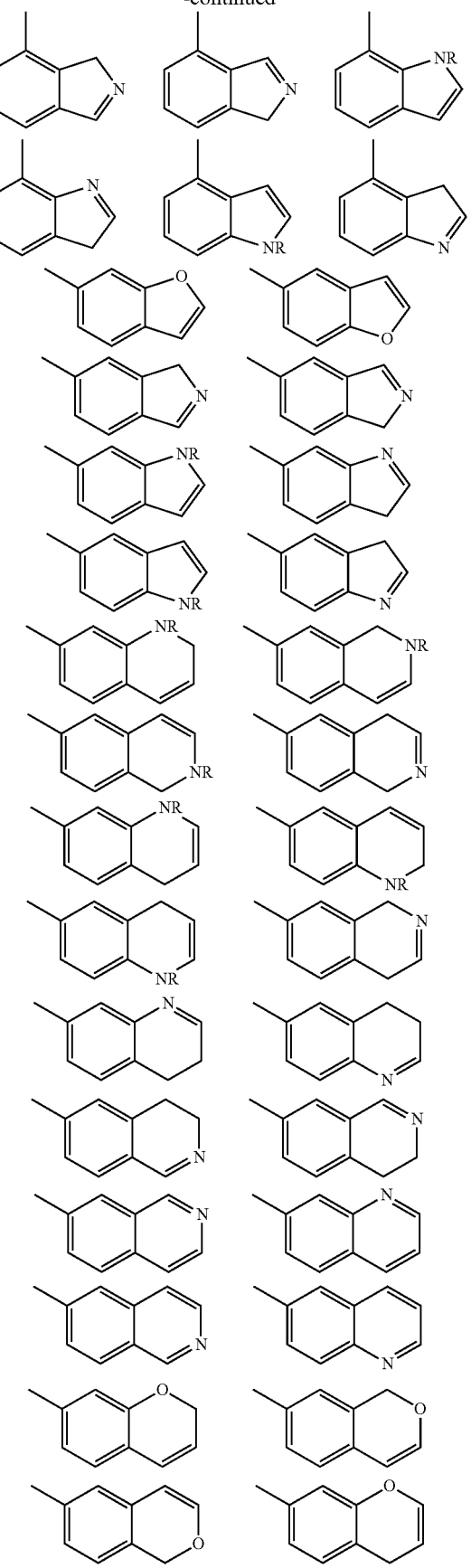

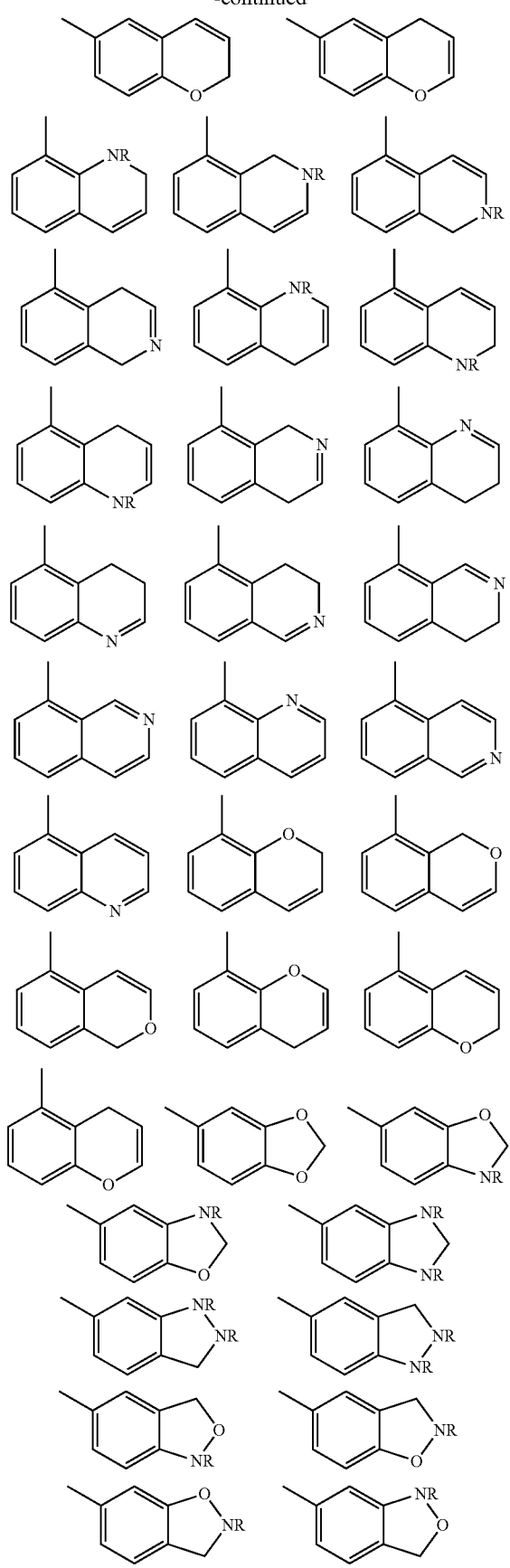
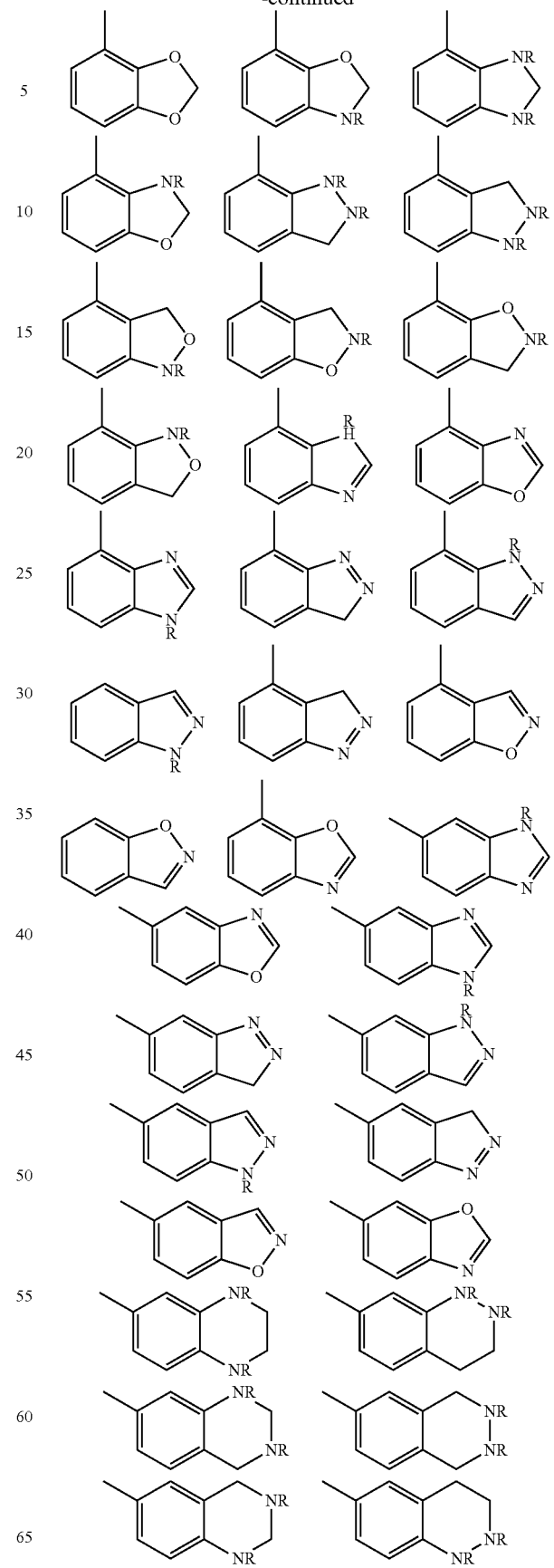

89
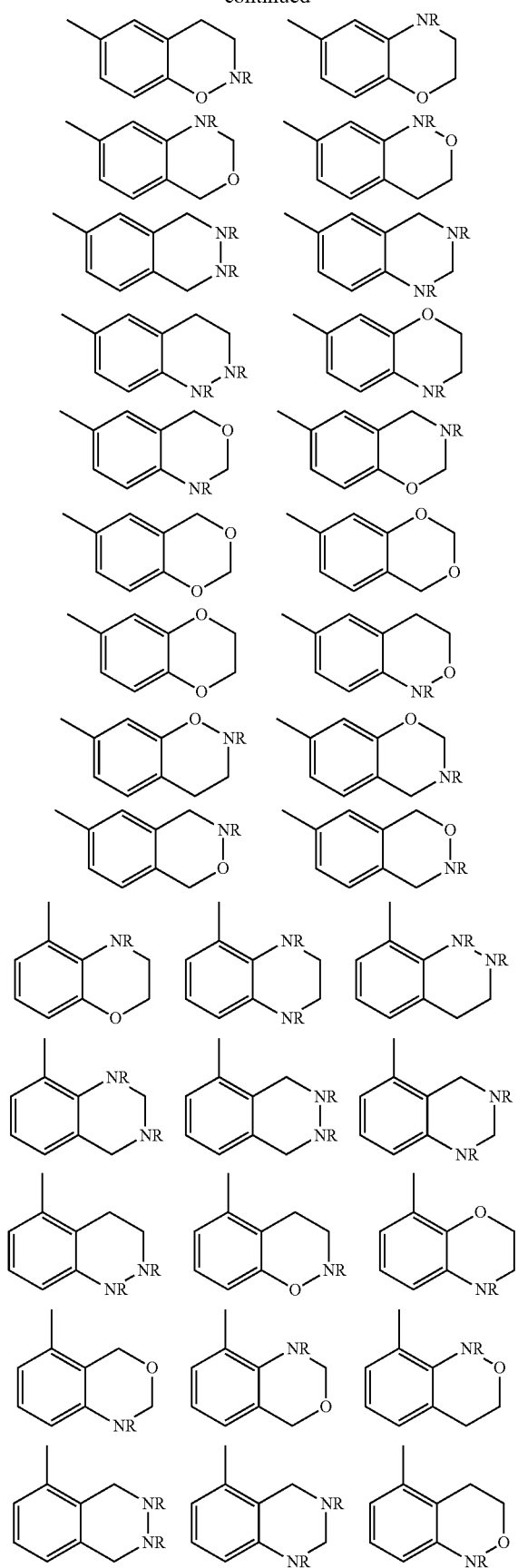
90
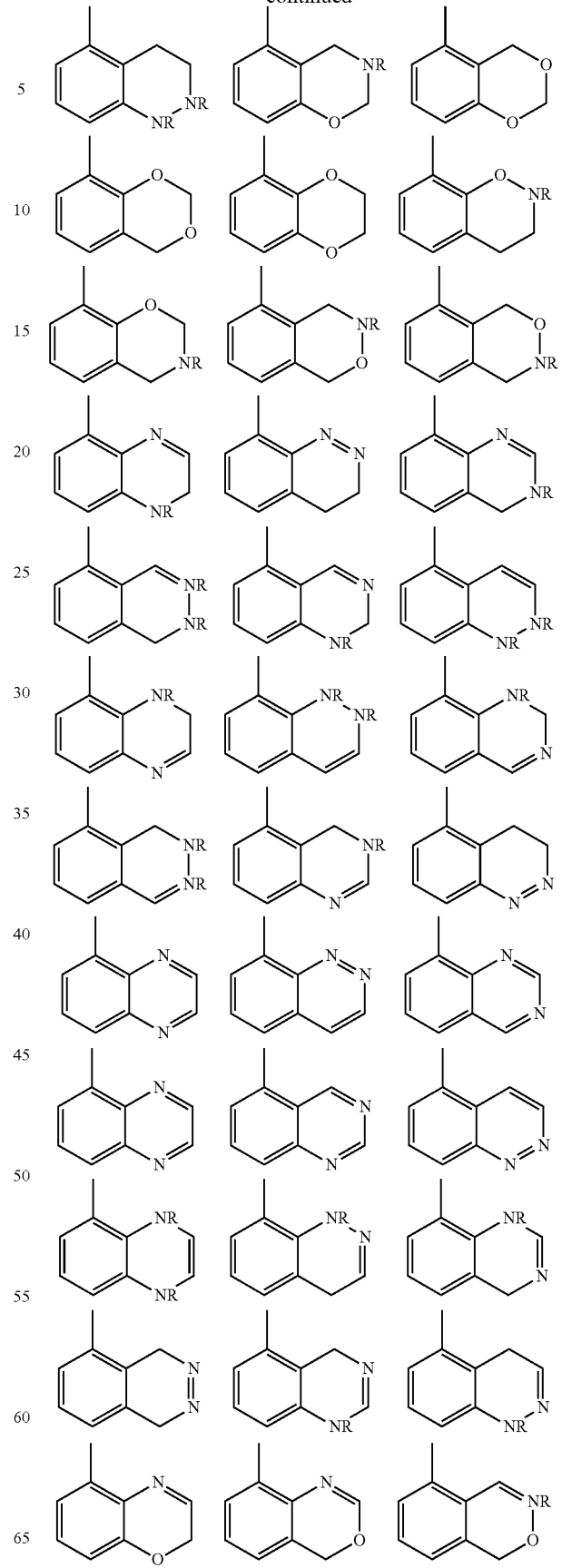

-continued
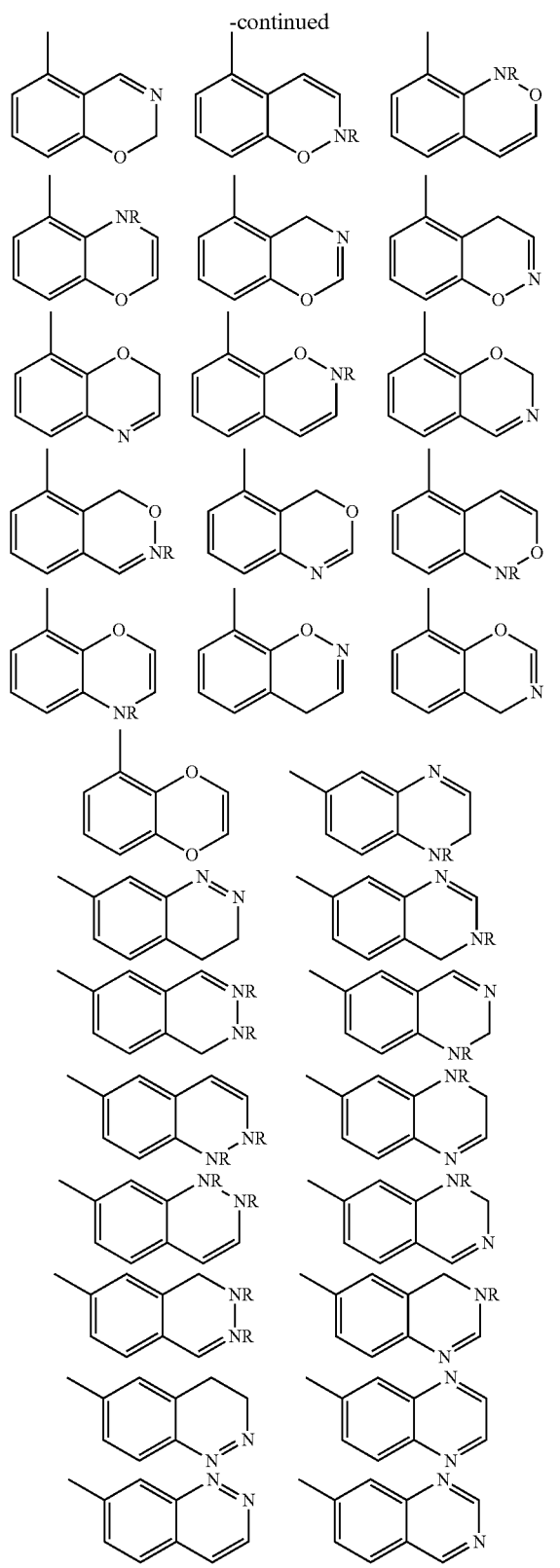
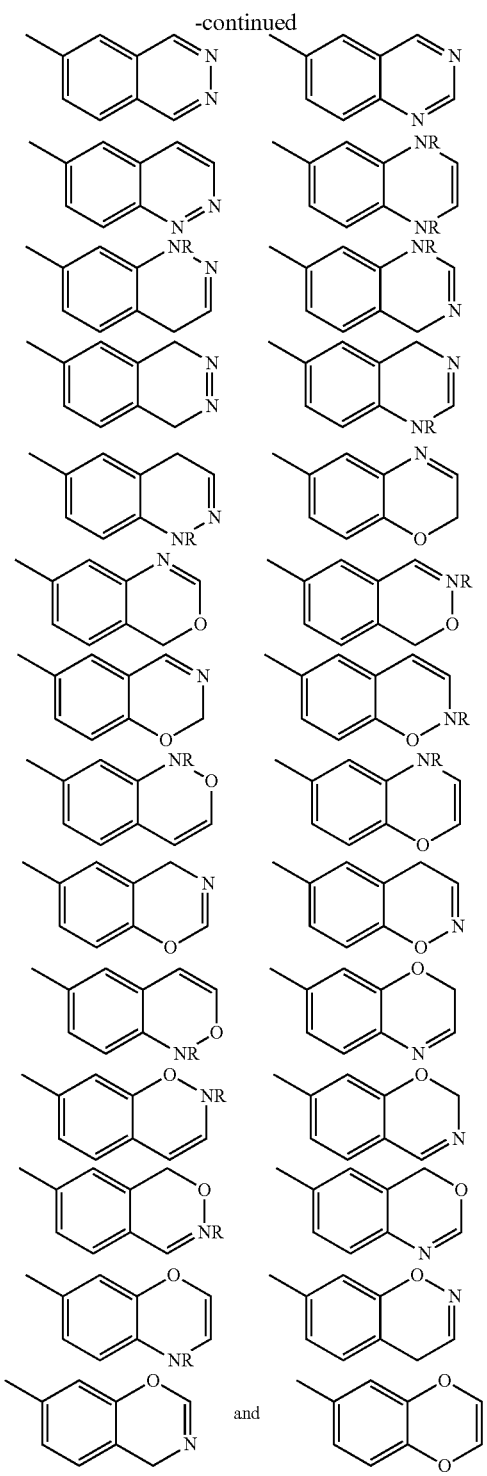
wherein R is selected from the group consisting of hydrogen, $C_{1-6}$alkyl, $C_{3-8}$cycloalkyl, heterocycloalkyl, aryl, and heteroaryl.
* * * * *